United States Patent
Watson et al.

(10) Patent No.: US 11,884,696 B2
(45) Date of Patent: *Jan. 30, 2024

(54) CRYSTALLINE 19-NOR C3,3-DISUBSTITUTED C21-N-PYRAZOLYL STEROID

(71) Applicant: Sage Therapeutics, Inc., Cambridge, MA (US)

(72) Inventors: Paul Steven Watson, Carrboro, NC (US); Bret Berner, Half Moon Bay, CA (US); John Gregory Reid, Wellington, FL (US); Jian Wang, Branchburg, NJ (US); James J. Doherty, Bedford, MA (US); Stephen Jay Kanes, Swarthmore, PA (US)

(73) Assignee: Sage Therapeutics, Inc., Cambridge, MA (US)

( * ) Notice: Subject to any disclaimer, the term of this patent is extended or adjusted under 35 U.S.C. 154(b) by 123 days.

This patent is subject to a terminal disclaimer.

(21) Appl. No.: 17/396,464

(22) Filed: Aug. 6, 2021

(65) Prior Publication Data
US 2022/0169674 A1    Jun. 2, 2022

Related U.S. Application Data

(63) Continuation of application No. 16/326,977, filed as application No. PCT/US2017/048267 on Aug. 23, 2017, now Pat. No. 11,236,121.

(60) Provisional application No. 62/378,582, filed on Aug. 23, 2016.

(51) Int. Cl.
| | | |
|---|---|---|
| C07J 43/00 | (2006.01) | |
| C07D 231/14 | (2006.01) | |
| A61P 25/22 | (2006.01) | |
| A61P 25/18 | (2006.01) | |
| A61P 25/24 | (2006.01) | |
| A61P 25/00 | (2006.01) | |
| A61P 25/08 | (2006.01) | |
| A61P 37/00 | (2006.01) | |

(52) U.S. Cl.
CPC ............ *C07J 43/003* (2013.01); *A61P 25/00* (2018.01); *A61P 25/08* (2018.01); *A61P 25/18* (2018.01); *A61P 25/22* (2018.01); *A61P 25/24* (2018.01); *A61P 37/00* (2018.01); *C07D 231/14* (2013.01); *C07B 2200/13* (2013.01)

(58) Field of Classification Search
CPC ......... C07J 43/003; A61P 25/00; A61P 25/08; A61P 25/18; A61P 25/22; A61P 25/24; A61P 37/00; C07B 2200/13; C07D 231/14
See application file for complete search history.

(56) References Cited

U.S. PATENT DOCUMENTS

| | | |
|---|---|---|
| 9,512,165 B2 | 12/2016 | Martinez Botella et al. |
| 9,630,986 B2 | 4/2017 | Covey et al. |
| 9,725,481 B2 | 8/2017 | Martinez Botella et al. |
| 9,765,110 B2 | 9/2017 | Covey |
| 10,172,871 B2 | 1/2019 | Martinez Botella et al. |
| 10,246,482 B2 | 4/2019 | Harrison et al. |
| 10,342,810 B2 | 7/2019 | Martinez Botella et al. |
| 11,241,446 B2 | 2/2022 | Martinez Botella et al. |
| 2005/0080107 A1 | 3/2005 | Shinohar |
| 2010/0152840 A1 | 6/2010 | Seguin et al. |
| 2011/0152840 A1 | 6/2011 | Lee et al. |
| 2014/0148412 A1 | 5/2014 | Hogenkamp |
| 2016/0108080 A1 | 4/2016 | Martinez Botella et al. |
| 2017/0233433 A1 | 8/2017 | Martinez Botella et al. |
| 2017/0246191 A1 | 8/2017 | Martinez Botella et al. |
| 2019/0177358 A1 | 6/2019 | Martinez Botella et al. |
| 2020/0155576 A1 | 5/2020 | Martinez Botella et al. |

FOREIGN PATENT DOCUMENTS

| | | |
|---|---|---|
| CN | 108727453 A | 11/2018 |
| RU | 2675855 C2 | 12/2018 |
| WO | 1991016897 A1 | 11/1991 |
| WO | 2001051919 A2 | 7/2001 |
| WO | 2003066590 A1 | 8/2003 |

(Continued)

OTHER PUBLICATIONS

Anonymous: "Archive History for NCT03000530", Aug. 4, 2017, Retrieved from the Internet: <URL:https://www.clinicaltrials.gov/ct2/his>tory/NCT03000530?V-_6=View#StudyPageTop; [retrieved on Nov. 20, 2018].

(Continued)

*Primary Examiner* — Barbara P Badio
(74) *Attorney, Agent, or Firm* — Honigman LLP; Kathryn D. Doyle; Jonathan P. O'Brien

(57) ABSTRACT

This invention relates to a crystalline 19-nor C3,3-disubstituted C21-pyrazolyl steroid of Formula (I),

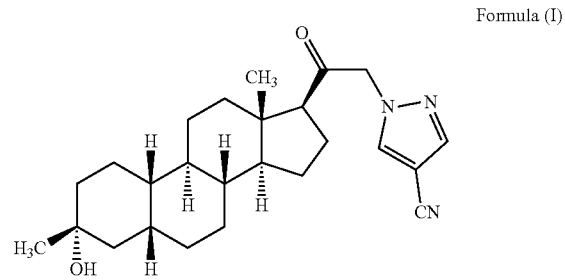

Formula (I)

and compositions thereof. Also disclosed herein are methods of making the same and methods of using the same.

19 Claims, 31 Drawing Sheets

(56) References Cited

FOREIGN PATENT DOCUMENTS

| | | | |
|---|---|---|---|
| WO | 2013043985 A1 | 3/2013 |
| WO | 2014085668 A1 | 6/2014 |
| WO | 2014169833 A1 | 10/2014 |
| WO | 2015195962 A1 | 12/2015 |
| WO | 2016040322 A1 | 3/2016 |
| WO | 2016061537 A1 | 4/2016 |
| WO | 2016209847 A1 | 12/2016 |
| WO | 2017044659 A1 | 3/2017 |
| WO | 2017066626 A1 | 4/2017 |
| WO | 2017087864 A1 | 5/2017 |
| WO | 2017156103 A1 | 9/2017 |
| WO | 2017156418 A1 | 9/2017 |
| WO | 2018013613 A1 | 1/2018 |
| WO | 2018013615 A1 | 1/2018 |
| WO | 2018039378 A1 | 3/2018 |
| WO | 2019018119 A1 | 1/2019 |
| WO | 2019045121 A1 | 3/2019 |
| WO | 2019051264 A1 | 3/2019 |
| WO | 2019051477 A1 | 3/2019 |
| WO | 2019055764 A1 | 3/2019 |
| WO | 2019094724 A1 | 5/2019 |
| WO | 2019113494 A1 | 6/2019 |
| WO | 2019126741 A1 | 6/2019 |
| WO | 2019126761 A1 | 6/2019 |
| WO | 2019140272 A1 | 7/2019 |
| WO | 2019241442 A1 | 12/2019 |
| WO | 2020077255 A1 | 4/2020 |
| WO | 2020082065 A1 | 4/2020 |
| WO | 2020118060 A1 | 6/2020 |
| WO | 2020132504 A1 | 6/2020 |
| WO | 2020243027 A1 | 12/2020 |
| WO | 2020243488 A1 | 12/2020 |
| WO | 2021113786 A1 | 6/2021 |
| WO | 2021188778 A1 | 9/2021 |
| WO | 2021195297 A1 | 9/2021 |
| WO | 2021195301 A1 | 9/2021 |
| WO | 2022020363 A1 | 1/2022 |

OTHER PUBLICATIONS

Balbach, S., et al., "Pharmaceutical evaluation of early development candidates "The 100 mg approach"", International Journal of Pharmaceutica, 2004, vol. 275, pp. 1-12.

Bernstein, BE., "Rett Syndrome Medication" [online], Updated Feb. 6, 2017, [retrieved on May 3, 2018]. Retrieved from the website Medscape, using internet URL: <https://emedicine.medscape.com/article/916377-medication>.

Caira, M.R., "Crystalline Polymorphism of Organic Compounds", Topics in Current Chemistry, vol. 198, 1998, pp. 163-208.

Gunduz-Bruce et al.,"Sage-217 in Subjects with Major Depressive Disorder: Efficacy and Safety Results from Open-Label Part A of a Phase 2a Study", Poster, (Presented on Sep. 2-5, 2017 at the 30th ECNP Congress, Paris, France.

International Search Report and Written Opinion for Corresponding International Application No. PCT/US2016/062874 dated Jan. 30, 2017.

International Search Report and Written Opinion for Corresponding International Application No. PCT/US2017/041600 dated Dec. 1, 2017.

International Search Report and Written Opinion for Corresponding International Application No. PCT/US2017/041605 dated Dec. 12, 2017.

International Search Report and Written Opinion for Corresponding International Application No. PCT/US2018/050012 dated Dec. 7, 2018.

International Search Report and Written Opinion for Corresponding International Application No. PCT/US2018/051048 dated Jan. 11, 2019.

International Search Report and Written Opinion for Corresponding International Application No. PCT/US2018/064546 dated Apr. 9, 2019.

International Search Report and Written Opinion for International Application No. PCT/US2018/067277 dated May 24, 2019.

International Search Report and Written Opinion for International Application No. PCT/US2018/067306 dated May 28, 2019.

Sage Therapeutics: "Sage Therapeutics Advances SAGE-217 into Placebo-Controlled Phase 2 Clinical Trial in Major Depressive Disorder", Feb. 13, 2017, Retrieved from the Internet: <URL:https://investor.sagerx.com/static-fil>es/80fff1f35-fc4c-4eb2-9456-3228ec891a59; [retrieved on Dec. 21, 2018].

Singhal, D., et al., "Drug Polymorphism and dosage form design: a practical perspective", Advanced Drug Delivery Reviews, 2004, vol. 56, pp. 335-347.

Supplemental European Search Report, European Patent Application No. 14826212.4, dated Feb. 16, 2017.

Zonana et al., "The Neurobiology of Postpartum Depression", CNS Spectrums, (2005), pp. 792-799, 805.

Brittain, H. G., Polymorphism in Pharmaceutical Solids, Informa Healthcare, 2009.

Bryn, S., et al., "Pharmaceutical Solids: A Strategic Approach to Regulatory Considerations", Pharmaceutical Research 1995, v. 12, pp. 945-954.

Censi, R. et al., Polymorph Impact on the Bioavailability and Stability of Poorly Soluble Drugs. Molecules, Oct. 15, 2015, vol. 20, No. 10, pp. 18759-18776.

Lee, E. H., A practical guide to pharmaceutical polymorph screening & selection. Asian Journal of Pharmaceutical Sciences, May 16, 2014, vol. 9, No. 4, pp. 163-175.

Newman, A., Specialized Solid Form Screening Techniques. Organic Process Research & Development, Oct. 30, 2012, vol. 13, No. 3, pp. 457-471.

Japanese Office Action dated Sep. 6, 2021 issued in Japanese Application No. JP 2019-210657, 8 pages.

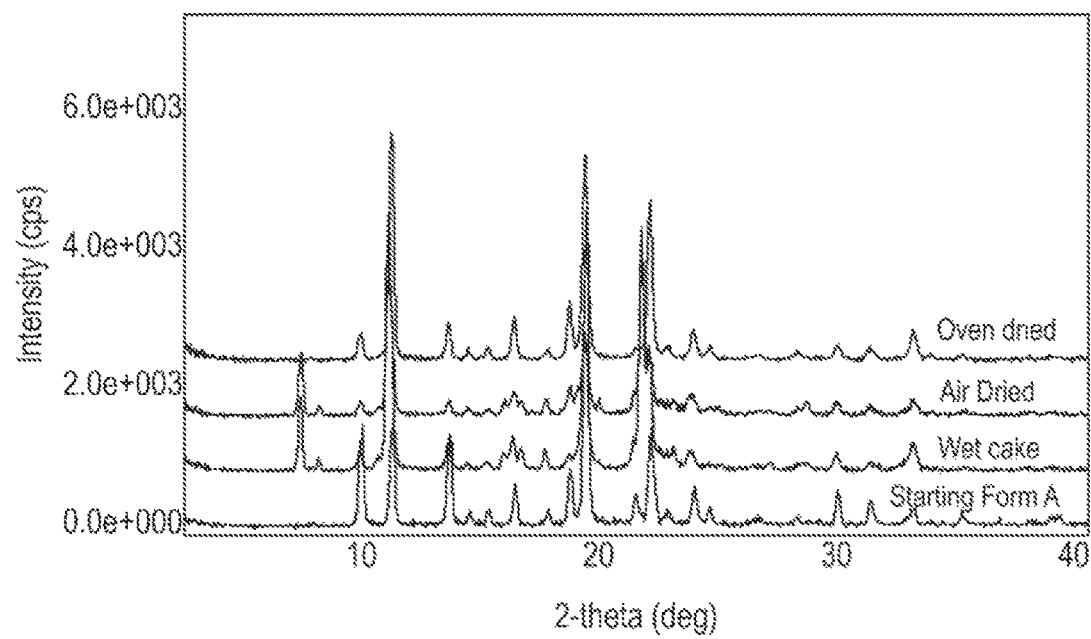
FIG. 16
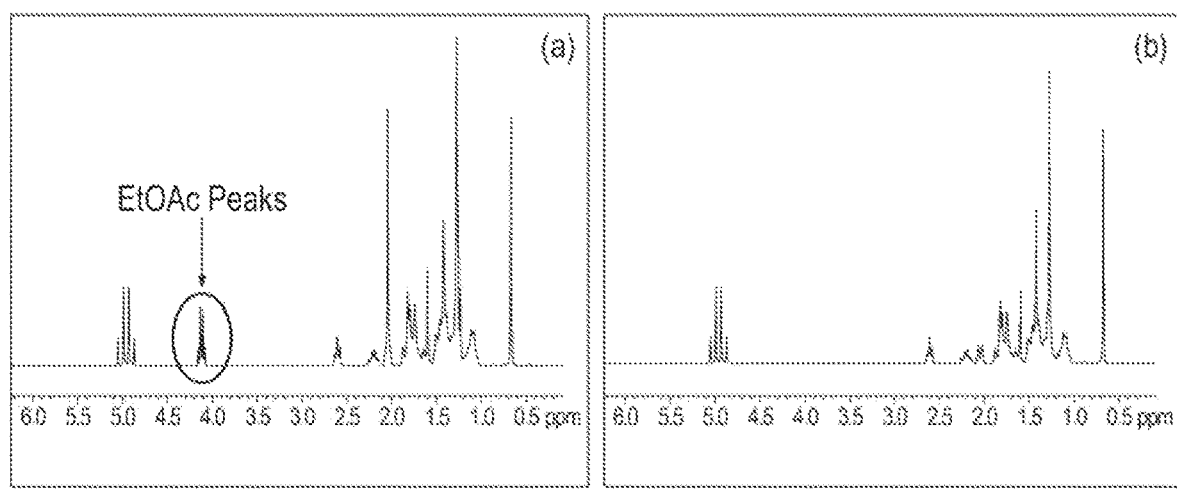
FIG. 17A
FIG. 17B

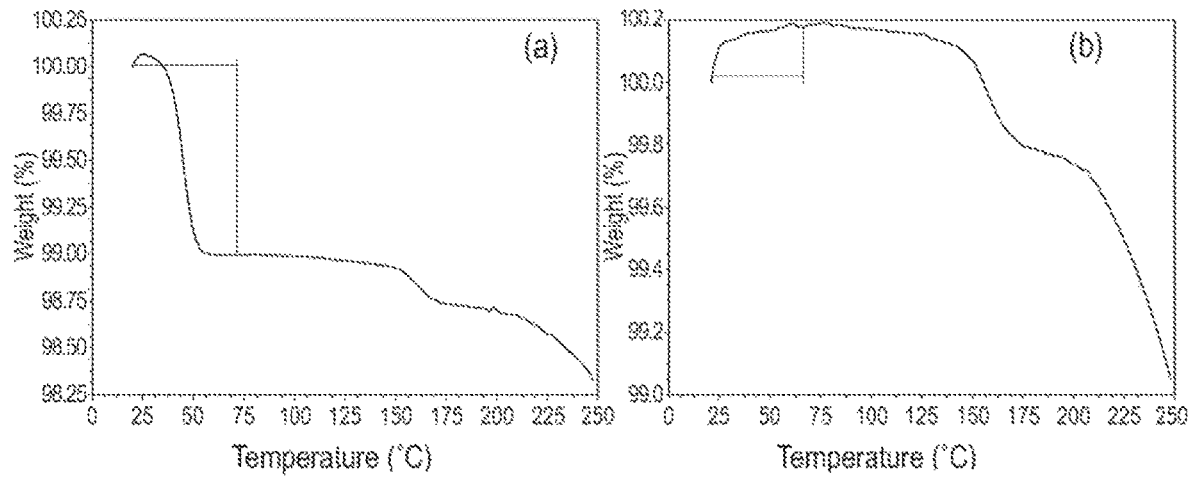
FIG. 18A  FIG. 18B
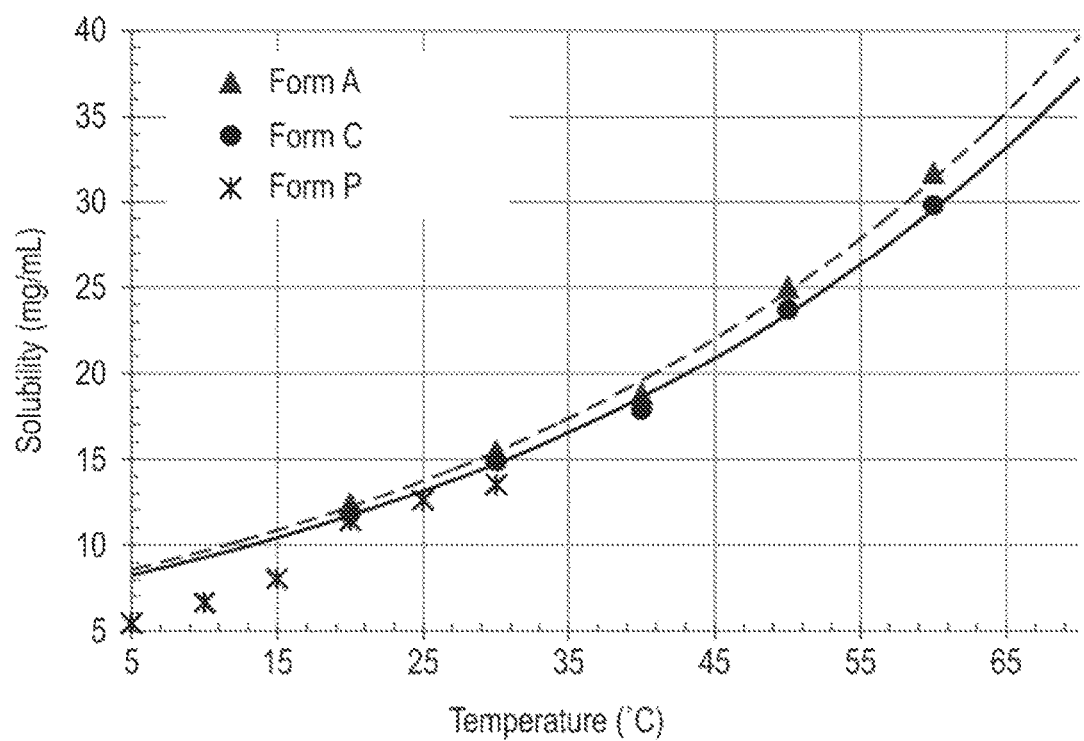
FIG. 19

CRYSTALLINE 19-NOR C3,3-DISUBSTITUTED C21-N-PYRAZOLYL STEROID

CROSS-REFERENCE TO RELATED APPLICATIONS

This application is a continuation of U.S. Ser. No. 16/326,977, filed Feb. 21, 2019, which is a national stage application under 35 U.S.C. § 371 of International Application No. PCT/US2017/048267 filed, Aug. 23, 2017, which claims priority under 35 U.S.C. § 119(e) to U.S. Ser. No. 62/378,582 filed Aug. 23, 2016, which is incorporated herein by reference in its entirety.

BACKGROUND OF THE INVENTION

Brain excitability is defined as the level of arousal of an animal, a continuum that ranges from coma to convulsions, and is regulated by various neurotransmitters. In general, neurotransmitters are responsible for regulating the conductance of ions across neuronal membranes. At rest, the neuronal membrane possesses a potential (or membrane voltage) of approximately −70 mV, the cell interior being negative with respect to the cell exterior. The potential (voltage) is the result of ion ($K^+$, $Na^+$, $Cl^-$, organic anions) balance across the neuronal semipermeable membrane. Neurotransmitters are stored in presynaptic vesicles and are released under the influence of neuronal action potentials. When released into the synaptic cleft, an excitatory chemical transmitter such as acetylcholine will cause membrane depolarization (change of potential from −70 mV to −50 mV). This effect is mediated by postsynaptic nicotinic receptors which are stimulated by acetylcholine to increase membrane permeability to $Na^+$ ions. The reduced membrane potential stimulates neuronal excitability in the form of a postsynaptic action potential.

In the case of the γ-aminobutyric acid receptor complex (GRC), the effect on brain excitability is mediated by γ-aminobutyric acid (GABA), a neurotransmitter. GABA has a profound influence on overall brain excitability because up to 40% of the neurons in the brain utilize GABA as a neurotransmitter. GABA regulates the excitability of individual neurons by regulating the conductance of chloride ions across the neuronal membrane. GABA interacts with its recognition site on the GRC to facilitate the flow of chloride ions down an electrochemical gradient of the GRC into the cell. An intracellular increase in the levels of this anion causes hyperpolarization of the transmembrane potential, rendering the neuron less susceptible to excitatory inputs (i.e., reduced neuron excitability). In other words, the higher the chloride ion concentration in the neuron, the lower the brain excitability (the level of arousal).

New and improved neuroactive crystalline forms of steroids are needed that act as modulating agents for brain excitability, as well as agents for the prevention and treatment of CNS-related diseases. Crystalline forms of such a steroid described herein are directed toward this end.

SUMMARY OF THE INVENTION

The present invention relates, in part, to novel forms (for example, certain crystalline forms described herein) of a 19-nor (i.e., C19 desmethyl) compound. Generally, a solid compound's efficacy as a drug can be affected by the properties of the solid it comprises.

Thus, in one aspect, described herein is a crystalline compound of Formula (I):

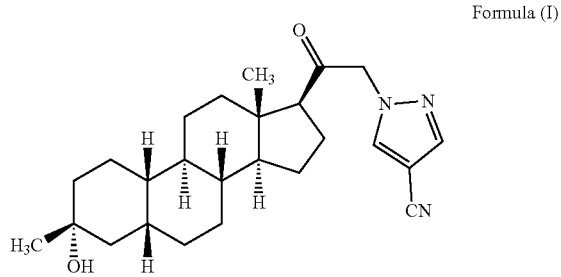

Formula (I)

also referred to herein as "Compound 1."

In some embodiments, a solubilized form of the crystalline form of Compound 1 is converted to a different crystalline form of Compound 1 by slow evaporation, anti-solvent addition, slow-cooling, solution vapor diffusion, solid vapor diffusion, fast evaporation, reverse anti-solvent addition, and water activity experiments.

In some embodiments, a crystalline form of Compound 1 is converted to a different crystalline form of Compound 1 by slurry conversion.

In some embodiments, physical or chemical parameters of a solid form of Compound 1 are evaluated from one or more of the following analytical techniques: X-ray powder diffraction (XRPD) analysis, e.g., variable-temperature XRPD (VT-XRPD) analysis, single-crystal X-ray crystallography, thermogravimetric analysis (TGA), differential scanning calorimetry (DSC), nuclear magnetic resonance (NMR) spectroscopy or solid-state NMR spectroscopy, Raman spectroscopy, or dynamic vapor sorption (DVS).

In embodiments, each solid form is characterized and identified with parameters obtained from one or more of the aforementioned analytical methods:

X-ray diffraction patterns presented with degrees 2-theta (2θ) as the abscissa and peak intensity as the ordinate as determined by analysis with XRPD. These patterns are also referred to herein as XRPD patterns;

properties of the single-crystal structure of a solid form, e.g., unit cell, crystal system, and space group, as determined by single-crystal X-ray crystallography;

calculated XRPD patterns for a crystalline form as determined by data from single-crystal X-ray crystallography;

an endotherm specified by an onset temperature $T_{onset}$ that indicates a loss of solvent, a transformation from one crystalline form to another, or a melting point as determined by DSC performed at a specific ramp rate;

a value for weight loss as determined by TGA;

a value for weight gain at a temperature of 25° C. and a relative humidity between 5% and 95% as determined by DVS; and an exemplary $^1$H NMR spectrum of Compound 1 dissolved in deuterated dimethyl sulfoxide (DMSO-$d_6$).

In embodiments, a solid form is determined to be crystalline by the presence of sharp, distinct peaks found in the corresponding XRPD pattern.

In some embodiments, XRPD is used to determine if a solid form of Compound 1 transforms to another solid form at temperatures higher than room temperature.

In some embodiments, crystalline Compound 1 is an anhydrate.

In some embodiments, crystalline Compound 1 is a solvate.

In some embodiments, crystalline Compound 1 can have an XRPD pattern with characteristic peaks between and including the following values of 2θ in degrees: 11.6 to 12.0 (e.g., 11.8), 13.7 to 14.1 (e.g., 13.9), 14.0 to 14.4 (e.g., 14.2), 16.6 to 17.0 (e.g., 16.8), 18.9 to 19.3 (e.g., 19.1), 19.1 to 19.5 (e.g., 19.3), 19.9 to 20.3 (e.g., 20.1), 21.1 to 21.5 (e.g., 21.3), 21.9 to 22.3 (e.g., 22.1), and 23.0 to 23.4 (e.g., 23.2).

In some embodiments, crystalline Compound 1 can have an XRPD pattern with characteristic peaks between and including the following values of 2θ in degrees: 11.6 to 12.0 (e.g., 11.8), 16.6 to 17.0 (e.g., 16.8), 18.9 to 19.3 (e.g., 19.1), 19.9 to 20.3 (e.g., 20.1), and 23.0 to 23.4 (e.g., 23.2).

In some embodiments, crystalline Compound 1 has an XRPD pattern with characteristic peaks at the following values of 2θ in degrees: 11.8, 13.9, 14.2, 16.8, 19.1, 19.3, 20.1, 21.3, 22.1, and 23.2.

In some embodiments, crystalline Compound 1 has an XRPD pattern with characteristic peaks at the following values of 2θ in degrees: 11.8, 16.8, 19.1, 20.1, and 23.2.

In some embodiments, crystalline Compound 1 has an XRPD pattern substantially as depicted in FIG. 10A.

In some embodiments, crystalline Compound 1 has an XRPD pattern with characteristic peaks between and including the following values of 2θ in degrees: 9.3 to 9.7 (e.g., 9.5), 10.6 to 11.0 (e.g., 10.8), 13.0 to 13.4 (e.g., 13.2), 14.7 to 15.1 (e.g., 14.9), 15.8 to 16.2 (e.g., 16.0), 18.1 to 18.5 (e.g., 18.3), 18.7 to 19.1 (e.g., 18.9), 20.9 to 21.3 (e.g., 21.1), 21.4 to 21.8 (e.g., 21.6), and 23.3 to 23.7 (e.g., 23.5).

In some embodiments, crystalline Compound 1 has an XRPD pattern with characteristic peaks between and including the following values of 2θ in degrees: 9.3 to 9.7 (e.g., 9.5), 10.6 to 11.0 (e.g., 10.8), 13.0 to 13.4 (e.g., 13.2), 18.7 to 19.1 (e.g., 18.9), and 21.4 to 21.8 (e.g., 21.6).

In some embodiments, crystalline Compound 1 has an XRPD pattern with characteristic peaks at the following values of 2θ in degrees: 9.5, 10.8, 13.2, 14.9, 16.0, 18.3, 18.9, 21.1, 21.6, and 23.5.

In some embodiments, crystalline Compound 1 has an XRPD pattern with characteristic peaks at the following values of 2θ in degrees: 9.5, 10.8, 13.2, 18.9, and 21.6.

In some embodiments, crystalline Compound 1 has an XRPD pattern substantially as depicted in FIG. 1A.

In some embodiments, crystalline Compound 1 has comprises a unit cell substantially as depicted in FIG. 1B.

In some embodiments, a crystalline form of Compound 1, when subjected to a temperature from about 150° C. to about 195° C., e.g., from 157° C. to 170° C., transforms into a different crystalline form as indicated by DSC at a ramp rate of 10° C./min.

In some embodiments, crystalline Compound 1 melts at a $T_{onset}$ from about 200° C. to about 225° C., e.g., from about 205° C. to about 225° C., e.g., from about 208° C. to about 215° C., as measured by DSC at a ramp rate of 10° C./min.

In some embodiments, crystalline Compound 1 can have an XRPD pattern with characteristic peaks between and including the following values of 2θ in degrees: 9.7 to 10.1 (e.g., 9.9), 11.6 to 12.0 (e.g., 11.8), 13.2 to 13.6 (e.g., 13.4), 14.2 to 14.6 (e.g., 14.4), 14.6 to 15.0 (e.g., 14.8), 16.8 to 17.2 (e.g., 17.0), 20.5 to 20.9 (e.g., 20.7), 21.3 to 21.7 (e.g., 21.5), 21.4 to 21.8 (e.g., 21.6), and 22.4 to 22.8 (e.g., 22.6).

In some embodiments, crystalline Compound 1 can have an XRPD pattern with characteristic peaks between and including the following values of 2θ in degrees: 9.7 to 10.1 (e.g., 9.9), 14.6 to 15.0 (e.g., 14.8), 16.8 to 17.2 (e.g., 17.0), 20.5 to 20.9 (e.g., 20.7), and 21.3 to 21.7 (e.g., 21.5).

In some embodiments, crystalline Compound 1 has an XRPD pattern with characteristic peaks at the following values of 2θ in degrees: 9.9, 11.8, 13.4, 14.4, 14.8, 17.0, 20.7, 21.5, 21.6, and 22.6.

In some embodiments, crystalline Compound 1 has an XRPD pattern with characteristic peaks at the following values of 2θ in degrees: 9.9, 14.8, 17.0, 20.7, and 21.5.

In some embodiments, crystalline Compound 1 has an XRPD pattern substantially as depicted in FIG. 3A.

In some embodiments, crystalline Compound 1 has comprises a unit cell substantially as depicted in FIG. 3B.

In some embodiments, a crystalline form of Compound 1, when subjected to a temperature from about 180° C. to about 200° C., e.g., from about 184° C. to about 200° C., e.g., from about 184° C. to about 190° C., transforms into a different crystalline form as indicated by DSC at a ramp rate of 10° C./min.

In some embodiments, crystalline Compound 1 melts at a $T_{onset}$ from about 200° C. to about 225° C., e.g., from about 211° C. to about 215° C., as measured by DSC at a ramp rate of 10° C./min.

In some embodiments, crystalline Compound 1 has any of the XRPD patterns substantially as depicted in FIG. 2B.

In some embodiments, crystalline Compound 1 has an XRPD pattern substantially as depicted in FIG. 4A.

In some embodiments, crystalline Compound 1 has an XRPD pattern substantially as depicted in FIG. 5.

In some embodiments, crystalline Compound 1 has an XRPD pattern substantially as depicted in FIG. 6A.

In some embodiments, crystalline Compound 1 has an XRPD pattern substantially as depicted in FIG. 7A.

In some embodiments, crystalline Compound 1 has an XRPD pattern substantially as depicted in FIG. 8A.

In some embodiments, crystalline Compound 1 has an XRPD pattern substantially as depicted in FIG. 9A.

In some embodiments, crystalline Compound 1 has an XRPD pattern substantially as depicted in FIG. 11A.

In some embodiments, crystalline Compound 1 has an XRPD pattern substantially as depicted in FIG. 12.

In some embodiments, crystalline Compound 1 has an XRPD pattern substantially as depicted in FIG. 13A.

In some embodiments, crystalline Compound 1 has an XRPD pattern substantially as depicted in FIG. 14A.

In some embodiments, crystalline Compound 1 has an XRPD pattern substantially as any of those depicted in FIG. 16.

In one aspect, the invention describes a method for transforming the crystalline compound having an XRPD pattern with characteristic peaks at the following values of 2θ in degrees: 11.8, 16.8, 19.1, 20.1, and 23.2 to the crystalline compound having an XRPD pattern with characteristic peaks at the following values of 2θ in degrees: 9.5, 10.8, 13.2, 18.9, and 21.6, the method comprising crystallization from a solubilized form of Compound 1 or slurry conversion.

In some embodiments, the transformation is performed using ethyl acetate as a solvent at a temperature from about 50° C. to about 70° C., e.g., from 60° C. to 65° C.

In some embodiments, the transformation is performed in the presence of seed crystals of the crystalline compound having an XRPD pattern with characteristic peaks at the following values of 2θ in degrees: 9.5, 10.8, 13.2, 18.9, and 21.6 at a loading from about 0.1% to about 5.0%, e.g. from 0.2% to 1.0%, of the total amount of Compound 1 present.

In one aspect, the present invention describes a pharmaceutical composition comprising a crystalline form of Compound 1, and a pharmaceutically acceptable excipient.

In one aspect, the present invention describes a method for treating a CNS-related disorder in a subject in need thereof, comprising administering to the subject an effective amount of Compound 1, e.g., a crystalline solid form of Compound 1 described herein, a pharmaceutically acceptable salt thereof, or a pharmaceutical composition thereof.

In some embodiments, the CNS-related disorder is a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, or tinnitus.

In some embodiments, crystalline Compound 1 is administered orally, parenterally, intradermally, intrathecally, intramuscularly, subcutaneously, vaginally, as a buccal, sublingually, rectally, as a topical, inhalation, intranasal, or transdermally.

In some embodiments, crystalline Compound 1 is administered chronically.

In another aspect, provided herein is a method of treating a neurological disorder, a psychiatric disorder, a seizure disorder, a neuroinflammatory disorder, a glaucoma or metabolic disorder, a sensory deficit disorder, in a subject in need thereof, comprising administering to the subject an effective amount of Compound 1 or a pharmaceutically acceptable composition thereof.

In another aspect, provided herein, is a method of using Compound 1 or a pharmaceutically acceptable composition thereof, as a neuroprotectant, comprising administering to a subject in need thereof an effective amount of Compound 1 or a pharmaceutically acceptable composition thereof.

In another aspect, provided herein, is a method of using Compound 1 or a pharmaceutically acceptable composition thereof, as an analgesic or other agent for pain control, comprising administering to a subject in need thereof an effective amount of Compound 1 or a pharmaceutically acceptable composition thereof. In some embodiments, the compound or pharmaceutically acceptable composition is used as an analgesic or other agent for pain control to treat inflammatory pain, neuropathic pain, fibromyalgia, or peripheral neuropathy.

As used herein, "XRPD" refers to X-ray powder diffraction. As used herein, "VT-XRPD" refers to variable temperature-X-ray powder diffraction. As used herein, "TGA" refers to thermogravimetric analysis. As used herein, DSC refers to differential scanning calorimetry. As used herein, "NMR" refers to nuclear magnetic resonance. As used herein, "DVS" refers to dynamic vapor sorption. As used herein, "DCM" refers to dichloromethane. As used herein, "EtOAc" refers to ethyl acetate. As used herein, "MeOH" refers to methanol. As used herein, "MBTE" refers to methyl tert-butyl ether. As used herein, "RH" refers to relative humidity.

As used herein, "crystalline" refers to a solid having a highly regular chemical structure, i.e., having long range structural order in the crystal lattice. The molecules are arranged in a regular, periodic manner in the 3-dimensional space of the lattice. In particular, a crystalline form may be produced as one or more single crystalline forms. For the purposes of this application, the terms "crystalline form", "single crystalline form," "crystalline solid form," "solid form," and "polymorph" are synonymous and used interchangably; the terms distinguish between crystals that have different properties (e.g., different XRPD patterns and/or different DSC scan results).

The term "substantially crystalline" refers to forms that may be at least a particular weight percent crystalline. Particular weight percentages are 70%, 75%, 80%, 85%, 87%, 88%, 89%, 90%, 91%, 92%, 93%, 94%, 95%, 96%, 97%, 98%, 99%, 99.5%, 99.9%, or any percentage between 70% and 100%. In certain embodiments, the particular weight percent of crystallinity is at least 90%. In certain other embodiments, the particular weight percent of crystallinity is at least 95%. In some embodiments, Compound 1 can be a substantially crystalline sample of any of the crystalline solid forms described herein (e.g., Forms, A, B, C, D, E, F, H, I, J, K, L, M, N, O, and P).

The term "substantially pure" relates to the composition of a specific crystalline solid form of Compound 1 that may be at least a particular weight percent free of impurities and/or other solid forms of Compound 1. Particular weight percentages are 70%, 75%, 80%, 85%, 90%, 95%, 99%, or any percentage between 70% and 100%. In some embodiments, Compound 1 can be a substantially pure sample of any of the crystalline solid forms described herein. (e.g., Forms, A, B, C, D, E, F, H, I, J, K, L, M, N, O, and P). In some embodiments, Compound 1 can be substantially pure Form A. In some embodiments, Compound 1 can be substantially pure Form B. In some embodiments, Compound 1 can be substantially pure Form C. In some embodiments, Compound 1 can be substantially pure Form D. In some embodiments, Compound 1 can be substantially pure Form E. In some embodiments, Compound 1 can be substantially pure Form F. In some embodiments, Compound 1 can be substantially pure Form H. In some embodiments, Compound 1 can be substantially pure Form I. In some embodiments, Compound 1 can be substantially pure Form J. In some embodiments, Compound 1 can be substantially pure Form K. In some embodiments, Compound 1 can be substantially pure Form L. In some embodiments, Compound 1 can be substantially pure Form M. In some embodiments, Compound 1 can be substantially pure Form N. In some embodiments, Compound 1 can be substantially pure Form O. In some embodiments, Compound 1 can be substantially pure Form P.

As used herein, the term "anhydrous" or "anhydrate" when referring to a crystalline form of Compound 1 means that no solvent molecules, including those of water, form a portion of the unit cell of the crystalline form. A sample of an anhydrous crystalline form may nonetheless contain solvent molecules that do not form part of the unit cell of the anhydrous crystalline form, e.g., as residual solvent molecule left behind from the production of the crystalline form. In a preferred embodiment, a solvent can make up 0.5% by weight of the total composition of a sample of an anhydrous form. In a more preferred embodiment, a solvent can make up 0.2% by weight of the total composition of a sample of an anhydrous form. In some embodiments, a sample of an anhydrous crystalline form of Compound 1 contains no solvent molecules, e.g., no detectable amount of solvent. The term "solvate" when referring to a crystalline form of Compound 1 means that solvent molecules, e.g., organic solvents and water, form a portion of the unit cell of the crystalline form. Solvates that contain water as the solvent are also referred to herein as "hydrates." The term "isomorphic" when referring to a crystalline form of Compound 1 means that the form can comprise different chemical constituents, e.g., contain different solvent molecules in the unit cell, but have identical XRPD patterns. Isomorphic crystalline forms are sometimes referred to herein as "isomorphs."

A crystalline form of Compound 1 described herein, e.g., Form K, can melt at a specific temperature or across a range of temperatures. Such a specific temperature or range of temperatures can be represented by the onset temperature ($T_{onset}$) of the melting endotherm in the crystalline form's DSC trace. In some embodiments, at such an onset temperature, a sample of a crystalline form of Compound 1 melts and undergoes a concurrently occurring side-process, e.g., recrystallization or chemical decomposition. In some embodiments, at such an onset temperature, a crystalline form of Compound 1 melts in the absence of other concurrently occurring processes.

The term "characteristic peaks" when referring to the peaks in an XRPD pattern of a crystalline form of Compound 1 refers to a collection of certain peaks whose values of 2θ across a range of 0°-40° are, as a whole, uniquely assigned to one of the crystalline forms of Compound 1.

BRIEF DESCRIPTION OF THE DRAWINGS

FIG. 16 depicts exemplary XRPD patterns of Form P corresponding to wet sample ("Wet cake"), air dried sample at room temperature ("Air Dried"), and oven-dried sample at 40° C. ("Oven dried). An exemplary XRPD of a reference sample of Form A is also provided.

FIG. 17A depicts an exemplary $^1$H NMR spectrum of Form P after air-drying at room temperature.

FIG. 17B depicts an exemplary $^1$H NMR spectrum of Form P after oven-drying at 40° C.

FIG. 18A depicts an exemplary TGA curve of Form P after air-drying at room temperature.

FIG. 18B depicts an exemplary TGA curve of Form P after oven-drying at 40° C.

FIG. 19. depicts an exemplary plot of solubility data of Forms A, C, and P in ethyl acetate.

DETAILED DESCRIPTION OF CERTAIN EMBODIMENTS OF THE INVENTION

In one aspect, the present invention describes a compound of Formula (I), also referred to herein as "Compound 1," has been found to exist as different crystalline forms as indicated by various analytical methods. Compound 1 and its chemical synthesis are previously disclosed in U.S. Patent Application Publication No. US 20160083417 and PCT Application Publication No. WO 2014169831. The individual solid forms of the present invention are provided in Table 1 below:

TABLE 1

Summary of the Crystalline Forms of Compound 1.
Polymorph

Form A
Form B
Form C
Form D
Form E
Form F
Form H
Form I
Form J
Form K
Form L
Form M
Form N
Form O
Form P Solid forms of Compound 1 Methods of Making the Same Forms B, C, D, E, F, H, I, J, K, N, and O were prepared from Form A using various crystallization techniques described herein. Forms L and M were additionally prepared from Form B using other methods described herein. These forms were subsequently characterized by one or more of the following analytical techniques: X-ray powder diffraction (XRPD), e.g., variable-temperature X-ray powder diffraction (VT-XRPD), thermogravimetric analysis (TGA), differential scanning calorimetry (DSC), or dynamic vapor sorption (DVS). The single-crystal structures, including the unit cells, of Form A and Form C were determined from data obtained with an X-ray diffractometer. Furthermore, calculated XRPD patterns for Form A and Form C were obtained using their single-crystal X-ray diffraction data. In the present invention, DSC and TGA data were obtained using a ramp rate of 10° C./min.

Form A

Form A can be prepared by stirring crude Compound 1 as a slurry in ethyl acetate below 10° C. and then filtering and drying under vacuum or by dissolving crude Compound 1 in dichloromethane and then re-concentrating the solution twice with ethyl acetate under vacuum to dryness. Form A can be determined to be a crystalline form of Compound 1 by XRPD. TGA, together with single-crystal structure of Form A, can be used to conclude that Form A is anhydrous. DSC can be used to indicate the presence of two endotherms occurring at temperatures below 300° C.: one endotherm with a $T_{onset}$ of 157.2° C. that represents the transformation of Form A into Form K, and another with a $T_{onset}$ of 203.8° C. that represents the melting point of Form K. DVS can be used to demonstrate that Form A exhibits less than 0.30 weight percent water uptake at a relative humidity (RH) less than or equal to 95%.

Figure 1A:
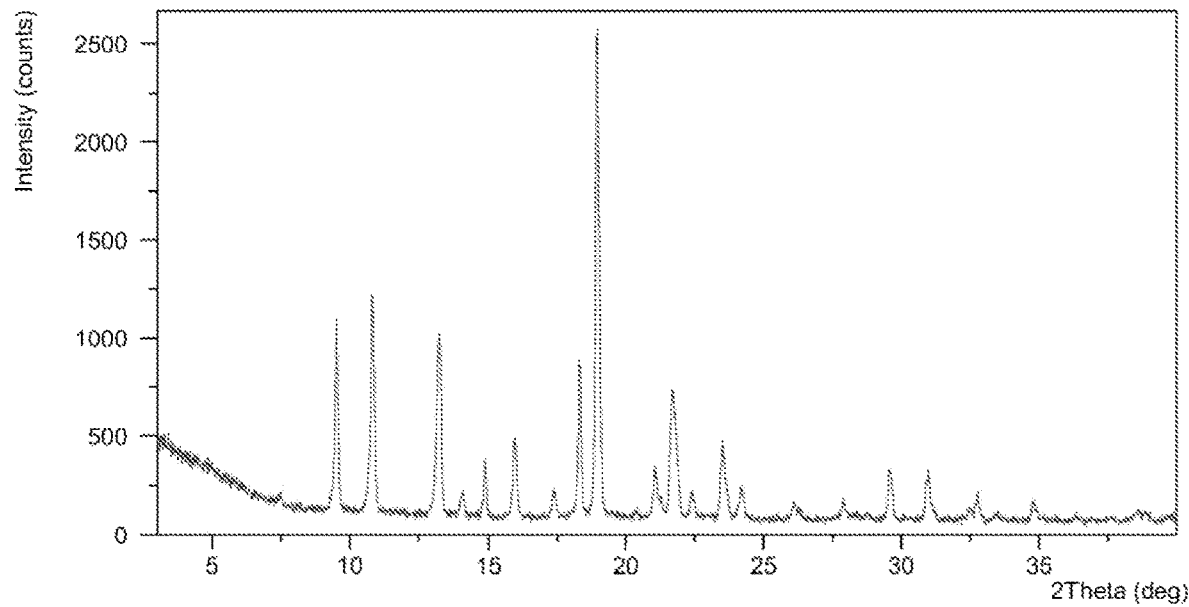
FIG. 1A depicts an exemplary XRPD pattern of Form A.

In some embodiments, Form A can have an XRPD pattern substantially as depicted in FIG. 1A. Additionally, representative peaks from the XRPD pattern of Form A can be indicated by their values of 2θ, d-spacing, and relative intensities as, for example, in Table 2 below:

TABLE 2

Selected experimental XRPD pattern data for Form A.

| 2θ (degrees) | d-spacing (Å) | Relative Intensity (%) |
|---|---|---|
| 9.494611 | 9.31518 | 40.49 |
| 10.78823 | 8.20093 | 46.5 |
| 13.22776 | 6.69345 | 37.69 |
| 14.89123 | 5.94927 | 10.18 |
| 15.99324 | 5.54174 | 15.09 |
| 18.28113 | 4.85302 | 31.96 |
| 18.93233 | 4.68754 | 100 |
| 21.05207 | 4.2201 | 10.38 |
| 21.64548 | 4.10573 | 24.16 |
| 23.50505 | 3.78495 | 15.37 |

In some embodiments, Form A has an XRPD pattern with characteristic peaks between and including the following values of 2θ in degrees: 9.3 to 9.7 (e.g., 9.5), 10.6 to 11.0 (e.g., 10.8), 13.0 to 13.4 (e.g., 13.2), 14.7 to 15.1 (e.g., 14.9), 15.8 to 16.2 (e.g., 16.0), 18.1 to 18.5 (e.g., 18.3), 18.7 to 19.1 (e.g., 18.9), 20.9 to 21.3 (e.g., 21.1), 21.4 to 21.8 (e.g., 21.6), and 23.3 to 23.7 (e.g., 23.5). In some embodiments, Form A has an XRPD pattern with characteristic peaks between and including the following values of 2θ in degrees: 9.3 to 9.7 (e.g., 9.5), 10.6 to 11.0 (e.g., 10.8), 13.0 to 13.4 (e.g., 13.2), 18.7 to 19.1 (e.g., 18.9), and 21.4 to 21.8 (e.g., 21.6). In some embodiments, Form A has an XRPD pattern with characteristic peaks at the following values of 2θ in degrees: 9.5, 10.8, 13.2, 14.9, 16.0, 18.3, 18.9, 21.1, 21.6, and 23.5. In some embodiments, Form A has an XRPD pattern with characteristic peaks at the following values of 2θ in degrees: 9.5, 10.8, 13.2, 18.9, and 21.6.

Calculated XRPD data for selected peaks can be obtained from X-ray diffraction data from a single crystal of Form A as provided in Table 3 below, which complement the experimental data in Table 2.

TABLE 3

Selected calculated XRPD pattern data for Form A.

| 2θ (degrees) | d-spacing (Å) | Relative Intensity (%) |
|---|---|---|
| 10.9265 | 8.09076 | 21.14 |
| 13.32097 | 6.64132 | 48.56 |
| 14.11329 | 6.27021 | 20.36 |
| 14.94619 | 5.92262 | 24.95 |
| 16.05232 | 5.5169 | 49.72 |
| 17.42404 | 5.08555 | 48.28 |
| 18.40825 | 4.81581 | 100 |
| 19.2493 | 4.60725 | 18.47 |
| 24.23572 | 3.66943 | 19.02 |
| 24.3725 | 3.64915 | 19.56 |

Form B

Form B can exist as a crystalline form of Compound 1 as determined by XRPD and can be prepared from various techniques described herein, e.g., slow evaporation, slurry conversion, anti-solvent addition, solid vapor diffusion, or slow cooling. Furthermore, isomorphs of Form B from different solvent systems such as dichloromethane (DCM)/n-heptane, tetrahydrofuran (THF)/n-heptane, or chloroform (CHCl$_3$)/methyl tert-butyl ether (MBTE) can be prepared. Table 4 summarizes the properties of these isomorphs as determined by various instrumental methods, e.g., TGA, DSC, and $^1$H NMR spectroscopy.

TABLE 4

Summary of exemplary isomorphs of Form B

| Isomorph | Solvent System | Crystallization Method | TGA Weight Loss (%) | $T_{onset}$ for DSC Endotherm (° C.) | Compound 1: Solvent (molar ratio) | Type of solvate |
|---|---|---|---|---|---|---|
| Form B-1 | DCM/n-heptane | Slurry conversion | 5.7 to 8.5 | 87.2, 211.7 | 1:0.4 | n-Heptane solvate |
| Form B-2 | THF/n-heptane | Anti-solvent addition | 4.6 to 8.5 | 85.4, 212.2 | 1:0.3 | n-Heptane solvate |
| Form B-3 | CHCl$_3$/MBTE | Anti-solvent addition | 10.2 | 69.2, 211.6 | 1:0.5 | CHCl$_3$ solvate |

Form C is a crystalline anhydrate of Compound 1 as determined by XRPD and can be prepared from Form A using a slurry conversion crystallization technique in isopropyl alcohol and isopropyl acetate at 50° C. TGA and single-crystal X-ray crystallography can be used to confirm the absence of solvent in Form C. DSC can be used to indicate two endotherms below 300° C.: a broad peak with a $T_{onset}$ of 183.8° C. corresponding to the transformation of Form C into Form K and a sharp peak with a $T_{onset}$ of 211.0° C. corresponding to the melting of Form K. DVS can be used to demonstrate that Form C exhibits less than 0.32 weight percent water uptake at RH less than or equal to 95%.

Figure 3A:
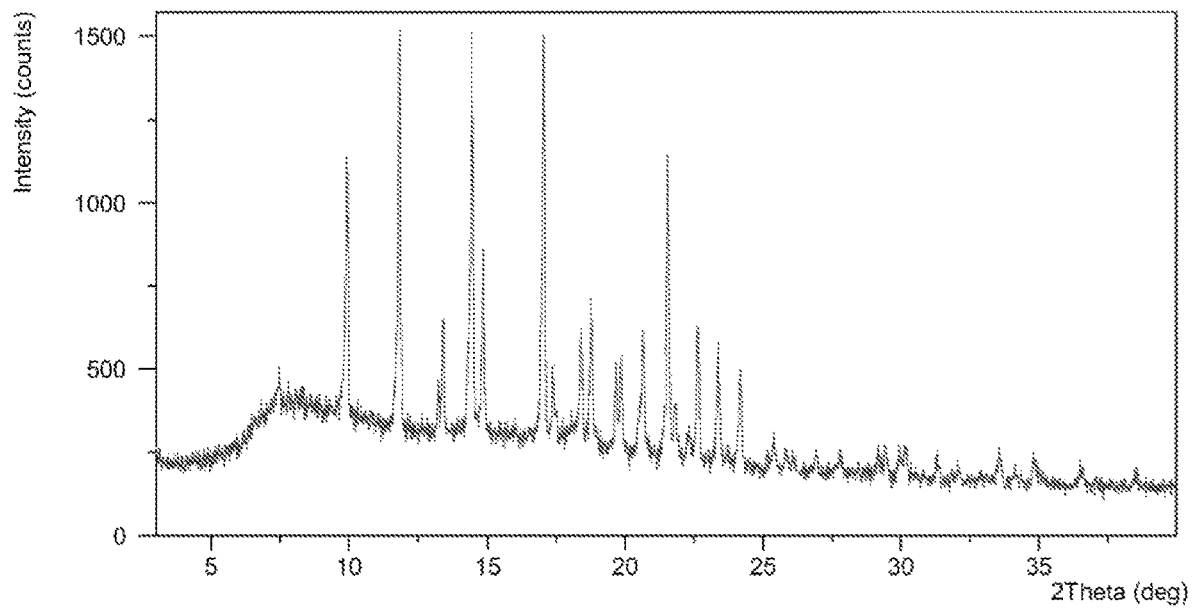
FIG. 3A depicts an exemplary XRPD pattern of Form C.

In some embodiments, Form C can have an XRPD pattern substantially as depicted in FIG. 3A. Additionally, representative peaks from the XRPD pattern of Form C can be indicated by their values of 2θ, d-spacing, and relative intensities as, for example, in Table 5 below:

TABLE 5

Selected experimental XRPD pattern data for Form C.

| 2θ (degrees) | d-spacing (Å) | Relative Intensity (%) |
|---|---|---|
| 22.60955 | 3.93279 | 26.76 |
| 20.65623 | 4.30006 | 27.84 |
| 13.36358 | 6.62573 | 28.42 |
| 14.81188 | 5.98097 | 33.78 |
| 21.50066 | 4.12963 | 36.7 |
| 21.54634 | 4.12439 | 36.94 |
| 9.889125 | 8.94443 | 41.85 |
| 11.79075 | 7.50579 | 65.73 |
| 14.41313 | 6.14552 | 65.89 |
| 16.99542 | 5.21715 | 100 |

In some embodiments, Form C can have an XRPD pattern with characteristic peaks between and including the following values of 2θ in degrees: 9.7 to 10.1 (e.g., 9.9), 11.6 to 12.0 (e.g., 11.8), 13.2 to 13.6 (e.g., 13.4), 14.2 to 14.6 (e.g., 14.4), 14.6 to 15.0 (e.g., 14.8), 16.8 to 17.2 (e.g., 17.0), 20.5 to 20.9 (e.g., 20.7), 21.3 to 21.7 (e.g., 21.5), 21.4 to 21.8 (e.g., 21.6), and 22.4 to 22.8 (e.g., 22.6). In some embodiments, Form C can have an XRPD pattern with characteristic peaks between and including the following values of 2θ in degrees: 9.7 to 10.1 (e.g., 9.9), 14.6 to 15.0 (e.g., 14.8), 16.8 to 17.2 (e.g., 17.0), 20.5 to 20.9 (e.g., 20.7), and 21.3 to 21.7 (e.g., 21.5). In some embodiments, Form C can have an XRPD pattern with characteristic peaks at the following values of 2θ in degrees: 9.9, 11.8, 13.4, 14.4, 14.8, 17.0, 20.7, 21.5, 21.6, and 22.6. In some embodiments, Form C can have an XRPD pattern with characteristic peaks at the following values of 2θ in degrees: 9.9, 14.8, 17.0, 20.7, and 21.5.

Calculated XRPD data for selected peaks can be obtained using X-ray diffraction data from a single crystal of Form C, as provided in Table 6 below. These simulated peaks can complement the experimental data in Table 5.

TABLE 6

Selected calculated XRPD pattern data for Form C.

| 2θ (degrees) | d-spacing (Å) | Relative Intensity (%) |
|---|---|---|
| 9.861923 | 8.96162 | 19.41 |
| 11.75959 | 7.51938 | 37.75 |
| 13.33554 | 6.6341 | 31.9 |
| 14.38478 | 6.15248 | 43.36 |
| 14.79021 | 5.98473 | 26.68 |
| 16.96659 | 5.22162 | 100 |
| 19.61234 | 4.52277 | 17.69 |
| 20.60123 | 4.30785 | 30.39 |
| 21.48653 | 4.13232 | 25.6 |
| 22.57956 | 3.93469 | 27.32 |

Form D

Form D can be prepared using an anti-solvent addition crystallization technique in tetrahydrofuran (THF)/water (H$_2$O) and, by XRPD analysis, can be subsequently found to be a crystalline form of Compound 1 that converted back to Form A upon drying at room temperature.

Form E

Form E can be prepared from an anti-solvent crystallization technique in 1,4-dioxane/n-heptane at room temperature and can be determined to be a crystalline wet sample of Compound 1 by XRPD.

Form F

Form F can be prepared with an anti-solvent addition crystallization technique in 1,4-dioxane/n-heptane at ambient room-temperature conditions and determined to be a crystalline form of Compound 1 by XRPD. TGA on a sample of Form F exhibits a weight loss of 19.7% up to 200° C. DSC can be used to show that Form F exhibits 2 endothermic peaks at onset temperatures of 63.1° C. and 210.7° C., corresponding to the loss of solvent (transformation to Form K) and the melting point of Form K, respectively. The transformation of Form F to Form K can be additionally confirmed through VT-XRPD measurements. Based on $^1$H NMR spectroscopy, Form F is a 1,4-dioxane solvate with a molar ratio of 1:0.9 with residual n-heptane present.

Form H

Form H can be prepared from a solution vapor diffusion crystallization technique in n-heptane at room temperature. The form was determined to be crystalline by(RFD, but metastable due to its transformation to Form A after drying at ambient conditions for 3 days.

Form I

Form I can be made using a slow cooling crystallization technique performed in methanol at room temperature. Like Form H, Form I can be determined to be a crystalline material by XRPD analysis, but was found to be metastable due to its transformation to Form A after drying at ambient conditions for 3 days.

Form J

Form J can be prepared using a solid vapor diffusion crystallization technique in methanol at room temperature. XRPD analysis can be used to conclude that Form J is a crystalline metastable sample that transforms to Form A after drying at ambient conditions for 3 days.

Form K

Form K can be prepared by heating various forms of Compound 1, e.g., Form A, Form B, Form C, Form E, and Form F, to elevated temperatures. The analyzed sample of this form can be determined to be crystalline by XRPD analysis. TGA can be used to indicate no weight loss prior to the decomposition temperature and demonstrates that Form K is anhydrous. DSC can be used to demonstrate that Form K can exhibit a single endotherm with a $T_{onset}$ of 211.6° C. that corresponds to the melting point of the analyzed sample. DVS measurements were performed to demonstrate that Form K demonstrates less than 0.35 weight percent water uptake at RH less than or equal to 95%.

Figure 10A:
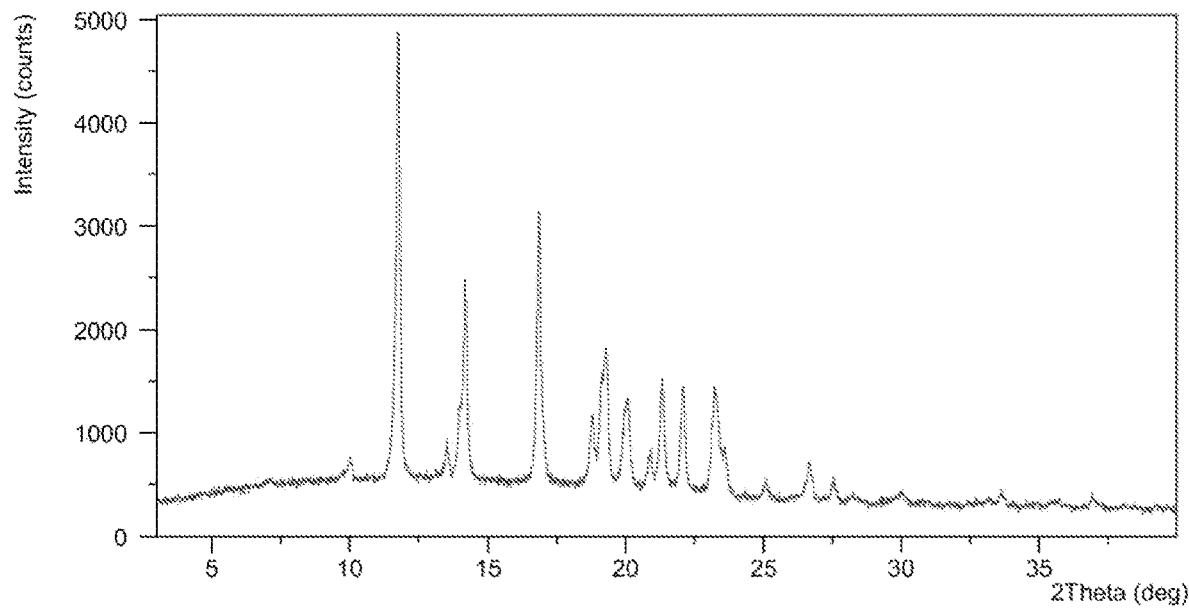
FIG. 10A depicts an exemplary XRPD pattern of Form K.

In some embodiments, Form K can have an XRPD pattern substantially as depicted in FIG. 10A. Additionally, representative peaks from the XRPD pattern of Form K can be indicated by their values of 2θ and relative intensities as, for example, in Table 7 below:

TABLE 7

Selected experimental XRPD pattern data for Form K.

| 2θ (degrees) | d-spacing (Å) | Relative Intensity (%) |
| --- | --- | --- |
| 13.9471 | 6.3498 | 19.12 |
| 20.09767 | 4.41829 | 20.68 |
| 23.20826 | 3.83268 | 23.69 |
| 22.05504 | 4.0304 | 24.27 |
| 19.10905 | 4.64459 | 24.93 |
| 21.32362 | 4.16697 | 26.68 |
| 19.33614 | 4.59055 | 28.07 |
| 14.16125 | 6.25426 | 47 |
| 16.84678 | 5.26284 | 61.56 |
| 11.75077 | 7.53124 | 100 |

In some embodiments, Form K can have an XRPD pattern with characteristic peaks between and including the following values of 2θ in degrees: 11.6 to 12.0 (e.g., 11.8), 13.7 to 14.1 (e.g., 13.9), 14.0 to 14.4 (e.g., 14.2), 16.6 to 17.0 (e.g., 16.8), 18.9 to 19.3 (e.g., 19.1), 19.1 to 19.5 (e.g., 19.3), 19.9 to 20.3 (e.g., 20.1), 21.1 to 21.5 (e.g., 21.3), 21.9 to 22.3 (e.g., 22.1), and 23.0 to 23.4 (e.g., 23.2). In some embodiments, Form K can have an XRPD pattern with characteristic peaks between and including the following values of 2θ in degrees: 11.6 to 12.0 (e.g., 11.8), 16.6 to 17.0 (e.g., 16.8), 18.9 to 19.3 (e.g., 19.1), 19.9 to 20.3 (e.g., 20.1), and 23.0 to 23.4 (e.g., 23.2). In some embodiments, Form K can have an XRPD pattern with characteristic peaks at the following values of 2θ in degrees: 11.8, 13.9, 14.2, 16.8, 19.1, 19.3, 20.1, 21.3, 22.1, and 23.2. In some embodiments, Form K can have an XRPD pattern with characteristic peaks at the following values of 2θ in degrees: 11.8, 16.8, 19.1, 20.1, and 23.2.

Form L

Form L can be prepared by storing Form B in a sealed vial at ambient conditions for one month. This form can be determined to be a crystalline metastable form of Compound 1. Analysis with XRPD can indicate that Form L transforms to a mixture of Form B and Form M at ambient conditions 3 days after preparation. Form L was determined to be a solvate of Compound 1.

Form M

Form M can be made by storing Form B in a sealed vial at ambient conditions for one month. The analyzed sample of this form was determined to have low crystallinity by analysis with XRPD.

Form N

Form N can be prepared from a reverse anti-solvent addition crystallization technique in 1,4-dioxane/n-heptane and determined to be a crystalline form of Compound 1 by XRPD. TGA can be used to determine that Form N is a solvate that exhibits a weight loss of 2.5% up to 60° C., followed by a weight loss of 7.1% up to 200° C. DSC can be used to demonstrate two endotherms, one corresponding to the loss of solvent at a $T_{onset}$ of 75.4° C. and the other at a $T_{onset}$ of 210.4° C., which represents the melting point of Form K. VT-XRPD can be used to confirm that Form N transforms to Form K at 100° C. Based on $^1$H NMR spectroscopy, Form N is a 1,4-dioxane solvate with a molar ratio of 1:0.3 for Compound 1:1,4-dioxane.

Form O

Form O can be prepared using a water activity experiment in a water/acetonitrile mixture (0.041 water:0.959 acetonitrile volume/volume; $a_w$=0.6) at room temperature and determined to be a crystalline form of Compound 1 by XRPD. TGA on a sample of Form O can indicate weight loss of 5.3% up to 55.1° C., followed by 5.9% up to 200° C. DSC can be used to show that Form O exhibits three endotherms, one at $T_{onset}$=65.0° C. corresponding to the loss of solvent to create Form C, one at $T_{onset}$=168.5° C. corresponding to transformation to Form C to Form K, and one at $T_{onset}$=210.8° C. corresponding to melting of Form K. Form O can be further characterized by $^1$H NMR spectroscopy dissolved in DMSO-$d_6$.

Form P

In addition the above-described forms, Form P is an ethyl acetate (EtOAc) solvate of Compound 1 and can be detected in (a) slurries of Form A in EtOAc at 5° C. (after 1 h) and 20° C. (after 2 days), (b) slurries of Form C in EtOAc at 5° C. (after 1 h) and 20° C. (after 7 days). The wet cake of Form P (~5 min air) can be dried in two ways: (a) under air at room temperature overnight, and (b) under vacuum at 40° C. for 3 hours. Both dried cakes can be analyzed by XRPD, $^1$H NMR, and TGA. An air dried cake of Form P can give an XRPD pattern conforming to Form P, about 1% weight loss by TGA up to about 50° C., and EtOAc peaks by $^1$H NMR. The sample of Form P post-oven drying, on the other hand, can give an XRPD pattern conforming to Form A, no weight loss ≤100° C. by TGA, and no EtOAc peaks by $^1$H NMR. Therefore, Form P can convert to Form A upon drying.

In another aspect, the present invention provides a method for transforming a solid form of Compound 1 or mixture of solid forms of Compound 1 to a different anhydrate of Compound 1. In one embodiment, Form A, a mixture of Form A or Form K, or a mixture of Form A, Form C, and Form K can be converted to Form C through slurry conversion in ethyl acetate, n-butanol, or methyl tert-butyl ether at room temperature or elevated temperatures, e.g., 50° C. or 65° C. In these 3 solvent systems, Form C is the only form remaining after slurry conversion, revealing that this solid form was more thermodynamically stable from room temperature to 50° C. when compared to Form A and Form K. In another embodiment, From C can be obtained through crystallization of solubilized Compound 1 (originally Form A) in ethyl acetate at an elevated temperature, e.g., 65° C., in the presence of a small amount, e.g. 0.2%-1.0%, of seed crystals of Form C, followed by cooling the batch to a temperature no less than 25° C. to 30° C. Seed crystals of Form C can be made using the procedure described in Example 4 described herein.

Pharmaceutical Compositions

In another aspect, the invention provides a pharmaceutical composition comprising a solid form of a compound of the present invention (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

The pharmaceutical compositions provided herein can be administered by a variety of routes including, but not limited to, oral (enteral) administration, parenteral (by injection) administration, rectal administration, topical administration, transdermal administration, intradermal administration, intrathecal administration, subcutaneous (SC) administration, intramuscular (IM) administration, sublingual/buccal, ocular, otic, vaginal, and intranasal or inhalation administration.

Generally, the solid forms of Compound 1 provided herein are administered in an effective amount. The amount of the solid forms of Compound 1 compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the onset of a CNS-disorder, the solid forms of Compound 1 provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a solid form of Compound 1 or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a consistent level of Compound 1 in the blood, e.g., within the therapeutic window over the extended period of time.

The pharmaceutical compositions of the present invention may be further delivered using a variety of dosing methods. For example, in certain embodiments, the pharmaceutical composition may be given as a bolus, e.g., in order to raise the concentration of Compound 1 in the blood to an effective level. The placement of the bolus dose depends on the systemic levels of the active ingredient desired throughout the body, e.g., an intramuscular or subcutaneous bolus dose allows a slow release of the active ingredient. Furthermore, in still yet other embodiments, the pharmaceutical composition may be administered as first as a bolus dose, followed by continuous infusion.

The compositions for oral administration can take the form of bulk liquid solutions or suspensions or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, a solid form of Compound 1 is usually a minor component (from about 0.1 to about 50% by weight or preferably from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of a solid form of Compound 1 provided herein, with preferred doses each providing from about 0.1 to about 10 mg/kg, and especially about 0.2 to about 5 mg/kg.

Transdermal doses are generally selected to provide similar or lower blood levels than are achieved using injection doses, generally in an amount ranging from about 0.01 to about 20% by weight of, e.g., the drug reservoir or drug-adhesive reservoir for the transdermal patch, preferably from about 0.1 to about 20% by weight, preferably from about 0.1 to about 10% by weight, and more preferably from about 0.5 to about 15% by weight.

Solid compositions may include, for example, any of the following ingredients, or a solid form of Compound 1 of a similar nature: binders, surfactants, diluents or fillers, buffering agents, antiadherents, glidants, hydrophilic or hydrophobic polymers, retardants, stabilizing agents or stabilizers, disintegrants or superdisintegrants, dispersants, antioxidants, antifoaming agents, fillers, flavors, colorants, lubricants, sorbents, preservatives, plasticizers, coatings, or sweeteners, or mixtures thereof, For example, the exipeint or excipients could be a binder such as microcrystalline cellulose, polyvinyl pyrrolidone, hydroxylpropyl cellulose, low viscosity hydroxypropylmethylcellulose, gum tragacanth or gelatin; a diluent such as mannitol, microcrystalline cellulose, maltodextrin, starch or lactose, a disintegrating agent such as alginic acid, Primogel, sodium starch glycolate, sodium croscarmellose, crospovidone, or corn starch; a lubricant such as magnesium stearate, sodium stearyl fumarate or glyceryl behenate; a glidant such as colloidal silicon dioxide; a preservative such as potassium sorbate or methyl paraben, asurfactant, such as sodium lauryl sulfate, sodium docusate, poysorbate 20, polysorbate 80, cetyl triethyl ammonium bromide, polyethylene oxide-polypropylene oxide copolymers, or Cremophor EL. an antioxidant such as butylhydroxy toluene, butyl hydroxyanisole, propyl gallate, ascorbic acid, tocopherol or tocopherol acetate, sodium sulphite, or sodium metabisulfite, a coating comprising one or more of hydroxypropykmethylcellulose, polyvinyl alcohol, methacrylate copolymers, cellulose acetate, hydroxypropylmethylcellulose acetate succinate, shellac and others, a sweetening agent such as sucrose, sucralose, acesulfame K, sodium aspartame or saccharin; or a flavoring agent such as peppermint, methyl salicylate, or orange flavoring. Any of the well known pharmaceutical excipients may be incorporated in the dosage form and may be found in the FDA's Inactive Ingredients Guide, Remington: The Science and Practice of Pharmacy, Twenty-first Ed., (Pharmaceutical Press, 2005); Handbook of Pharmaceutical Excipients, Sixth Ed. (Pharmacrutical Press, 2009) all of which are incorporated by reference.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration and stability of the active ingredients or Formulation. All such known transdermal formulations and ingredients are included within the scope provided herein. Topical delivery compositions of interest include liquid formulations, such as lotions (liquids containing insoluble material in the form of a suspension or emulsion, intended for external application, including spray lotions) and aqueous solutions, semi-solid formulations, such as gels (colloids in which the disperse phase has combined with the dispersion medium to produce a semisolid material, such as a jelly), creams (soft solids or thick liquids) and ointments (soft, unctuous preparations), and solid formulations, such as topical patches. As such, delivery vehicle components of interest include, but are not limited to: emulsions of the oil-in-water (O/W) and the water in-oil (W/O) type, milk preparations, lotions, creams, ointments, gels, serum, powders, masks, packs, sprays, aerosols, sticks, and patches.

The solid forms of Compound 1 provided herein can also be administered by a transdermal device. Accordingly, transdermal administration can be accomplished using a patch either of the reservoir or membrane type, or of an adhesive matrix or other matrix variety. Delivery compositions of interest include liquid formulations, such as lotions (liquids containing insoluble material in the form of a suspension or emulsion, intended for external application, including spray lotions) and aqueous solutions, semi-solid formulations, such as gels (colloids in which the disperse phase has combined with the dispersion medium to produce a semisolid material, such as a jelly), creams (soft solids or thick liquids) and ointments (soft, unctuous preparations), and solid formulations, such as topical patches. As such, delivery vehicle components of interest include, but are not limited to: emulsions of the oil-in-water (O/W) and the water in-oil (W/O) type, milk preparations, lotions, creams, ointments, gels, serum, powders, masks, packs, sprays, aerosols, sticks, and patches. For a transdermal patch, the active agent layer includes one or more active agents, one of which is Compound I. In certain embodiments, the matrix is an adhesive matrix. The matrix may include polymeric materials. Suitable polymers for the adhesive matrix include, but are not limited to: polyurethanes, acrylates, styrenic block copolymers, silicones, and the like. For example, the adhesive matrix may include, but is not limited to, an acrylate polymer, polysiloxanes, polyisobutylene (PM), polyisoprene, polybutadiene, styrenic block polymers, combinations of thereof, and the like. Additional examples of adhesives are described in Satas, "Acrylic Adhesives," Handbook of Pressure-Sensitive Adhesive Technology, 2nd ed., pp. 396-456 (D. Satas, ed.), Van Nostrand Reinhold, New York (1989), the disclosure of which is herein incorporated by reference.

In certain embodiments, the active agent layer includes a permeation enhancer. The permeation enhancer may include, but is not limited to the following: aliphatic alcohols, such as but not limited to saturated or unsaturated higher alcohols having 12 to 22 carbon atoms, such as oleyl alcohol and lauryl alcohol; fatty acids, such as but not limited to linolic acid, oleic acid, linolenic acid, stearic acid, isostearic acid and palmitic acid; fatty acid esters, such as but not limited to isopropyl myristate, diisopropyl adipate, and isopropyl palmitate; alcohol amines, such as but not limited to triethanolamine, triethanolamine hydrochloride, and diisopropanolamine; polyhydric alcohol alkyl ethers, such as but not limited to alkyl ethers of polyhydric alcohols such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, isosorbide, methyl glucoside, oligosaccharides, and reducing oligosaccharides, where the number of carbon atoms of the alkyl group moiety in the polyhydric alcohol alkyl ethers is preferably 6 to 20; polyoxyethylene alkyl ethers, such as but not limited to polyoxyethylene alkyl ethers in which the number of carbon atoms of the alkyl group moiety is 6 to 20, and the number of repeating units (e.g. —$OCH_2CH_2$—) of the polyoxyethylene chain is 1 to 9, such as but not limited to polyoxyethylene lauryl ether, polyoxyethylene cetyl ether, polyoxyethylene stearyl ether, and polyoxyethylene oleyl ether; glycerides (i.e., fatty acid esters of glycerol), such as but not limited to glycerol esters of fatty acids having 6 to 18 carbon atoms, diglycerides, triglycerides or combinations thereof. In some embodiments, the polymer matrix includes a polyvinylpyrrolidone, The composition may further include one or more fillers or one or more antioxidants. In some embodiments, the transdermal formulations described may have a multi-layer structure. For example, the transdermal formulation may have an adhesive matrix and a backing.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

A solid form of Compound 1 of the present invention can also be administered in sustained release forms or from sustained release drug delivery systems. A description of representative sustained release materials can be found in Remington's Pharmaceutical Sciences.

Methods of Use

Provided herein are methods of treating a disorder, e.g., a CNS-related disorder, in a subject in need thereof, comprising administering to the subject an effective amount of Compound 1, e.g., Compound 1 as a solid form described herein, or a pharmaceutically acceptable salt or pharmaceutical composition thereof. In certain embodiments, the disorder is a CNS-related disorder selected from the group consisting of a sleep disorder, a mood disorder, a schizophrenia spectrum disorder, a convulsive disorder, a disorder of memory and/or cognition, a movement disorder, a personality disorder, autism spectrum disorder, pain, traumatic brain injury, a vascular disease, a substance abuse disorder and/or withdrawal syndrome, and tinnitus. In some embodiments, the disorder is a comorbid disorder (e.g., depression comorbid with a personality disorder or a sleep disorder comorbid with a personality disorder). In some embodiments, the disorder is a neurological disorder as described herein. In some embodiments, the disorder is a neurological disorder as described herein. In some embodiments, the disorder is a psychiatric disorder as described herein. In some embodiments, the disorder is a seizure disorder as described herein. In some embodiments, the disorder is a neuroinflammatory disorder as described herein. In some embodiments, the disorder is a glaucoma or metabolic disorder as described herein. In some embodiments, the disorder is a sensory deficit disorder as described herein. Also provided herein are methods of using Compound 1, e.g., Compound 1 as a solid form described herein, or a pharmaceutically acceptable salt or pharmaceutical composition thereof, as a neuroprotectant. Also provided herein are methods of using Compound 1, e.g., Compound 1 as a solid form described herein, or a pharmaceutically acceptable salt or pharmaceutical composition thereof, as an analgesic or other agent for pain control.

Neurological Disorders

A solid form of Compound 1, or a pharmaceutically acceptable composition thereof, can be used in a method described herein, for example in the treatment of a disorder described herein such as a neurological disorder. Exemplary neurological disorders include, but are not limited to, neurodegenerative disorders, neurodevelopmental disorders, neuroendocrine disorders and dysfunction, movement disorders, and sleep disorders as described herein.

Neurodegenerative Disorders

A solid form of Compound 1, or a pharmaceutically acceptable composition thereof, can be used in a method described herein, for example in the treatment of a neurodegenerative disorder.

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; fragile X syndrome; Gilles de la Tourette's syndrome; head trauma; hearing impairment and loss; Huntington's disease; Lennox syndrome; mental retardation; neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Neurodevelopmental Disorders

A solid form of Compound 1, or a pharmaceutically acceptable composition thereof, can be used in a method described herein, for example in the treatment of a disorder described herein such as a neurodevelopmental disorder. In some embodiments, the neurodevelopmental disorders is autism spectrum disorder. In some embodiments, the neurodevelopmental disorder is Smith-Lemli-Opitz syndrome.

Neuroendocrine Disorders

Provided herein are methods that can be used for treating neuroendocrine disorders and dysfunction. As used herein, "neuroendocrine disorder" or "neuroendocrine dysfunction" refers to a variety of conditions caused by imbalances in the body's hormone production directly related to the brain. Neuroendocrine disorders involve interactions between the nervous system and the endocrine system. Because the hypothalamus and the pituitary gland are two areas of the brain that regulate the production of hormones, damage to the hypothalamus or pituitary gland, e.g., by traumatic brain injury, may impact the production of hormones and other neuroendocrine functions of the brain. In some embodiments, the neuroendocrine disorder or dysfunction is associated with a women's health disorder or condition (e.g., a women's health disorder or condition described herein). In some embodiments, the neuroendocrine disorder or dysfunction is associated with a women's health disorder or condition is polycystic ovary syndrome.

Symptoms of neuroendocrine disorder include, but are not limited to, behavioral, emotional, and sleep-related symptoms, symptoms related to reproductive function, and somatic symptoms; including but not limited to fatigue, poor memory, anxiety, depression, weight gain or loss, emotional lability, lack of concentration, attention difficulties, loss of libido, infertility, amenorrhea, loss of muscle mass, increased belly body fat, low blood pressure, reduced heart rate, hair loss, anemia, constipation, cold intolerance, and dry skin.

Movement Disorders

A solid form of Compound 1, or a pharmaceutically acceptable composition thereof, can be used in a method described herein, for example in the treatment of a movement disorder. In some embodiments, the movement disorder is essential Tremor, Stiff-Person syndrome, spasticity, Freidrich's ataxia, Cerebellar ataxia, dystonia, Tourette Syndrome, Fragile X-associated tremor or ataxia syndromes, drug-induced or medication-induced Parkinsonism (such as neuroleptic-induced acute akathisia, acute dystonia, Parkinsonism, or tardive dyskinesia, neuroleptic malignant syndrome, or medication-induced postural tremor), ataxia, cerebellar ataxia including McLeod neuroacanthocytosis syndrome (MLS), levodopa-induced dyskinesia, movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor), or dystonia (including axial dystonia, dystonic writer's cramp, hemiplegic dystonia, paroxysmal dystonia, and focal dystonia such as blepharospasm, oromandibular dystonia, and spasmodic dysphonia and torticollis).

As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor

The methods described herein can be used to treat tremor, for example Compound 1, e.g., a solid form of Compound 1, or a pharmaceutically acceptable salt or composition thereof, can be used to treat cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyoid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor.

Tremor is an involuntary, at times rhythmic, muscle contraction and relaxation that can involve oscillations or twitching of one or more body parts (e.g., hands, arms, eyes, face, head, vocal folds, trunk, legs).

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawl, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myloclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part.

Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Sleep Disorders

A solid form of Compound 1, or a pharmaceutically acceptable composition thereof, can be used in a method described herein, for example in the treatment of a sleep disorder. In some embodiments, the sleep disorder is comorbid with another disorder (e.g., a sleep disorder comorbid with a personality disorder).

Psychiatric Disorders

A solid form of Compound 1, or a pharmaceutically acceptable composition thereof, can be used in a method described herein, for example in the treatment of a disorder described herein such as a psychiatric disorder. Exemplary psychiatric disorders include, but are not limited to, mood disorders, anxiety disorders, psychotic disorders, and impulse control disorders as described herein.

Mood Disorders

Also provided herein are methods for treating a mood disorder, for example, clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, comorbid depression, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporous, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness. Mood disorder associated with conditions or disorders of women's health refers to mood disorders (e.g., depression) associated with (e.g., resulting from) a condition or disorder of women's health (e.g., as described herein).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Depression or personality disorders may also be comorbid with another disorder. For example, depression may be comorbid with a personality disorder. In another example, a personality disorder may be comorbid with a sleep disorder.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

Anxiety Disorders

Provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Psychotic Disorders

A solid form of Compound 1, or a pharmaceutically acceptable composition thereof, can be used in a method described herein, for example in the treatment of a psychotic disorder. In some embodiments, the impulse control disorder is schizophrenia or bipolar disorder. In some embodiments, the psychotic disorder is schizophrenia. In some embodiments, the psychotic disorder is bipolar disorder.

Bipolar disorder or manic depressive disorder causes extreme mood swings that include emotional highs (mania or hypomania) and lows (depression).

Impulse Control Disorders

A solid form of Compound 1, or a pharmaceutically acceptable composition thereof, can be used in a method described herein, for example in the treatment of an impulse control disorder. In some embodiments, the impulse control disorder is anorexia nervosa or alcohol withdrawal. In some embodiments, the impulse control disorder is anorexia nervosa. In some embodiments, the impulse control disorder is anorexia nervosa.

Seizure Disorders

A solid form of Compound 1, or a pharmaceutically acceptable composition thereof, can be used in a method described herein, for example in the treatment of a seizure disorder. In some embodiments, the seizure disorder is epilepsy. In some embodiments, the seizure disorder is status epilepticus, e.g., convulsive status epilepticus, e.g., early status epilepticus, established status epilepticus, refractory status epilepticus, or super-refractory status epilepticus. In some embodiments, the seizure disorder is a focal seizure with either motor (automatisms, atonic, clonic, epileptic spasms, hyperkinetic, myoclonic, and tonic) or non-motor (autonomic, behavioral arrest, cognition, emotional, and sensory) onset, a generalized seizure with either motor (tonic-clonic, clonic, myoclonic, myoclonic-tonic-clonic, myoclonic-atonic, atonic, epileptic spasms) or non-motor (absence) onset, a seizure with unknown motor (tonic-clonic, epileptic spasms) or non-motor (behavioral arrest) onset, a seizure associated with clinical syndromes, such as Dravet syndrome, Rett syndrome, Lennox Gasteau syndrome, Tuberous sclerosis, Angelmans syndrome, catamenial epilepsy. In some embodiments, the seizure disorder is a seizure that is caused by schizoaffective disorder or by drugs used to treat schizophrenia.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grand-mal seizures on awakening, West syndrome, Lennox-Gastaut syndrome, partial epilepsy, e.g., temporal lobe epilepsy, frontal lobe epilepsy, benign focal epilepsy of childhood.

Status Epilepticus (SE)

Status epilepticus (SE) can include, e.g., convulsive status epilepticus, e.g., early status epilepticus, established status epilepticus, refractory status epilepticus, or super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

Neuroinflammatory Disorders

A solid form of Compound 1, or a pharmaceutically acceptable composition thereof, can be used in a method described herein, for example in the treatment of a disorder described herein such as a neuroinflammatory disorder. In some embodiments, the neuroinflammatory disorder is multiple sclerosis or a pediatric autoimmune neuropsychiatric disorder associated with a streptococcal infection (PANDAS).

Analgesia/Pain Control

A solid form of Compound 1, or a pharmaceutically acceptable composition thereof, can be used in a method described herein, for example as an analgesic or other agent for pain control. In some embodiments, a solid form of Compound 1, or a pharmaceutically acceptable composition thereof, can be used as an analgesic or other agent for pain control to treat inflammatory pain, neuropathic pain, fibromyalgia, or peripheral neuropathy.

Sensory Deficit Disorders

A solid form of Compound 1, or a pharmaceutically acceptable composition thereof, can be used in a method described herein, for example in the treatment of a disorder described herein such as a sensory deficit disorder. In some embodiments, the sensory deficit disorder is tinnitus or synesthesia. In some embodiments, the sensory deficit disorder is hearing impairment and/or loss.

EXAMPLES

In order that the invention described herein may be more fully understood, the following examples are set forth. The examples described in this application are offered to illustrate the crystalline solid forms provided herein and are not to be construed in any way as limiting their scope.

Example 1. Preparation of Solid Form A

Form A was prepared by stirring crude Compound 1 as a slurry in ethyl acetate below 10° C. and then filtering and drying under vacuum. It was also formed by dissolving crude Compound 1 in dichloromethane and then re-concentrating the solution twice with ethyl acetate under vacuum to dryness.

Example 2. Various Wet Methods of Crystallization to Obtain Other Solid Forms of the Present Invention To find new crystalline forms, different crystallization methods were evaluated using Form A as the starting material. In addition to Form A, thirteen crystalline forms (B, C, D, E, F, H, I, J, K, L, M, N, and O) were identified with these methods.

Slow Evaporation

Slow evaporation crystallization experiments were performed across 8 different solvent systems. In each experiment approximately 10 mg of Form A was dissolved in 0.4 to 1.0 mL of solvent in a 1.5 mL glass vial. The glass vials were sealed using PARAFILM® (wax-blended polyolefin film) pierced with 3 to 5 holes to allow for solvent evaporation.

Slurry Conversion

In each experiment, approximately 10 to 20 mg of Form A was suspended in 0.5 mL of a solvent or mixture of solvents. After stirring at RT or 50° C. for 48 hours, the solids were isolated by centrifugation for analysis (wet sample). If the suspensions turned into clear solution, the clear solutions were kept at ambient conditions for slow evaporation.

Anti-Solvent Addition

In each experiment, approximately 10 mg of Form A was dissolved in 0.1 to 1 mL of each solvent to obtain a clear solution. The anti-solvent was added in increments of 50 µL until precipitation was observed, or the total volume of anti-solvent reached 20 times that of the solvent volume. The precipitate was then isolated by centrifugation for analysis (wet sample). In the instances that clear solutions were observed, slow evaporation experiments were performed.

Slow-Cooling

In each experiment, approximately 10 mg of Form A was suspended in 0.8 to 1.0 mL of each solvent mixture at 50° C. The resulting suspensions were immediately filtered with a 0.2 µm filter, and the filtrates were collected and cooled from 50° C. to 5° C. at a rate of 0.1° C./min. The precipitates were then isolated by centrifugation at 10,000 rpm for 3 to 5 minutes for analysis (wet sample).

Solution Vapor Diffusion

In each experiment, approximately 10 mg of Form A was dissolved in an appropriate solvent to obtain a clear solution in a 3-mL glass vial. The vial was then placed into a 20-mL glass vial containing 3 mL of the anti-solvent and sealed. The system was kept at RT for 7 days, allowing sufficient time for solid precipitation. The solids were isolated by centrifugation at 10,000 rpm for 3 to 5 minutes and analyzed (wet sample). In the cases where no precipitation was observed, the samples were kept at ambient conditions for slow evaporation.

Solid Vapor Diffusion

In each experiment, approximately 10 mg of Form A was placed into a 3-mL glass vial, which was then sealed into a 20-mL glass vial containing 3 mL of the specific solvent. The system was kept at RT for 7 days, allowing sufficient time for organic vapor to interact with the solids. The solids were then analyzed (wet sample).

Fast Evaporation

In each experiment, approximately 10 mg of Form A was dissolved in 0.5 to 1.0 mL of each solvent in a 1.5-mL glass vial. The visually clear solutions were kept at ambient conditions for fast evaporation with the lid off. The solids obtained via evaporation were then analyzed (dry sample).

Reverse Anti-Solvent Addition

In each experiment, approximately 20 mg of Form A was dissolved in 0.2 to 0.6 mL of each solvent to obtain a clear solution. The solution was added to a glass vial containing 2.0 mL of each anti-solvent at RT conditions. The precipitate formed was centrifuged at 10,000 rpm for 3 to 5 minutes for analysis (wet sample). In the cases where no precipitation was observed, slow evaporation experiments were conducted for the remaining solutions.

Water Activity Experiments

Water activity experiments, ranging from 0 to 1 water activity ($a_w$) at 0.2 intervals, were performed with $H_2O$ and acetonitrile. About 10 mg of Form A was weighed into 1.5 mL vials and 0.5 mL of the solvent mixture was added. The suspension was stirred at a rate of 1000 rpm at room temperature. The residual solvent was removed from the sample by centrifugation (10000 rpm for 3 min).

Example 3. Preparation of Solid Form B

Form B was prepared via slow evaporation, slurry conversion in a dichloromethane (DCM)/n-heptane solvent system, anti-solvent addition, solid vapor diffusion, and slow cooling crystallization techniques in a variety of solvent systems. Isomorphs of Form B characterized in the present invention were obtained from the slurry conversion technique in dichloromethane (DCM)/n-heptane and an anti-solvent addition technique in tetrahydrofuran (THF)/n-heptane or chloroform (CHCl$_3$)/methyl tert-butyl ether (MBTE).

Example 4. Preparation of Solid Form C

Form C was prepared from Form A via a slurry conversion crystallization technique in isopropyl alcohol (IPA) and isopropyl acetate (IPAc) at 50° C.

Example 5. Preparation of Solid Form D

Form D was prepared from Form A via an anti-solvent addition crystallization technique in tetrahydrofuran (THF)/water (H$_2$O) at room-temperature (RT) conditions.

Example 6. Preparation of Solid Form E

Form E was prepared from Form A via an anti-solvent addition crystallization technique in 1,4-dioxane/n-heptane at ambient room-temperature (RT) conditions.

Example 7. Preparation of Solid Form F

Form F was prepared from Form A via a reverse anti-solvent addition crystallization technique in 1,4-dioxane/n-heptane at ambient room-temperature (RT) conditions.

Example 8. Preparation of Solid Form H

Form H was prepared via a solution vapor diffusion crystallization technique in n-heptane at room-temperature (RT) conditions.

Example 9. Preparation of Solid Form I

Form I was prepared via a slow cooling crystallization technique in methanol (MeOH) at room-temperature (RT) conditions.

Example 10. Preparation of Solid Form J

Form J was prepared via a solid vapor diffusion crystallization technique in MeOH at room-temperature (RT) conditions.

Example 11. Preparation of Solid Form K

Form K was prepared by heating Forms A, B, C, E, or F to elevated temperatures. The sample of Form K analyzed was prepared by heating Form F to 100° C.

Example 12. Preparation of Solid Form L

Form L was prepared by storing Form B in a sealed vial at ambient conditions for a month.

Example 13. Preparation of Solid Form M

Form M was prepared by storing Form B in a sealed vial at ambient conditions for a month.

Example 14. Preparation of Solid Form N

Form N was prepared from a reverse anti-solvent addition crystallization technique in 1,4-dioxane/n-heptane when attempting to replicate formation of Form F.

Example 15. Preparation of Solid Form O

Form O was prepared from a water activity crystallization technique in H$_2$O/acetonitrile (ACN) (0.041:0.959 v/v; a$_w$=0.6). Acetonitrile plays an essential role in Form O formation, and this solvent may be needed to produce this form.

Example 16. Characterization of Solid Forms A-O by XRPD

A PANalytical Empyrean X-ray powder diffractometer with a 12-well auto-sampler stage was used for analysis throughout this study. The XRPD parameters used are listed in Table 8. Resolution calibration of the instrument was performed every 6 months, and sensitivity measurements were performed after the sample stage was changed. A silicon (Si) pressed powder sample was used as the reference standard.

TABLE 8

| Parameters for XRPD | |
|---|---|
| | Parameters for Reflection Mode |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (degrees 2θ) | 3° to 40° |
| Step size (degrees 2θ) | 0.017° |
| Scan speed (degrees/min) | ~10 |

Form A: Form A was observed to be crystalline by XRPD, as shown in FIG. 1A.

Figure 2A:
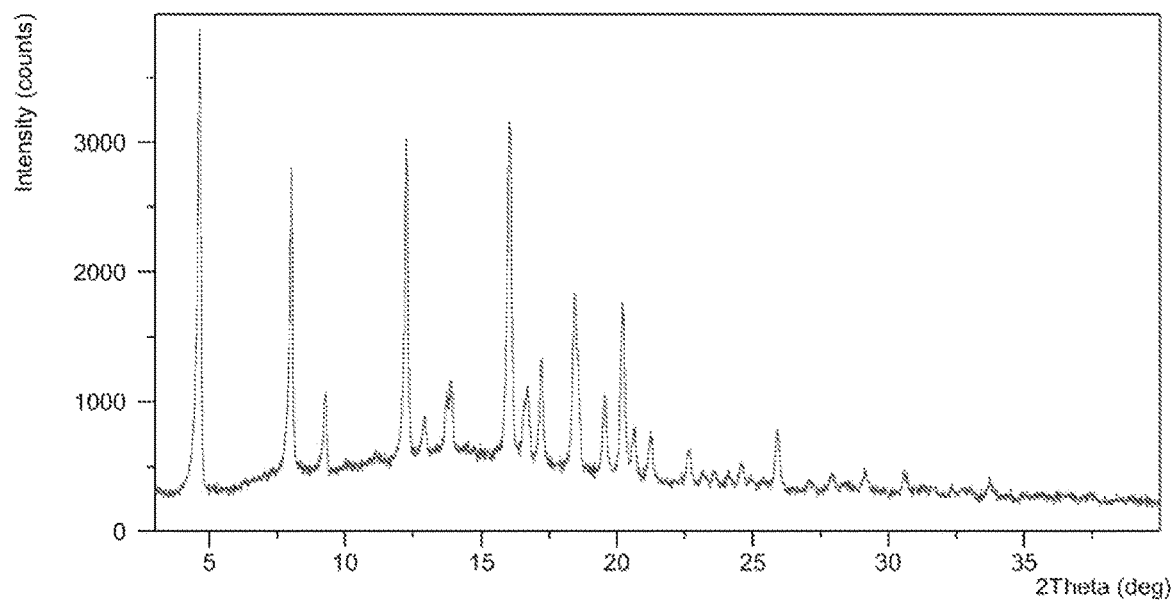
FIG. 2A depicts an exemplary XRPD pattern of an isomorph of Form B.
Figure 2B:
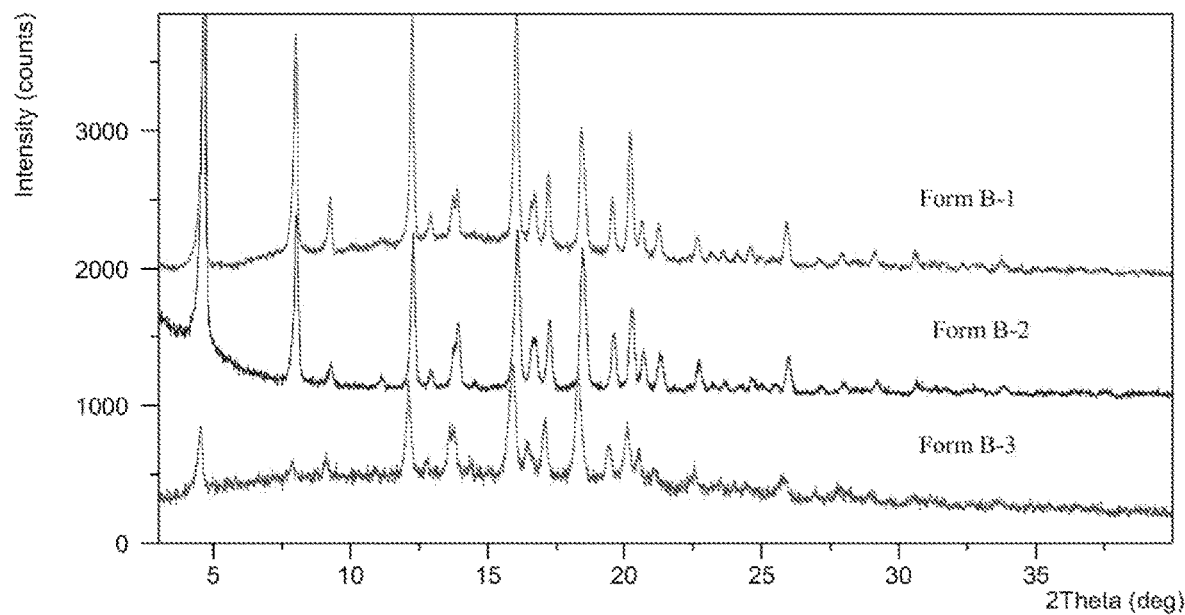
FIG. 2B depicts exemplary XRPD patterns of three isomorphs of Form B.

Form B: The XRPD pattern in FIG. 2A shows that Form B-1 is crystalline. The XRPD patterns in FIG. 2B shows that Forms B-1, B-2, and B-3 are crystalline.

Form C: The XRPD pattern in FIG. 3A shows that Form C is crystalline.

Figure 4A:
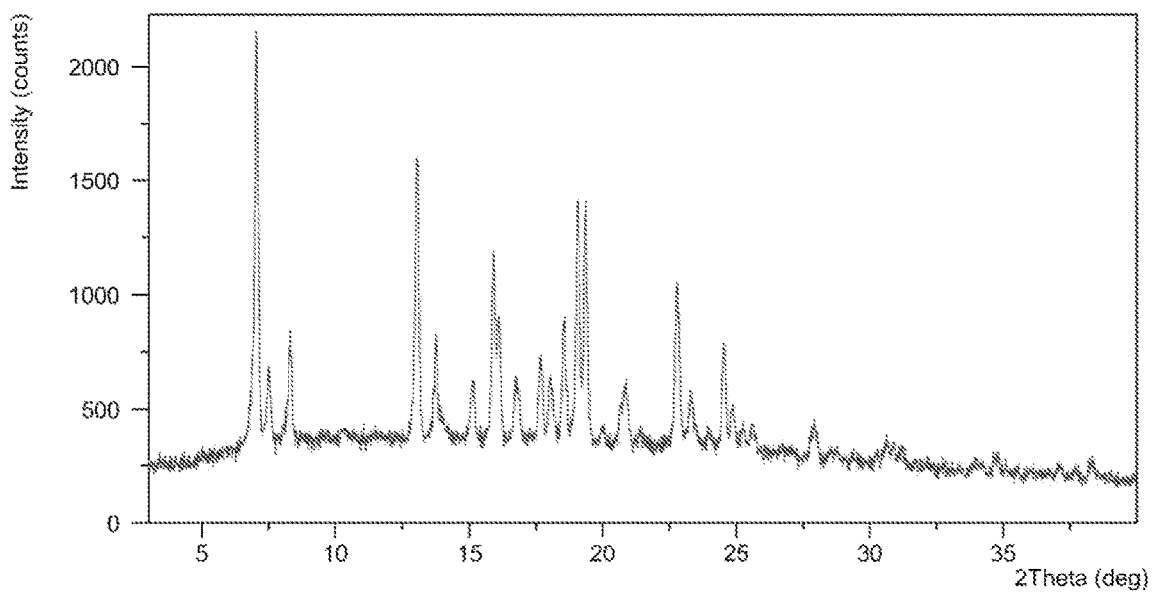
FIG. 4A depicts an exemplary XRPD pattern of Form D.
Figure 4B:
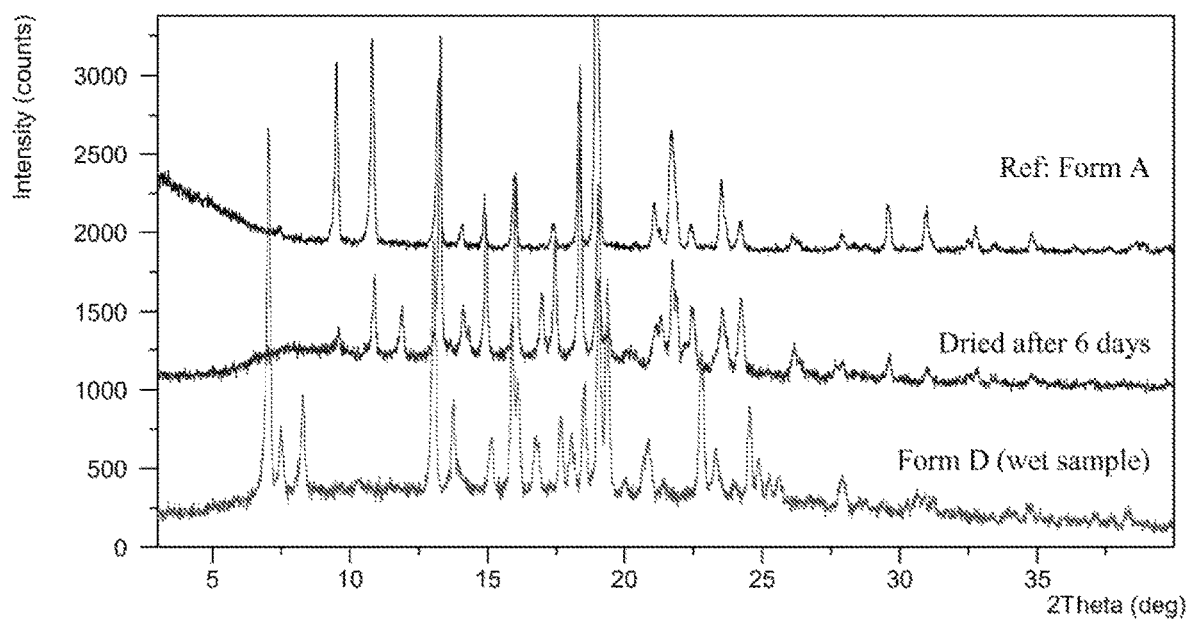
FIG. 4B depicts an overlay of exemplary XRPD patterns of Form D before and after drying at ambient conditions, along with an exemplary XRPD pattern of Form A.

Form D: As shown in the obtained XRPD pattern provided in FIG. 4A, Form D is crystalline. XRPD analysis also indicated that Form D was transformed to Form A after drying at ambient conditions, as illustrated in FIG. 4B.

Figure 5:
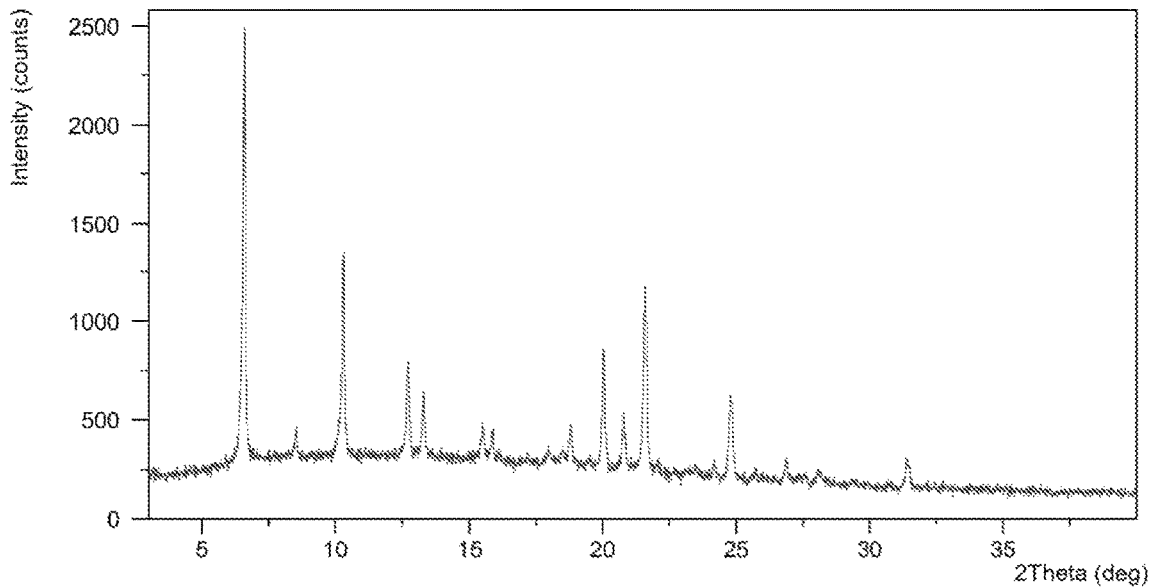
FIG. 5 depicts an exemplary XRPD pattern of Form E.

Form E: Based on the obtained XRPD pattern of the wet sample in FIG. 5. Form E was observed to be crystalline. After drying at ambient room-temperature conditions, Form E transformed to a poorly crystalline mixture of Forms A and C.

Figure 6A:
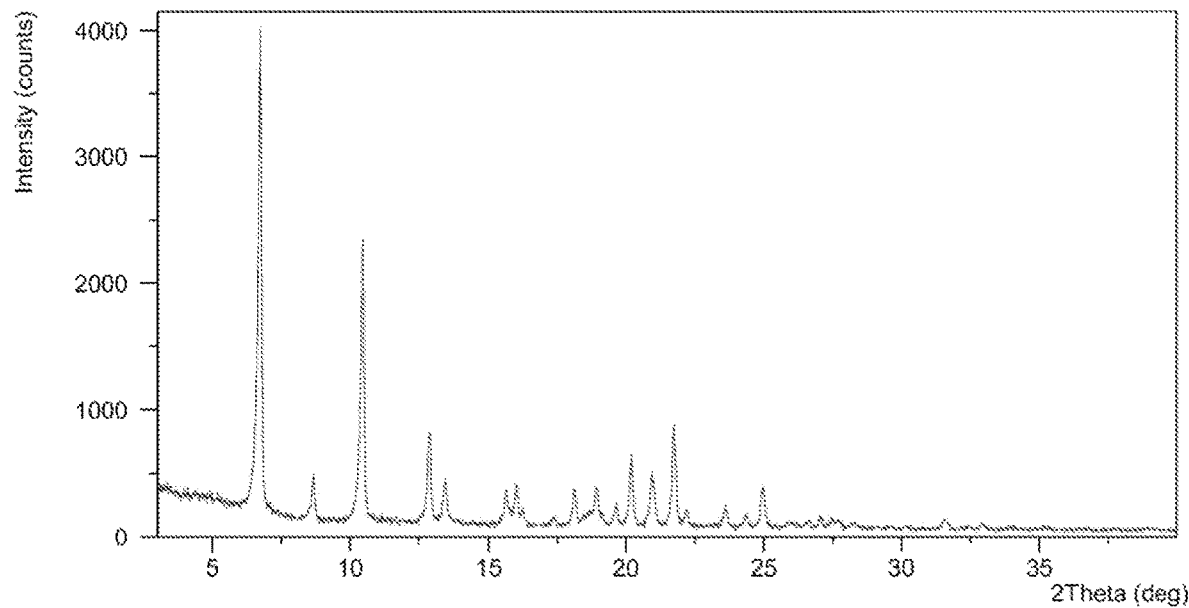
FIG. 6A depicts an exemplary XRPD pattern of Form F.

Form F: The obtained XRPD pattern of the dried sample under vacuum in FIG. 6A shows that Form F is crystalline.

Figure 7A:
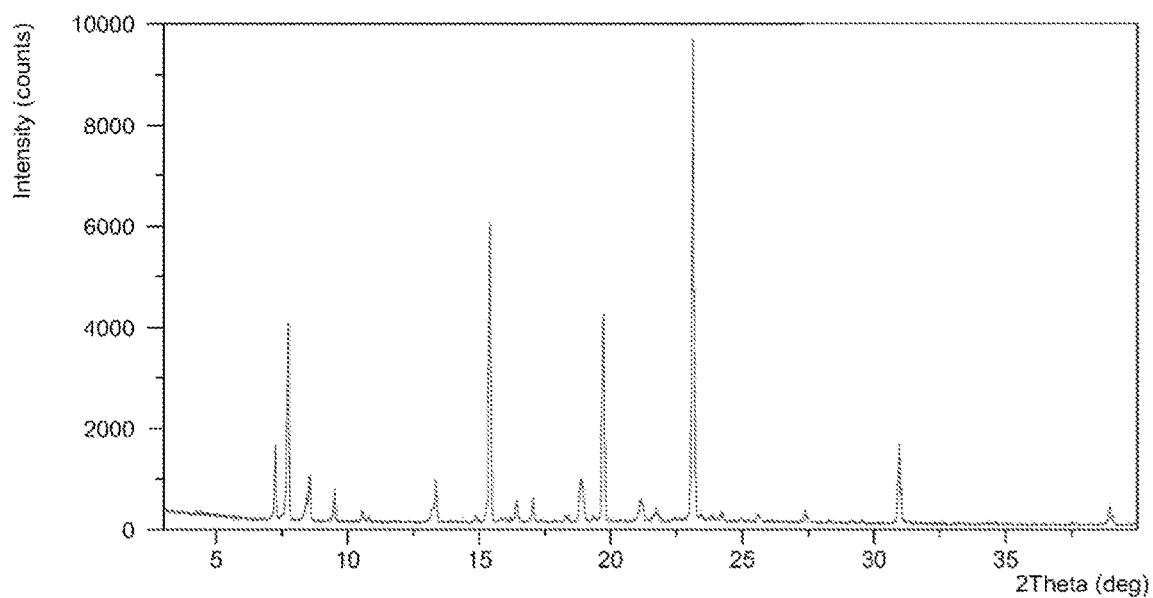
FIG. 7A depicts an exemplary XRPD pattern of Form H.
Figure 7B:
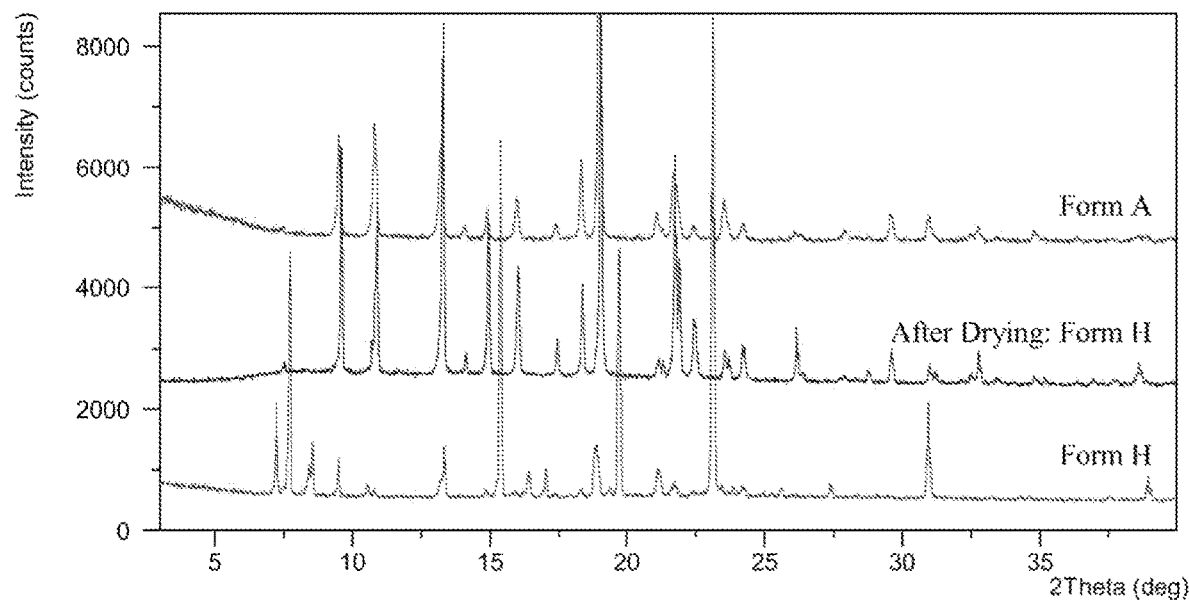
FIG. 7B depicts an overlay of exemplary XRPD patterns of Form H before and after drying at ambient conditions and an exemplary XRPD pattern of Form A.

Form H: The obtained XRPD pattern of the wet sample in FIG. 7A shows that Form H is crystalline. XRPD analysis indicates that Form H transforms to Form A after drying at ambient conditions for 3 days, as illustrated in FIG. 7B.

Figure 8A:
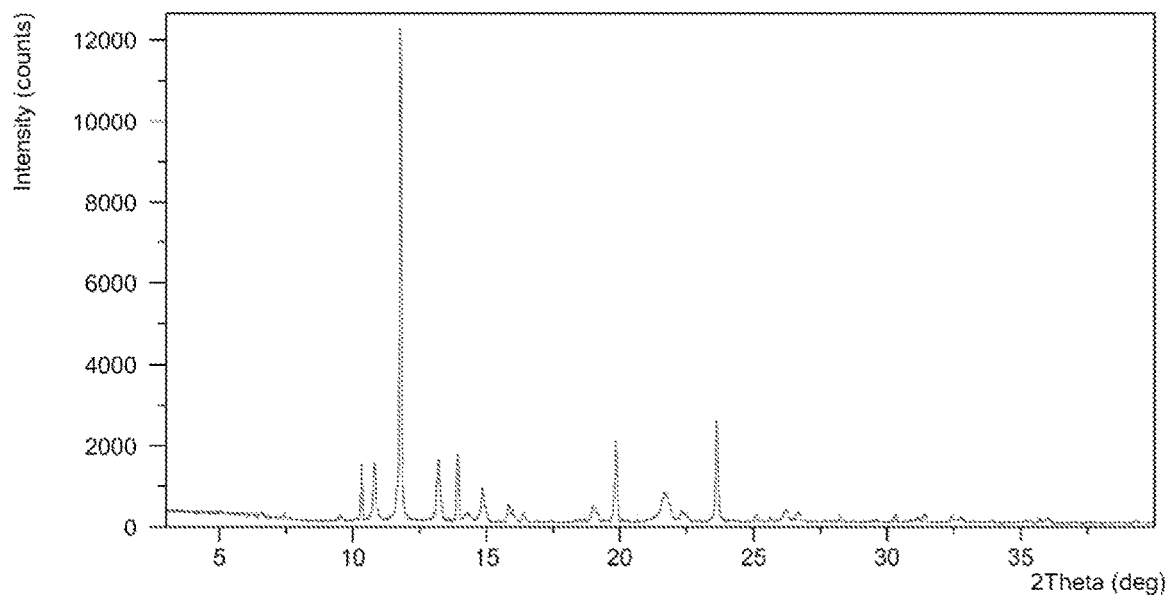
FIG. 8A depicts an exemplary XRPD pattern of Form I.
Figure 8B:
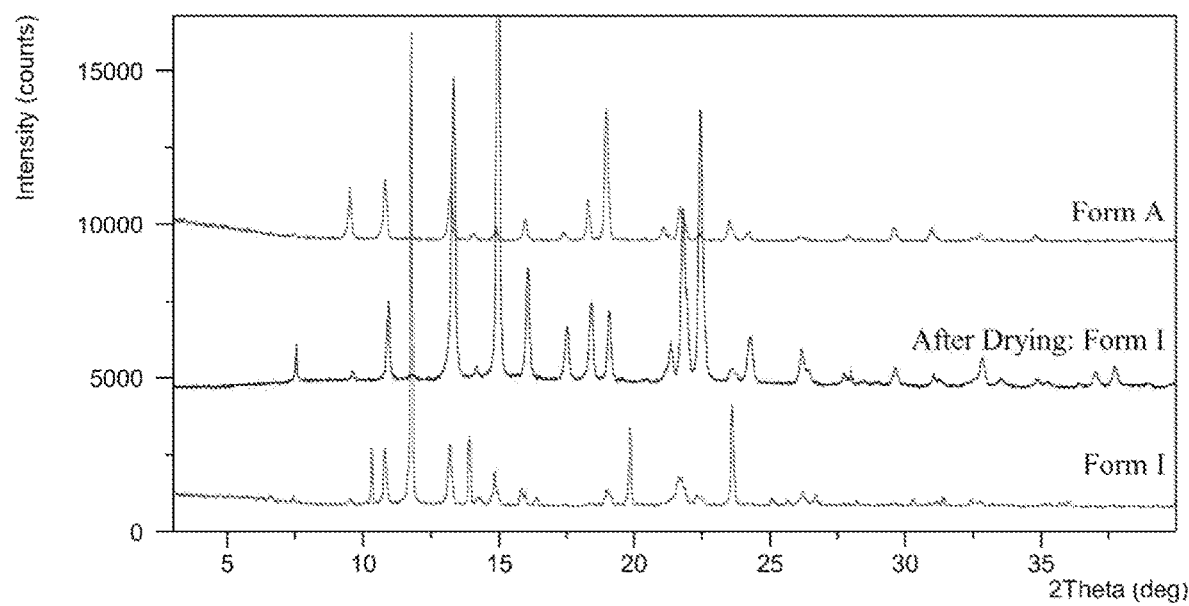
FIG. 8B depicts an overlay of exemplary XRPD patterns of Form I before and after drying at ambient conditions for 3 days along with an XRPD pattern of Form A.

Form I: The obtained XRPD pattern of the wet sample in FIG. 8A shows that Form I is crystalline. XRPD analysis indicates that Form I transforms to Form A after drying at ambient conditions for 3 days, as illustrated in FIG. 8B.

Figure 9A:
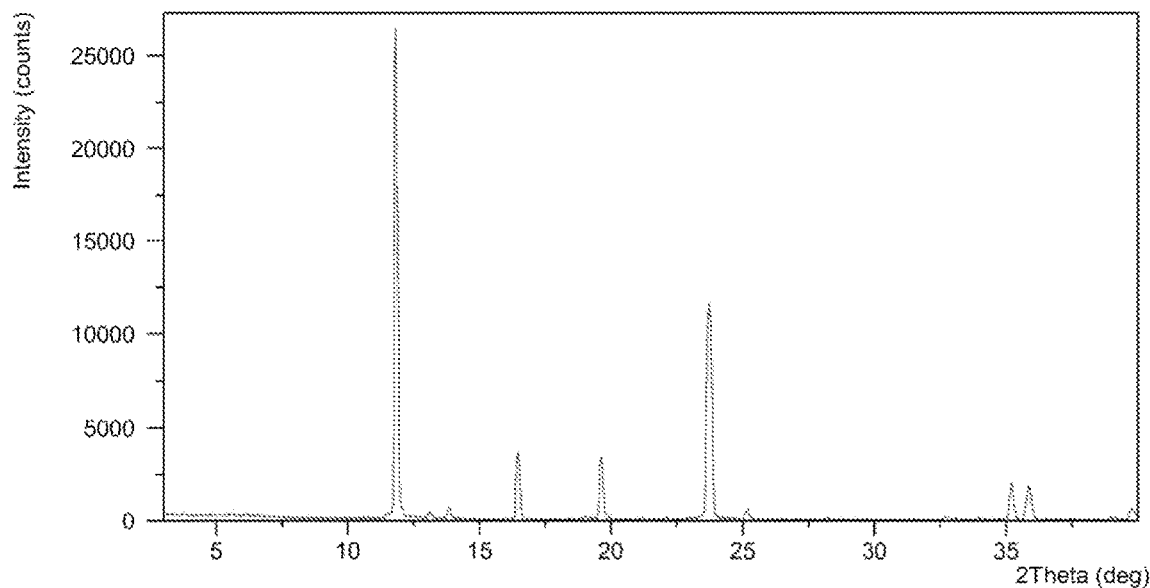
FIG. 9A depicts an exemplary XRPD pattern of Form J.
Figure 9B:
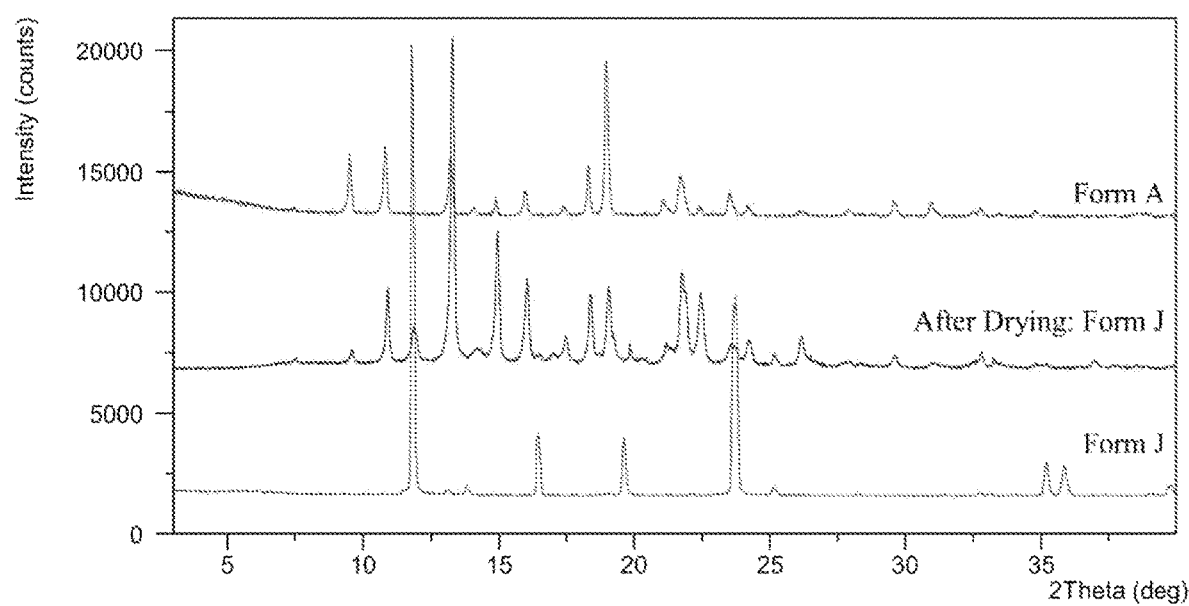
FIG. 9B depicts an overlay of exemplary XRPD patterns of Form J before and after drying at ambient conditions for 3 days, along with an XRPD pattern of Form A.

Form J: The obtained XRPD pattern of the wet sample in FIG. 9A shows that Form J is crystalline. XRPD analysis indicates that Form J transforms to Form A after drying at ambient conditions for 3 days, as illustrated in FIG. 9B.

Form K: The obtained XRPD pattern in FIG. 10A shows that Form K is crystalline.

Figure 11A:
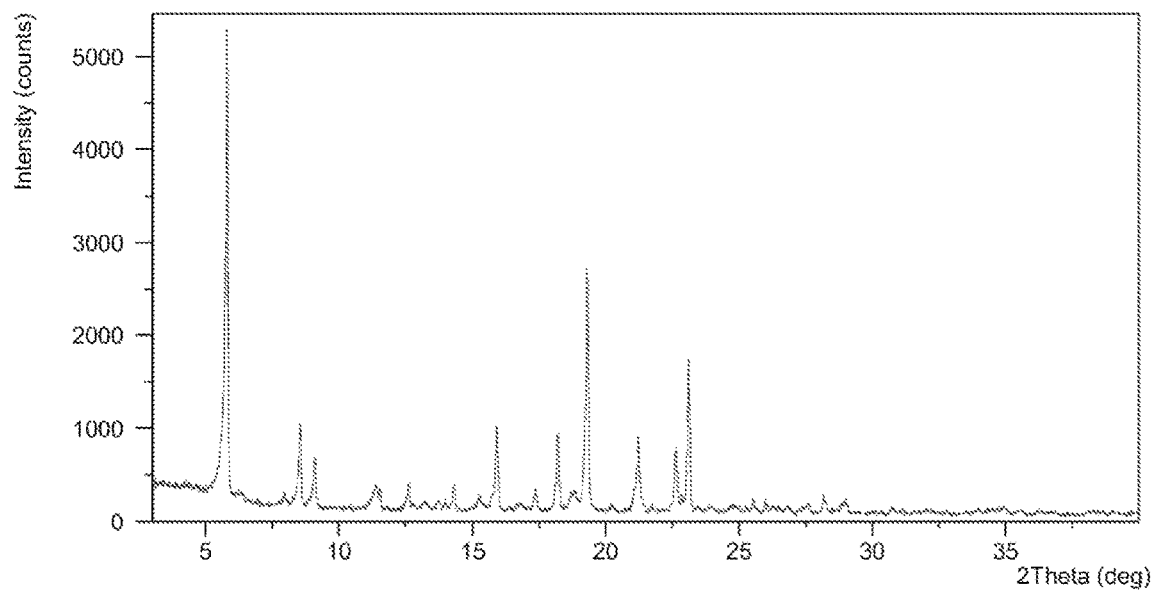
FIG. 11A depicts an exemplary XRPD pattern of Form L.
Figure 11B:
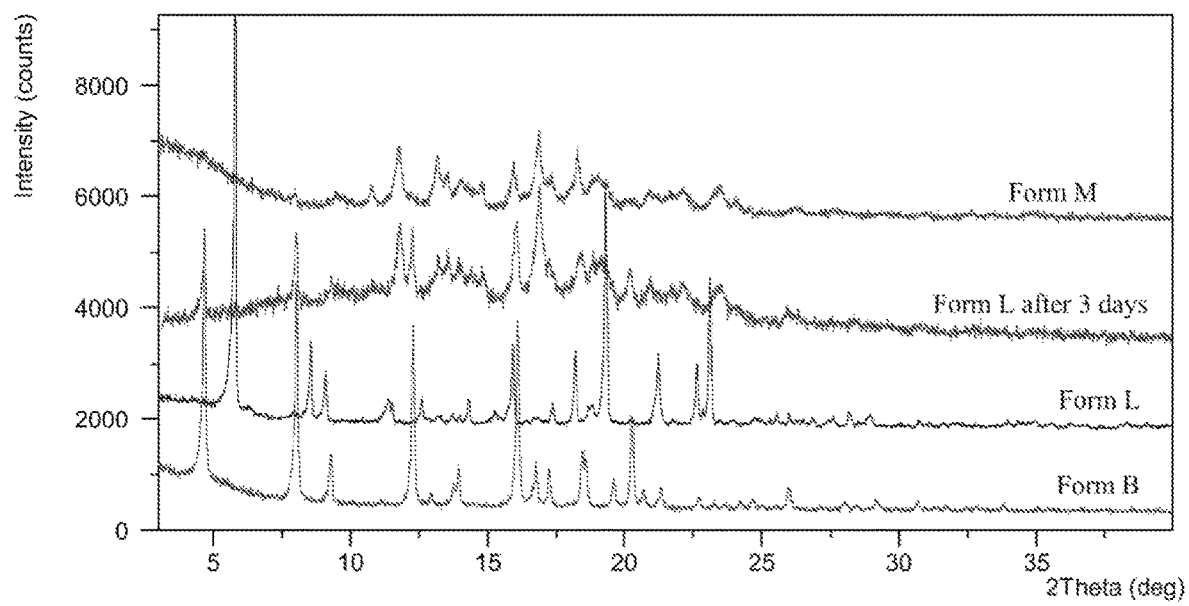
FIG. 11B depicts an overlay of exemplary XRPD patterns of Form L before and after 3 days, along with exemplary XRPD patterns of Form M and Form B.

Form L: The obtained XRPD pattern in FIG. 11A shows that Form L is crystalline. After 3 days at ambient conditions, Form L transforms to a mixture of Forms B and M, as shown in the XRPD pattern presented in FIG. 11B.

Figure 12:
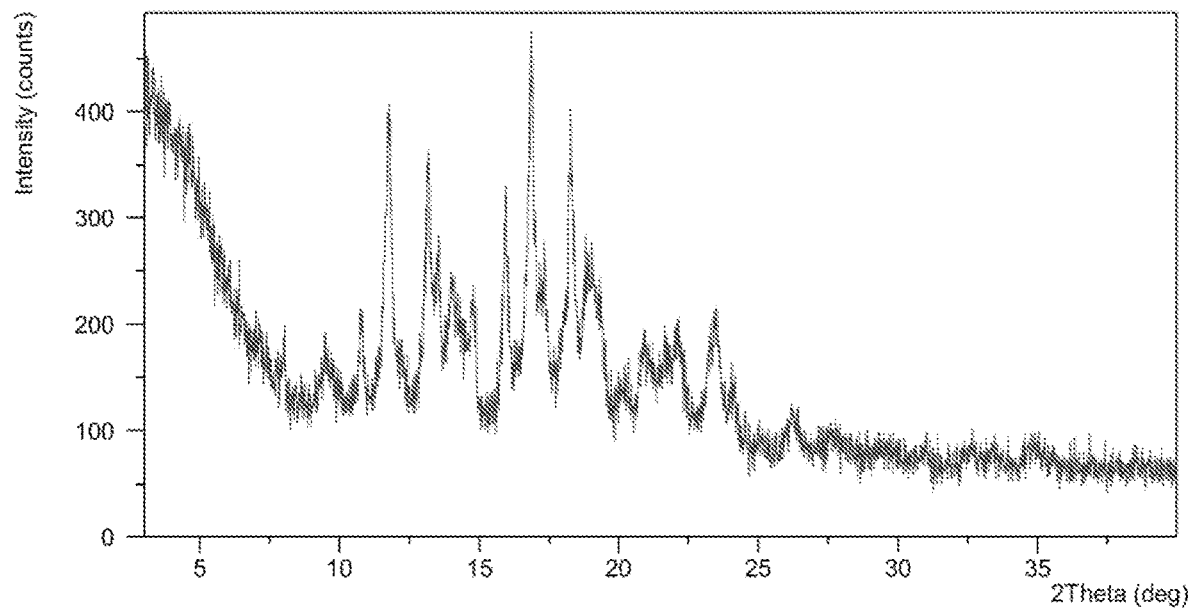
FIG. 12 depicts an exemplary XRPD pattern of Form M.

Form M: The obtained XRPD pattern in FIG. 12 shows that Form M has low crystallinity.

Figure 13A:
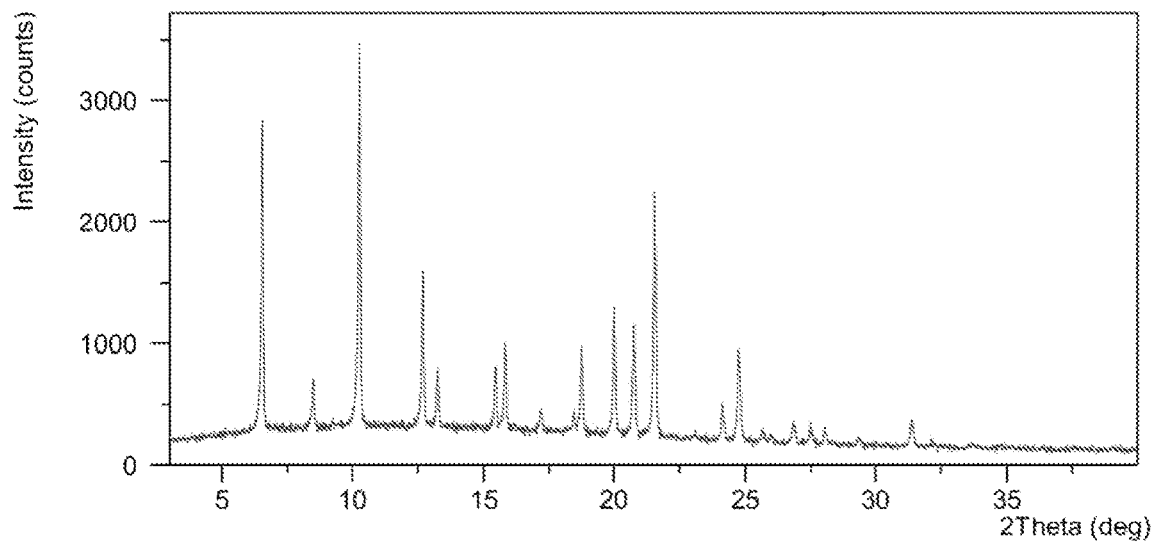
FIG. 13A depicts an exemplary XRPD pattern of Form N.
Figure 13B:
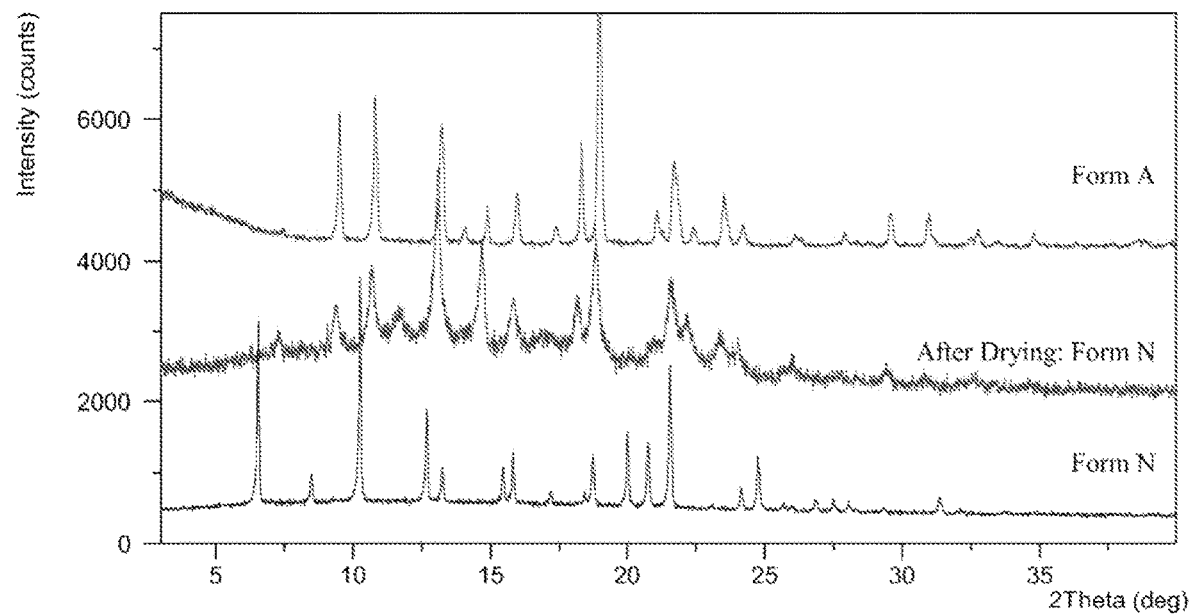
FIG. 13B depicts an overlay of exemplary XRPD patterns of Form N before and after drying at ambient conditions overnight, along with an exemplary XRPD pattern of Form A.

Form N: The XRPD pattern of the dried sample at ambient conditions in FIG. 13A shows that Form N is crystalline. The XRPD pattern in FIG. 13B shows that overnight, under ambient conditions, Form N transforms to Form A.

Figure 14A:
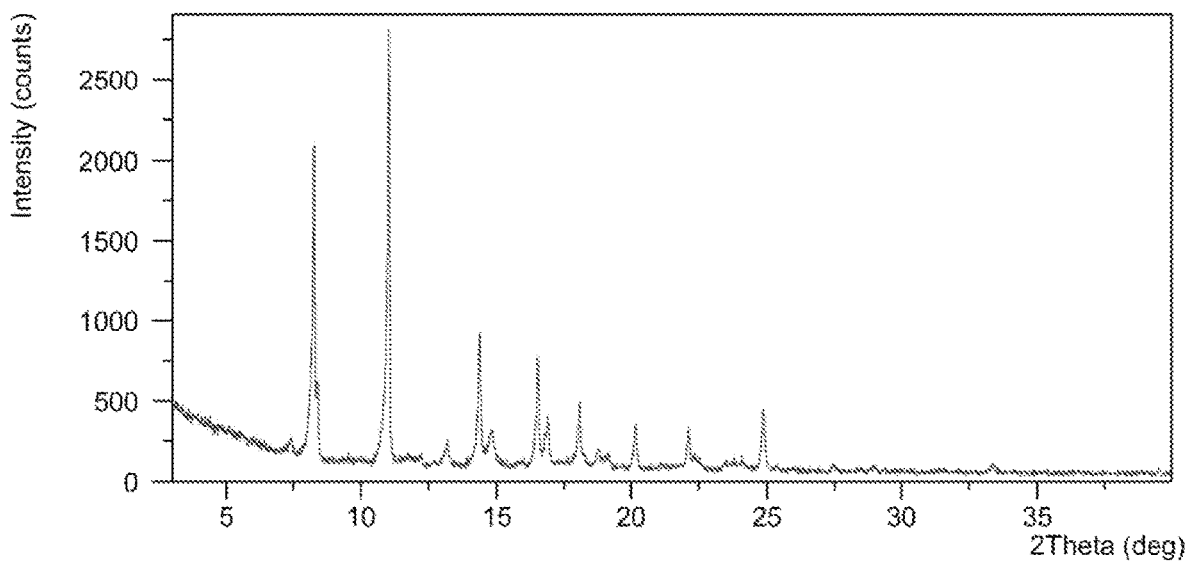
FIG. 14A depicts an exemplary XRPD pattern of Form O.

Form O: The obtained XRPD pattern in FIG. 14A shows that Form O is crystalline.

Example 17. Methods of Producing Single Crystals of Form A and Form C

Form A: Single crystals suitable for structure determination were obtained via slow cooling in isopropyl alcohol from 50° C. to 5° C.

Form C: Single crystals suitable for structure determination were obtained via slow cooling at a rate of 0.01° C./min in isopropyl acetate/acetone (6:1, v/v) co-solvents with Form C seeds, from 25° C. to 5° C.

Example 18. Single Crystal X-Ray Diffraction Data of Form A and Form C

X-ray intensity data from prism-like crystals of Form A (Table 9) and Form C (Table 10) were collected at 290(2) K using a Bruker D8 Venture diffractometer (Mo Kα radiation, λ=0.71073 Å). The crystal structures of Forms A and C were solved from the obtained data.

TABLE 9

Crystal data and structural refinement for a single crystal of Form A:

| | |
|---|---|
| Empirical formula | $C_{25}H_{35}N_3O_2$ |
| Formula weight | 409.56 |
| Temperature | 100(2) K |
| Wavelength | 0.71073 Å |
| Crystal system, space group | Monochnic$P2_1$ |
| Unit cell dimensions | a = 9.379(3) Å |
| | b = 9.922(3) Å |
| | c = 12.092(4) Å |
| | α = 90° |
| | β = 101.606(9)° |
| | γ = 90° |
| Volume | 1102.2(6) Å$^3$ |
| Z, Calculated density | 2, 1.234 Mg/m$^3$ |
| Absorption coefficient | 0.079 mm$^{-1}$ |
| F(000) | 444 |
| Crystal size | 0.30 × 0.20 × 0.10 mm$^3$ |
| Theta range for data collection | 2.22-27.56° |
| Limiting indices | −12 ≤ h ≤ 12 |
| | −12 ≤ k ≤ 12 |
| | −15 ≤ l ≤ 15 |
| Reflections collected/unique | 23466/5060 [R(int) = 0.0670] |
| Completeness | 99.9% |
| Refinement method | Full-matrix least-squares on F$^2$ |
| Data/restraints/parameters | 5060/1/274 |
| Goodness-of-fit on F$^2$ | 1.071 |
| Final R indices [I > 2sigma(I)] | $R_1$ = 0.0425 |
| | $wR_2$ = 0.0989 |
| Largest diff. peak and hole | 0.309 and −0.368 e · Å$^{-3}$ |
| Absolute structure parameter | 1.5(11) |

TABLE 10

Crystal data and structural refinement for a single crystal of Form C:

| | |
|---|---|
| Empirical formula | $C_{25}H_{35}N_3O_2$ |
| Formula weight | 409.56 |
| Temperature | 290(2) K |
| Wavelength | 0.71073 Å |
| Crystal system, space group | Orthorhombic $P2_12_12_1$ |
| Unit cell dimensions | a = 9.6642(8) Å |
| | b = 9.8676(8) Å |
| | c = 23.9408(19) Å |
| | α = 90° |
| | β = 90° |
| | γ = 90° |
| Volume | 2283.1(3) Å$^3$ |
| Z, Calculated density | 4, 1.192 mg/m$^3$ |
| Absorption coefficient | 0.076 mm$^{-1}$ |
| F(000) | 888 |
| Crystal size | 0.28 × 0.05 × 0.03 mm$^3$ |
| Theta range for data collection | 2.71-27.61° |
| Limiting indices | −12 ≤ h ≤ 12 |
| | −12 ≤ k ≤ 12 |
| | −31 ≤ l ≤ 31 |
| Reflections collected/unique | 33905/5265 [R(int) = 0.0823] |
| Completeness | 99.3% |
| Refinement method | Full-matrix least-squares on F$^2$ |
| Data/restraints/parameters | 5265/7/272 |
| Goodness-of-fit on F$^2$ | 1.042 |
| Final R indices [I > 2sigma(I)] | $R_1$ = 0.0647 |
| | $wR_2$ = 0.1128 |
| Largest diff. peak and hole | 0.248 and −0.335 e · Å$^{-3}$ |
| Absolute structure parameter | 0.0(19) |

Example 19. Unit Cells of the Single-Crystal Structures of Form A and Form C

Figure 1B:
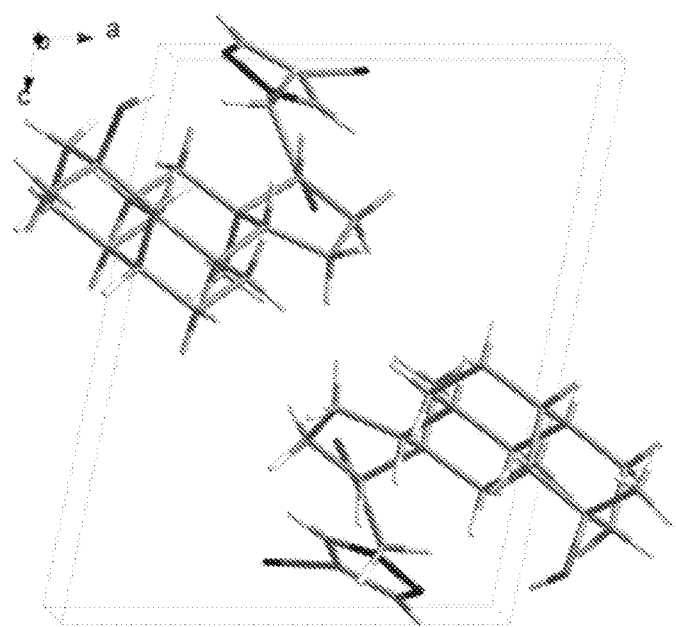
FIG. 1B depicts an exemplary unit cell of Form A along the b axis.
Figure 3B:
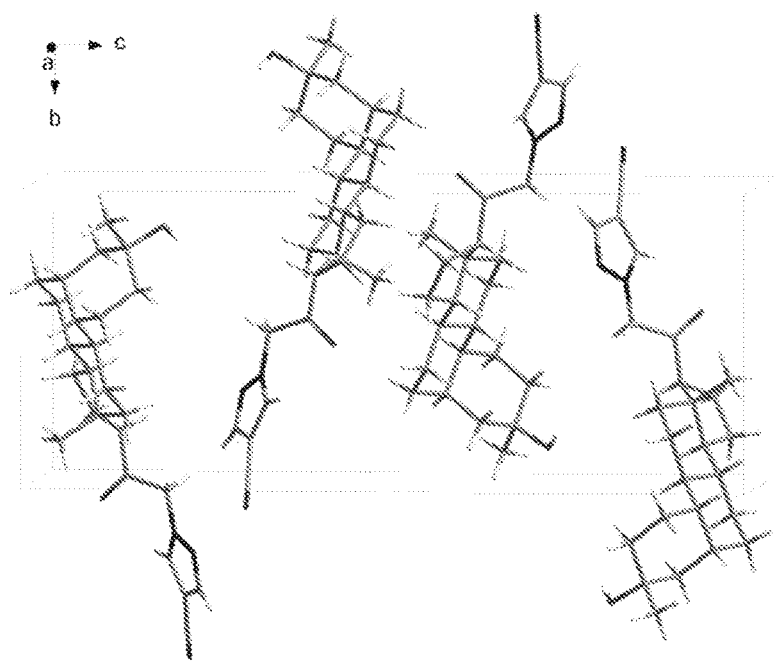
FIG. 3B depicts an exemplary unit cell of Form C along the b axis.

The unit cell of Form A along the b axis is depicted in FIG. 1B. The unit cell of Form C along the b axis is depicted in FIG. 3B.

Example 20. Characterization of Solid Forms A-O by Temperature-Dependent Instrumental Methods (TGA, DSC, and VT-XRPD)

Thermogravimetric analysis (TGA) data were collected using a TA Q500/Q5000 TGA from TA Instruments, and differential scanning calorimetry (DSC) was performed using a TA Q200/Q2000 DSC from TA Instruments. The instrument parameters used are provided in Table 11.

TABLE 11

Parameters for TGA and DSC Test

| Parameters | TGA | DSC |
|---|---|---|
| Method | Ramp | Ramp |
| Sample pan | Platinum, open | Aluminum, crimped |
| Temperature | RT to 350° C. | RT to 300° C. |
| Heating rate | 10° C./min | 10° C./min |
| Purge gas | $N_2$ | $N_2$ |

To complement the temperature-dependent studies and confirm the solvation state of the solid forms, solution NMR was collected on a Bruker 400 MHz NMR Spectrometer using deuterated dimethyl sulfoxide (DMSO-d6) as the solvent.

Figure 1C:
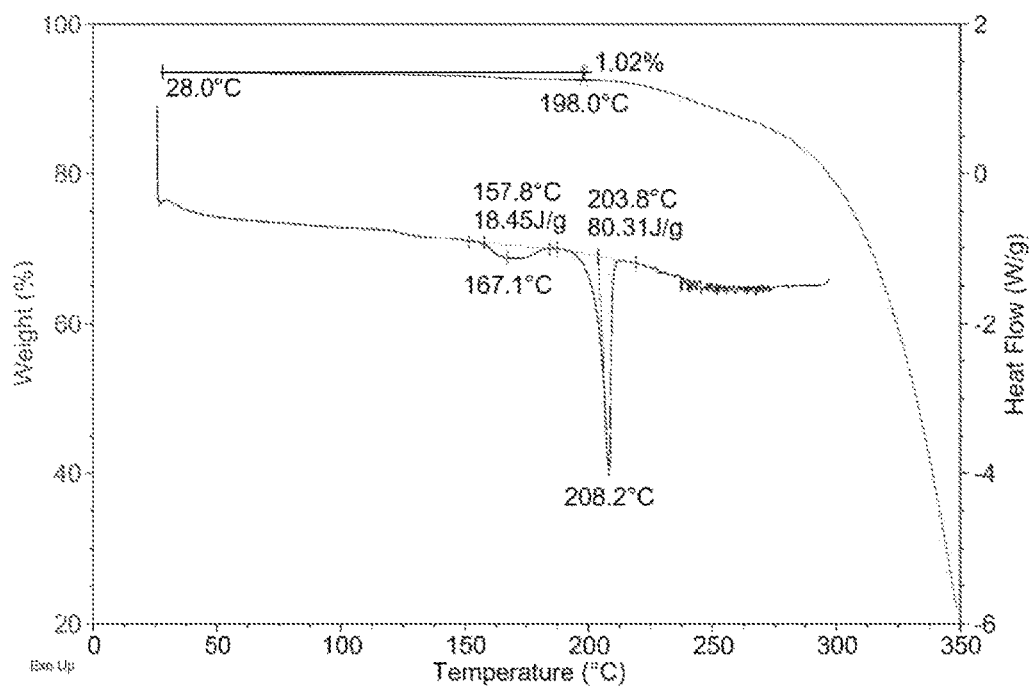
FIG. 1C depicts exemplary TGA (upper) and DSC (lower) curves of Form A.
Figure 1D:
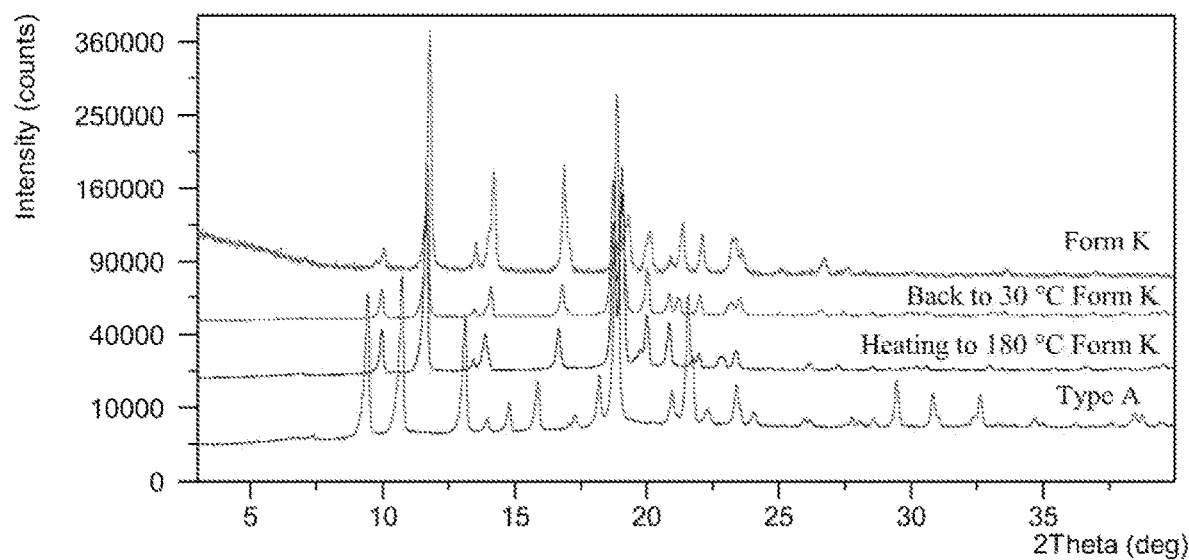
FIG. 1D depicts an overlay of exemplary VT-XRPD patterns of Form A at selected temperatures, along with an exemplary XRPD pattern of Form K.

Form A: TGA and DSC were performed and the details provided in FIG. 1C. Thermogravimetric analysis of Form A resulted in a 1.0% weight loss up to 200° C. An endotherm observed on the DSC curve at 157.2° C. (onset temperature), representing the transformation of Form A to Form K, was followed by a sharp melting peak for Form K at 203.8° C. (onset temperature). Verification of the transformation to Form K was performed by VT-XRPD, as shown in FIG. 1D.

Figure 2C:
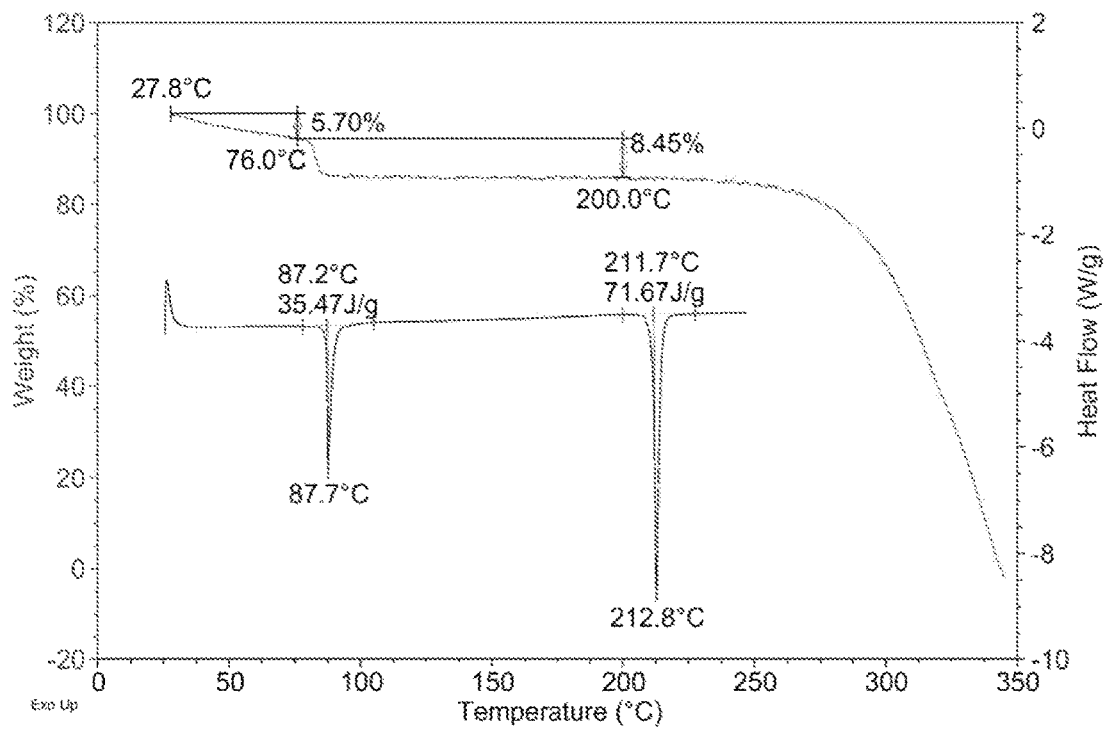
FIG. 2C depicts exemplary TGA (upper) and DSC (lower) curves of an isomorph of Form B.
Figure 2D:
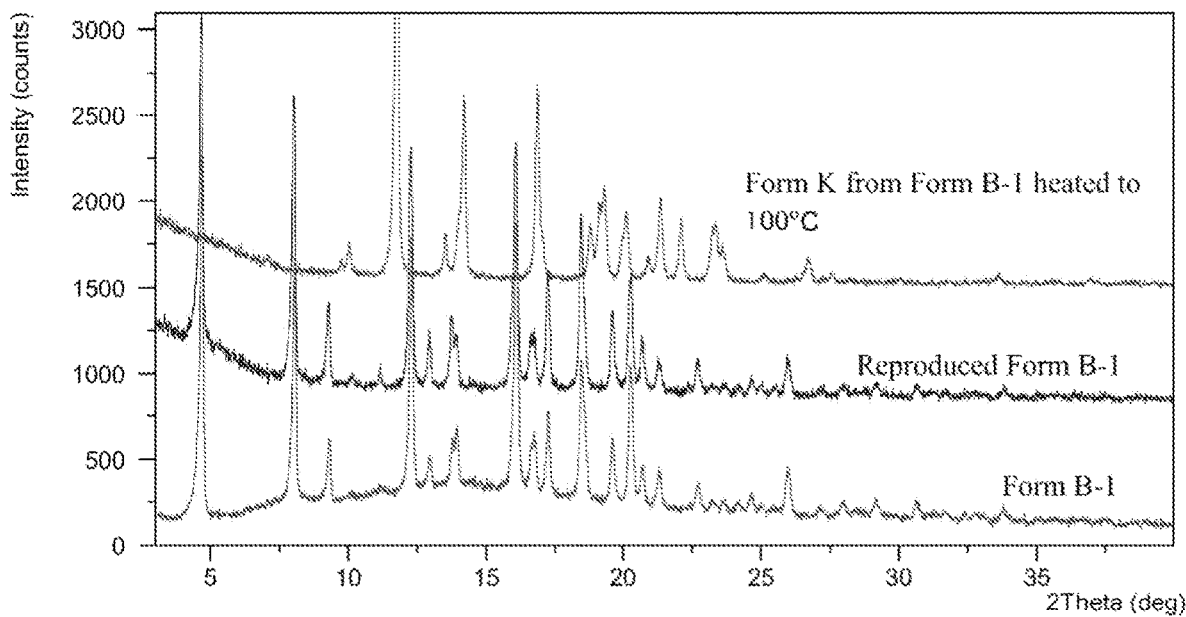
FIG. 2D depicts an overlay of exemplary VT-XRPD patterns of an isomorph of Form B along with an exemplary XRPD pattern of Form K.

Form B-1: TGA and DSC were performed, and their respective curves are provided in FIG. 2C. The TGA curve shows a 2-stage weight loss, with a 5.7% loss of residual solvent up to 76° C. followed by an 8.5% loss (desolvation) up to 200° C. The DSC curve exhibits 2 endothermic peaks at 87.2° C. and 211.7° C. (onset temperatures), corresponding to the loss of solvent (transformation to Form K) and the melting point of Form K, respectively. Analysis by XPRD indicates that Form B-1 transforms to Form K upon heating to 100° C., as shown in FIG. 2D. Based on the $^1$H NMR data shown in FIG. 2G, Form B is an n-heptane solvate with a molar ratio of 1:0.4 Compound 1: n-heptane (~8.9% n-heptane by weight), which is in good agreement with the TGA result. Residual DCM with a molar ratio of 1:0.06 Compound 1:DCM (1.2% by weight) was also observed in the $^1$H NMR data.

Figure 2E:
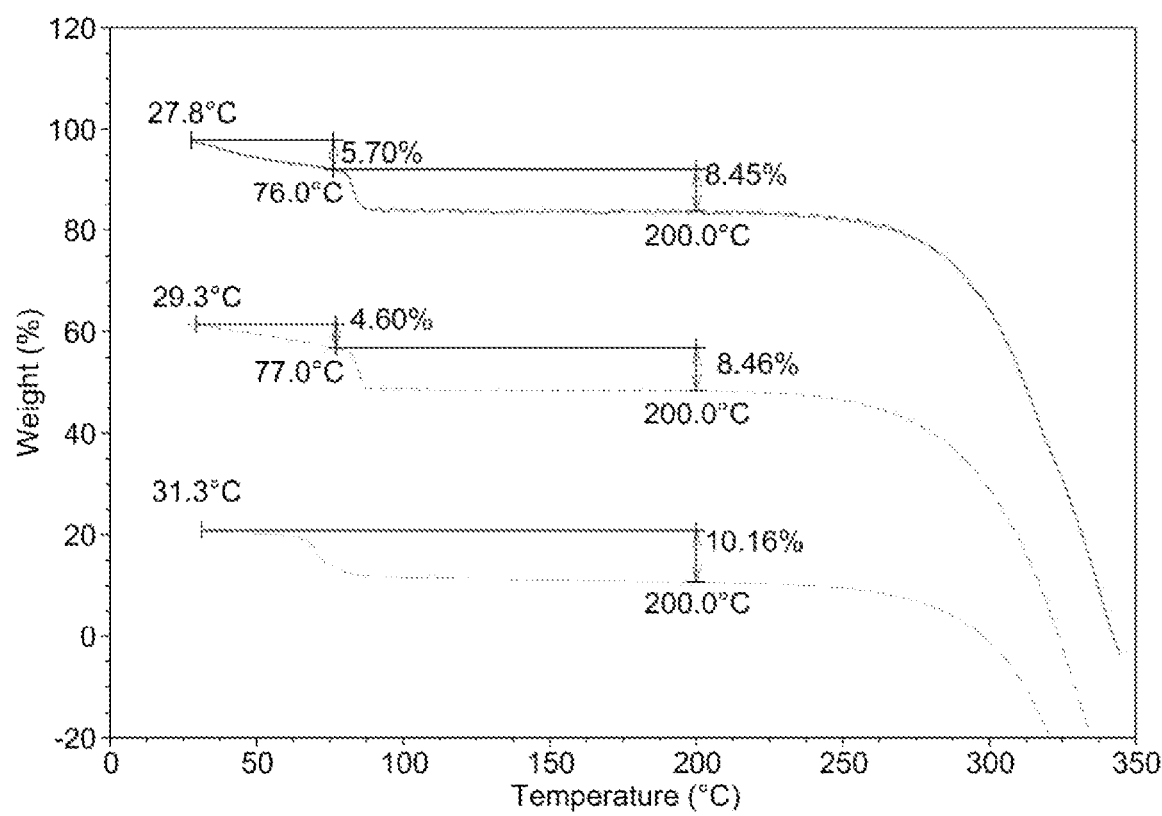
FIG. 2E depicts exemplary TGA curves of isomorphs of Form B.
Figure 2F:
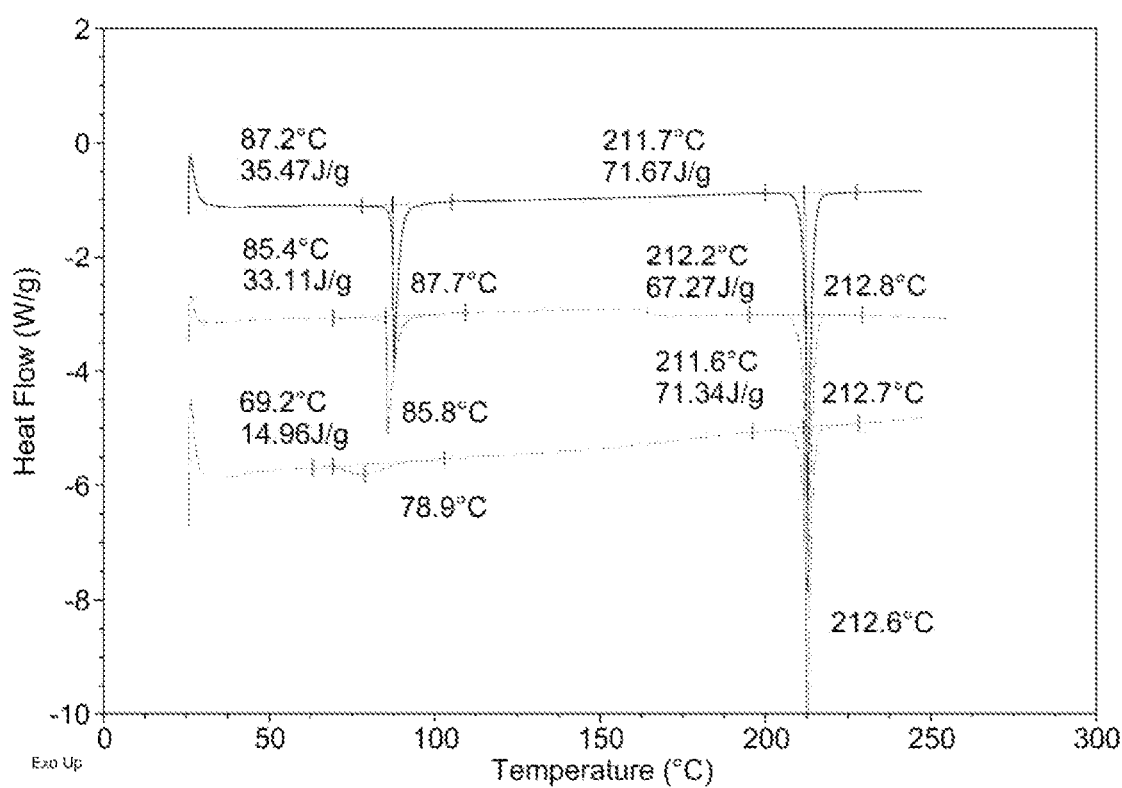
FIG. 2F depicts exemplary DSC curves of isomorphs of Form B.
Figure 2G:
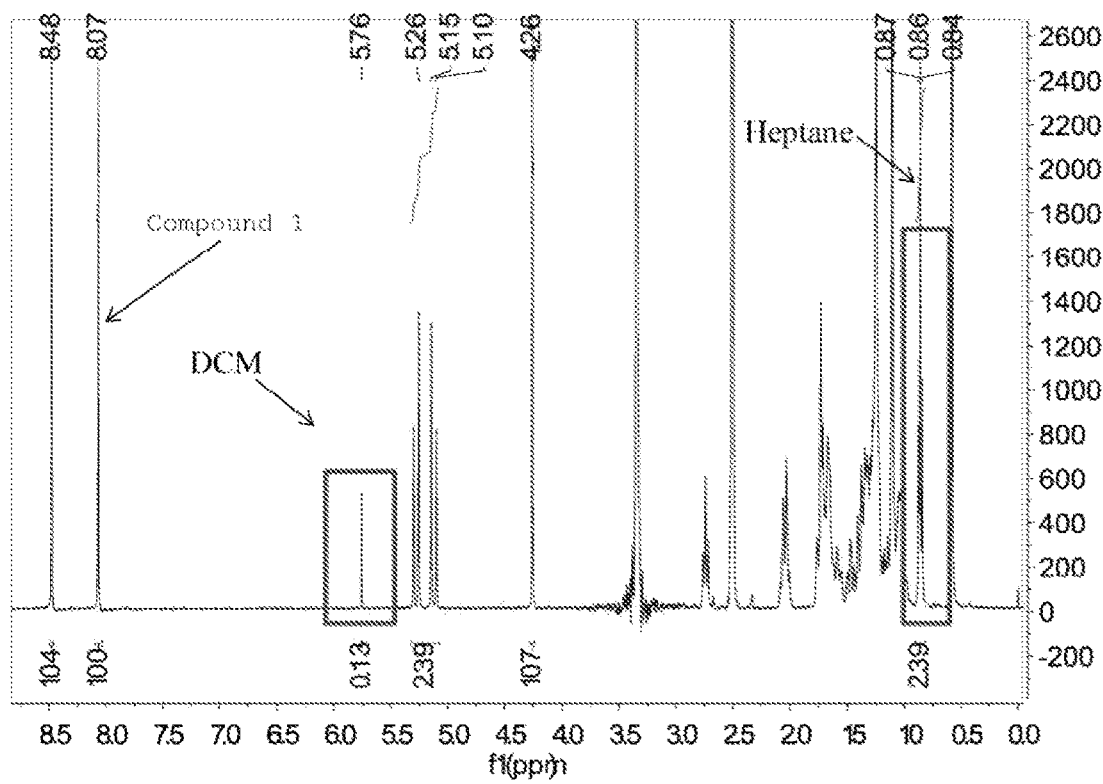
FIG. 2G depicts an exemplary $^1$H NMR spectrum of an isomorph of Form B dissolved in DMSO-$d_6$.
Figure 2H:
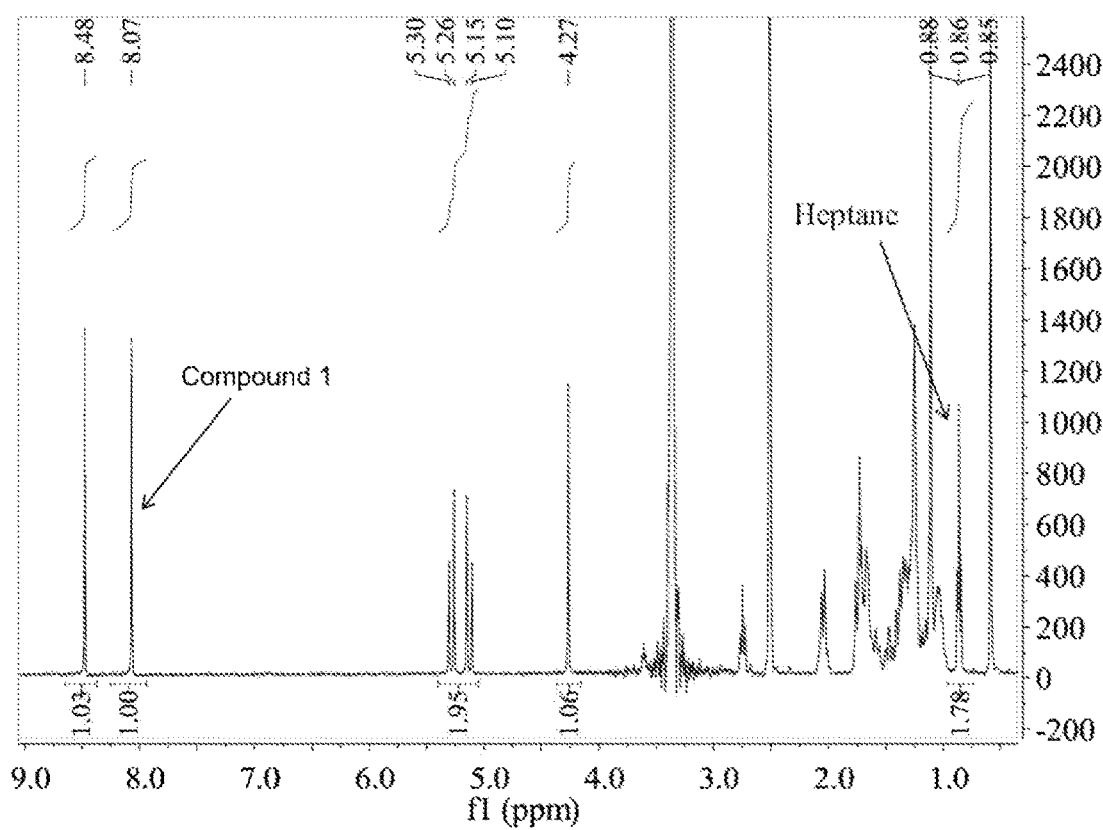
FIG. 2H depicts an exemplary $^1$H NMR spectrum of an isomorph of Form B dissolved in DMSO-$d_6$.

Form B-2: The TGA of this isomorph is shown in FIG. 2E along with the TGA curves of the other two isomorphs. The DSC curve of this isomorph, which is depicted in FIG. 2F along with an overlay of the other two isomorphs, exhibits two endotherms, one at a $T_{onset}$ of 85.4° C. and one at a $T_{onset}$ of 212.2° C. The $^1$H NMR spectrum in FIG. 2H showed that Form B is an n-heptane solvate in a molar ratio of 1:0.3 Compound 1: n-heptane, with no THF observed.

Figure 2I:
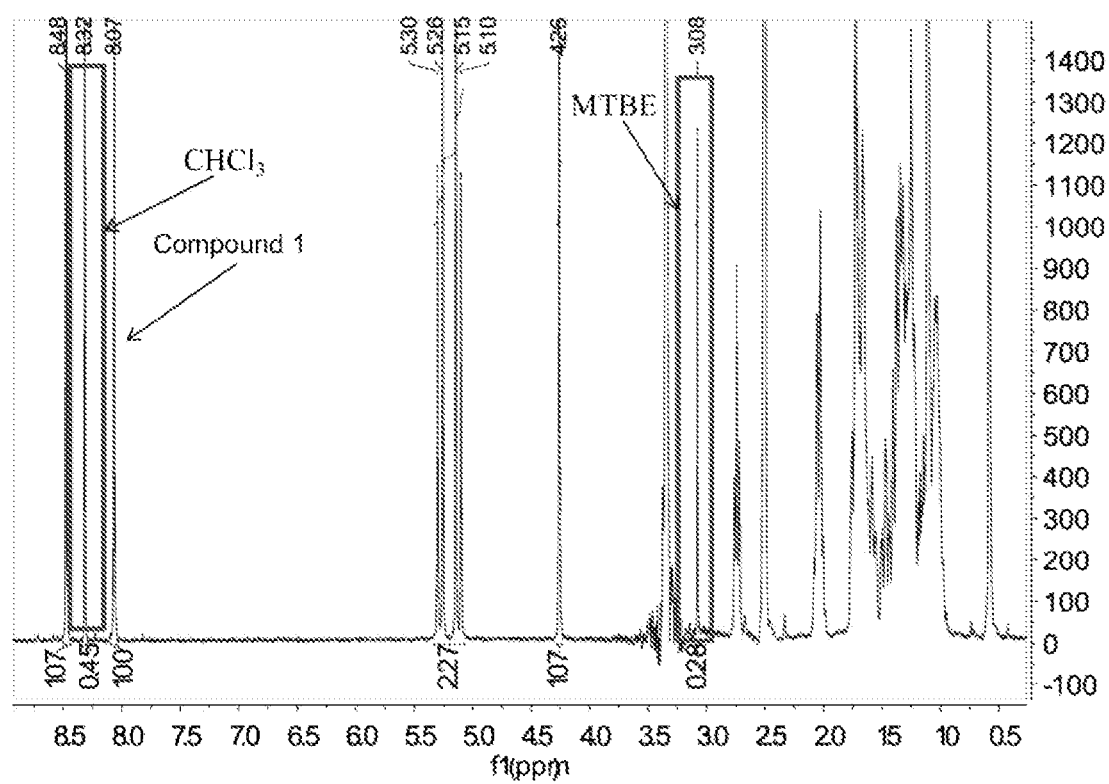
FIG. 2I depicts an exemplary $^1$H NMR spectrum of an isomorph of Form B dissolved in DMSO-$d_6$.

Form B-3: The TGA of this isomorph is shown in FIG. 2E along with the TGA curves of the other two isomorphs. The DSC curve of this isomorph, which is depicted in FIG. 2F along with an overlay of the other two isomorphs, exhibits two endotherms, one at a $T_{onset}$ of 69.2° C. and one at a $T_{onset}$ of 211.6° C. The $^1$H NMR spectrum in FIG. 2I showed that Form B is a chloroform solvate in a molar ratio of 1:0.5 Compound 1:chloroform, with residual methyl tert-butyl ether detected.

Figure 3C:
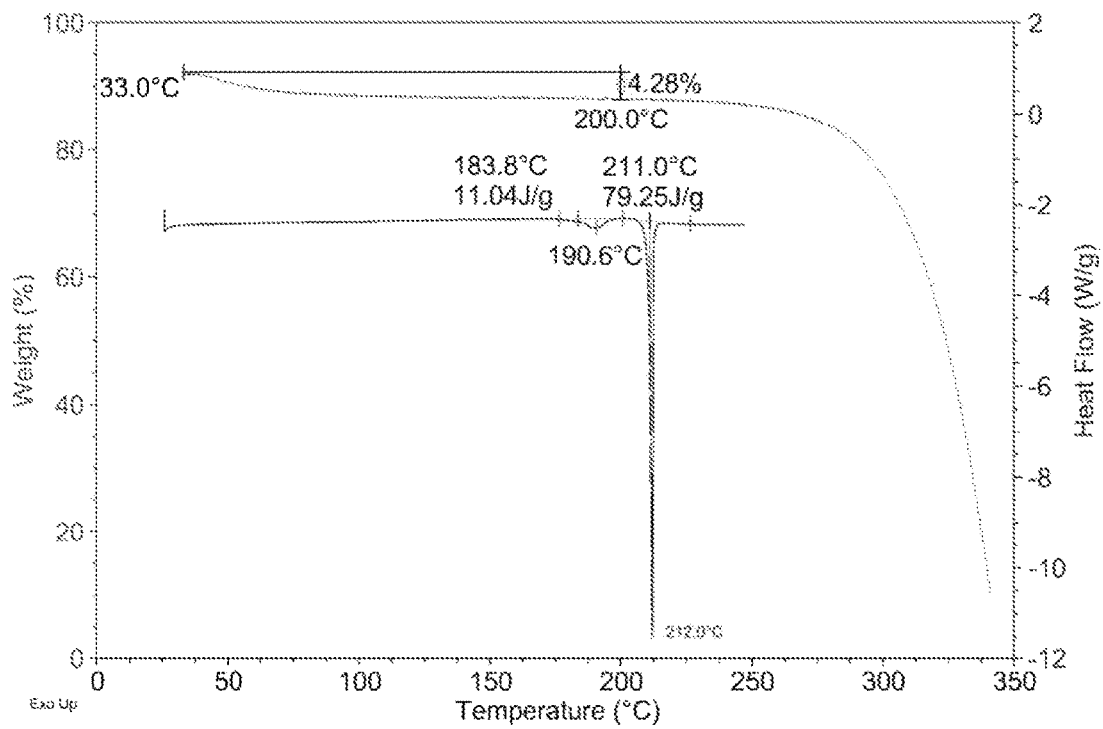
FIG. 3C depicts exemplary TGA (upper) and DSC (lower) curves of Form C.
Figure 3D:
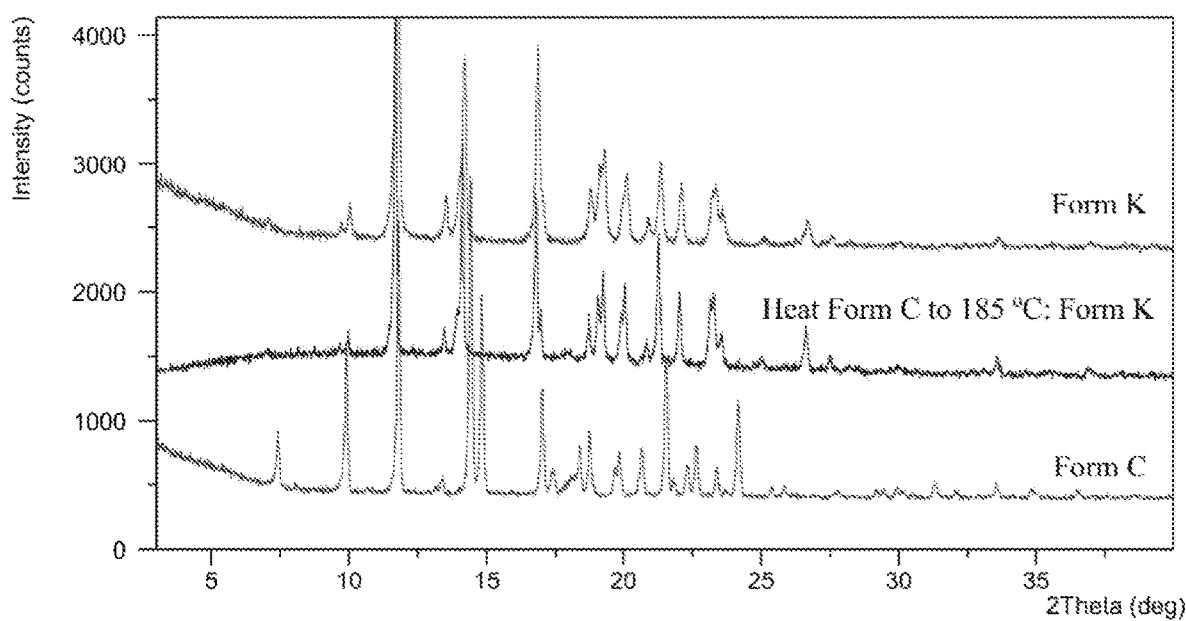
FIG. 3D depicts an overlay of exemplary XRPD patterns of Form C at selected temperatures as well as an exemplary XRPD pattern of Form K.
Figure 3E:
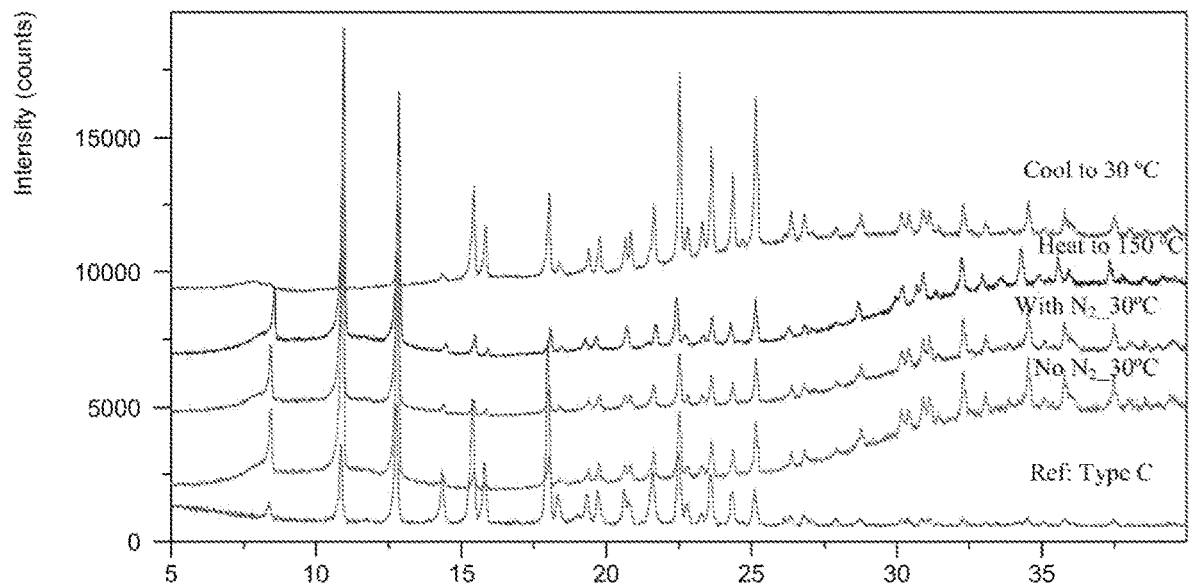
FIG. 3E depicts an overlay of exemplary XRPD patterns of Form C at selected temperatures in the presence or absence of an $N_2$ atmosphere.

Form C: TGA and DSC were performed, and their respective curves are provided in FIG. 3C. The TGA curve shows that a weight loss of 4.3% occurs below 50° C. indicating loosely held solvent or adventitious solvent, possibly present due to insufficient drying. The DSC curve exhibits 2 endothermic peaks at 183.8° C. and 211.0° C. (onset temperatures). Further investigation of the endotherm at 183.8° C. was performed by heating Form C to 185° C., which resulted in a form transformation to Form K, as shown in FIG. 3D. Analysis by VT-XRPD was performed on Form C, with and without nitrogen (N$_2$) flow, to investigate possible rehydration from air. As shown in FIG. 3E, no differences were observed with and without N$_2$, indicating that Form C is an anhydrate.

Figure 6B:
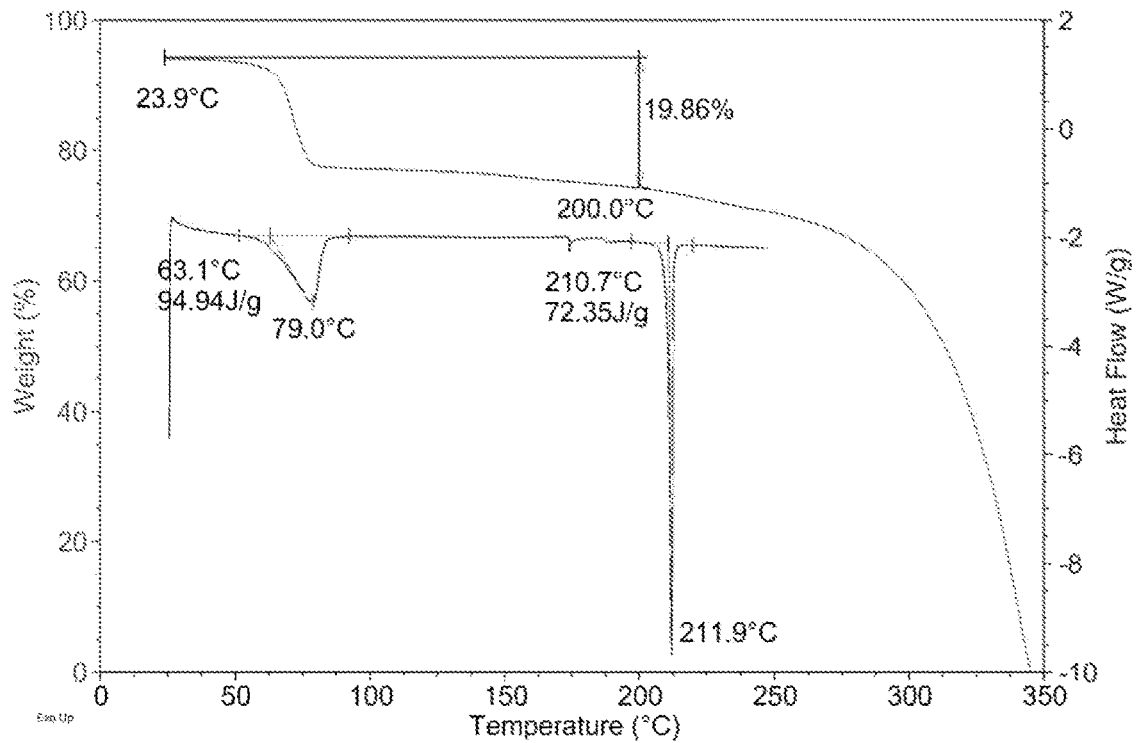
FIG. 6B depicts exemplary TGA (upper) and DSC (lower) curves of Form F.
Figure 6C:
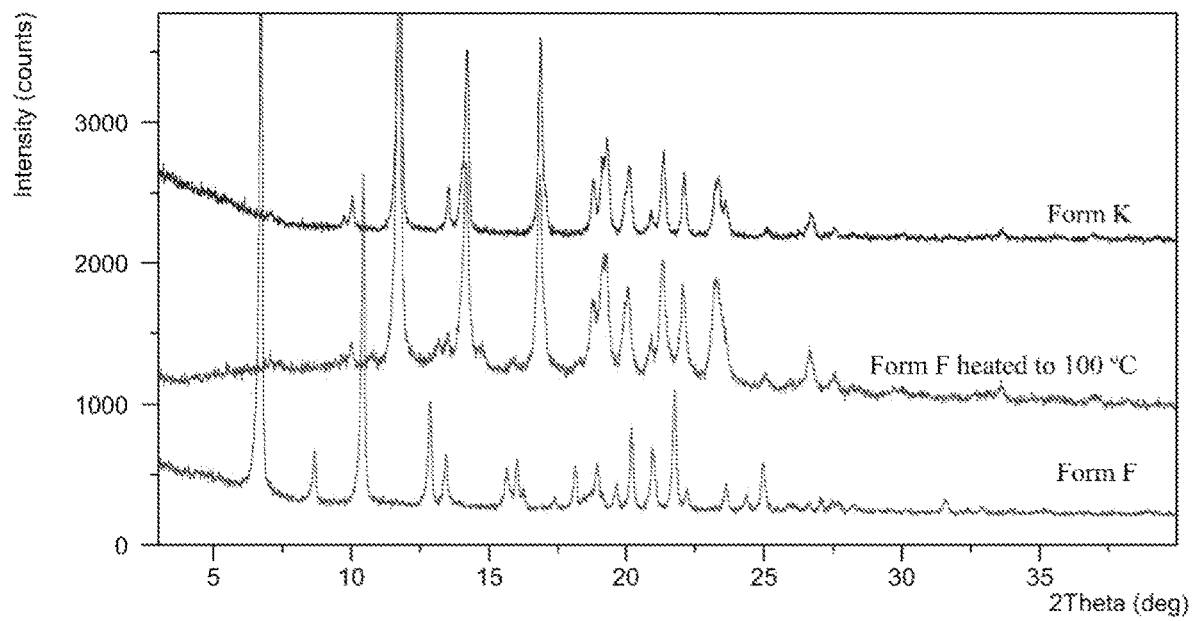
FIG. 6C depicts an overlay of exemplary XRPD patterns of Form F at selected temperatures along with an exemplary XRPD pattern of Form K.
Figure 6D:
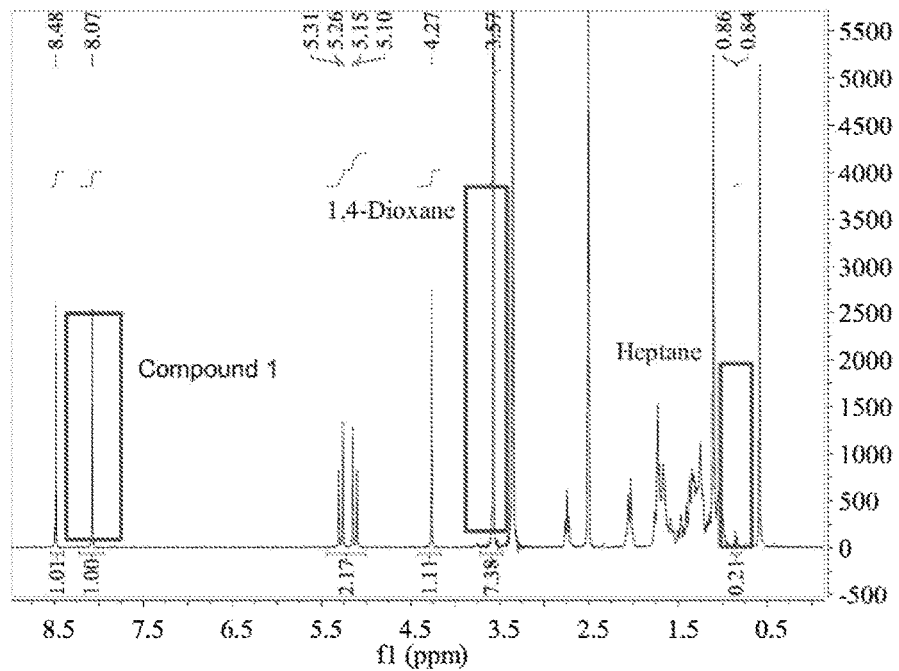
FIG. 6D depicts an exemplary $^1$H NMR spectrum of Form F dissolved in DMSO-$d_6$.

Form F: TGA and DSC were performed, and their respective curves are provided in FIG. 6B. The TGA curve shows a total weight loss of 19.7% up to 200° C. The DSC curve exhibits 2 endothermic peaks at 63.1° C. and 210.7° C. (onset temperatures), corresponding to the loss of solvent (transformation to Form K) and the melting point of Form K, respectively. This is further evidenced by the transformation of Form F to Form K after heating to 100° C., as shown in FIG. 6C. Based on the $^1$H NMR spectrum shown in FIG. 6D, Form F is a 1,4-dioxane solvate with a molar ratio of 1:0.9 (16.2% 1,4-dioxane by weight), which is in good agreement with the TGA result. Residual n-heptane at a molar ratio of 1:0.03 (0.7% n-heptane by weight) is also observed in the $^1$H NMR data.

Figure 10B:
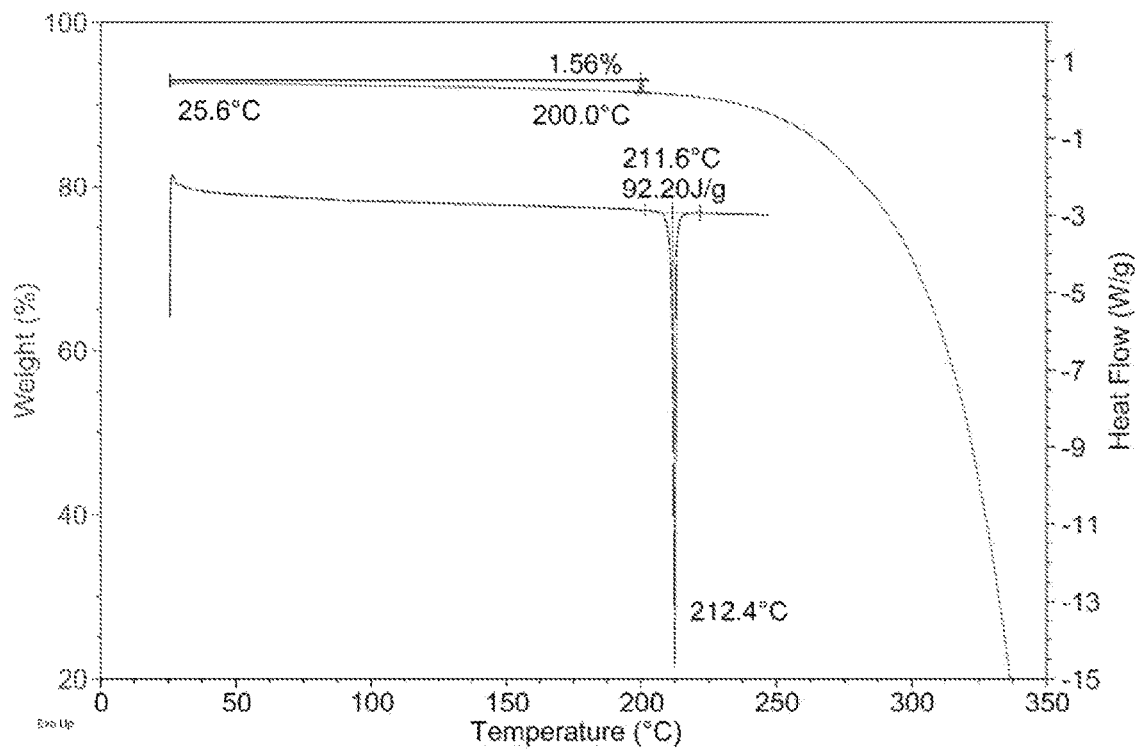
FIG. 10B depicts exemplary TGA (upper) and DSC (lower) curves of Form K.

Form K: TGA and DSC were performed, and their respective curves are provided in FIG. 10B. The TGA curve shows a weight loss of 1.6% up to 200° C., and the DSC curve exhibits an endothermic peak at 211.6° C. (onset temperature), corresponding to the melting endotherm of Form K. Based on the low volatiles content, Form K is an unsolvated material.

Figure 11C:
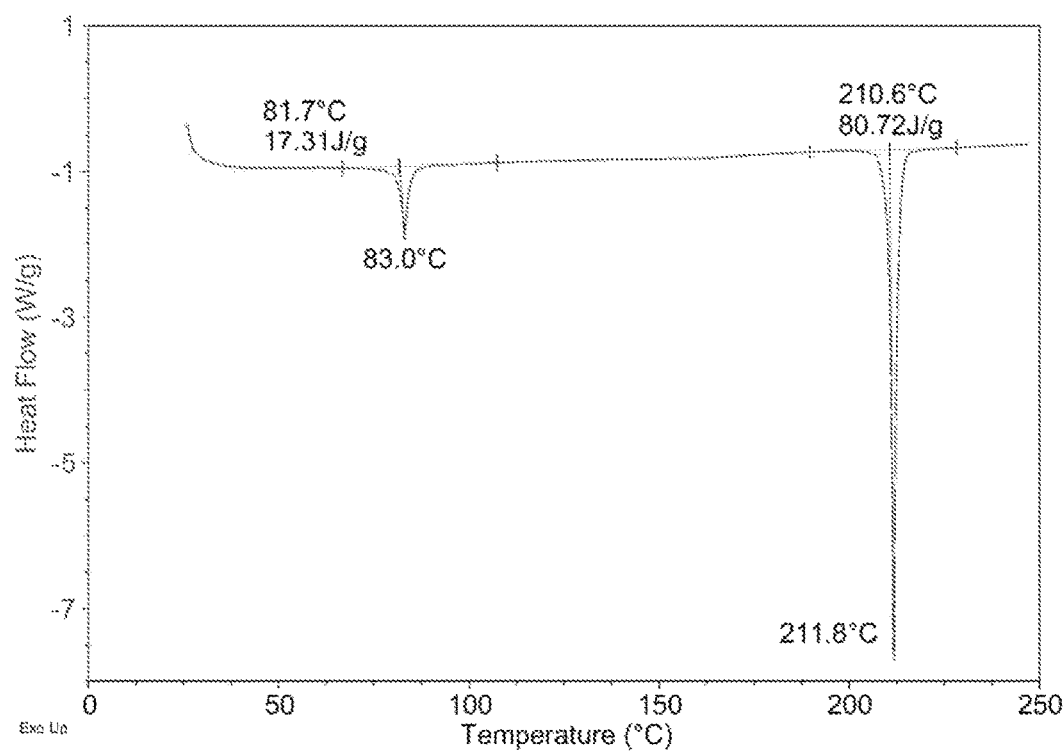
FIG. 11C depicts an exemplary DSC curve of Form L.

Form L: The DSC curve of Form L, shown in FIG. 11C exhibits 2 endothermic peaks at 81.7° C. and 210.6° C. (onset temperatures). The first endothermic peak is attributed to the possible loss of solvent or form transformation. The second endothermic peak in the DSC curve matches the melting endotherm of Form K.

Figure 13C:
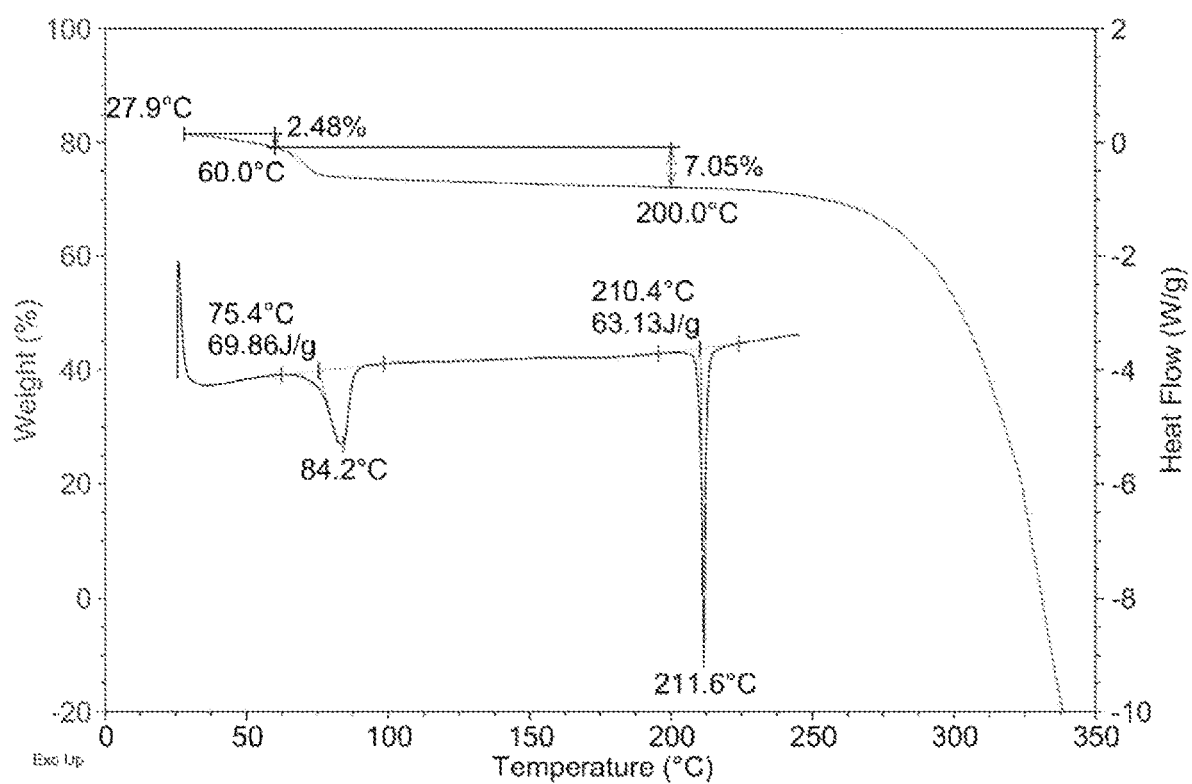
FIG. 13C depicts exemplary TGA (upper) and DSC (lower) curves of Form N.
Figure 13D:
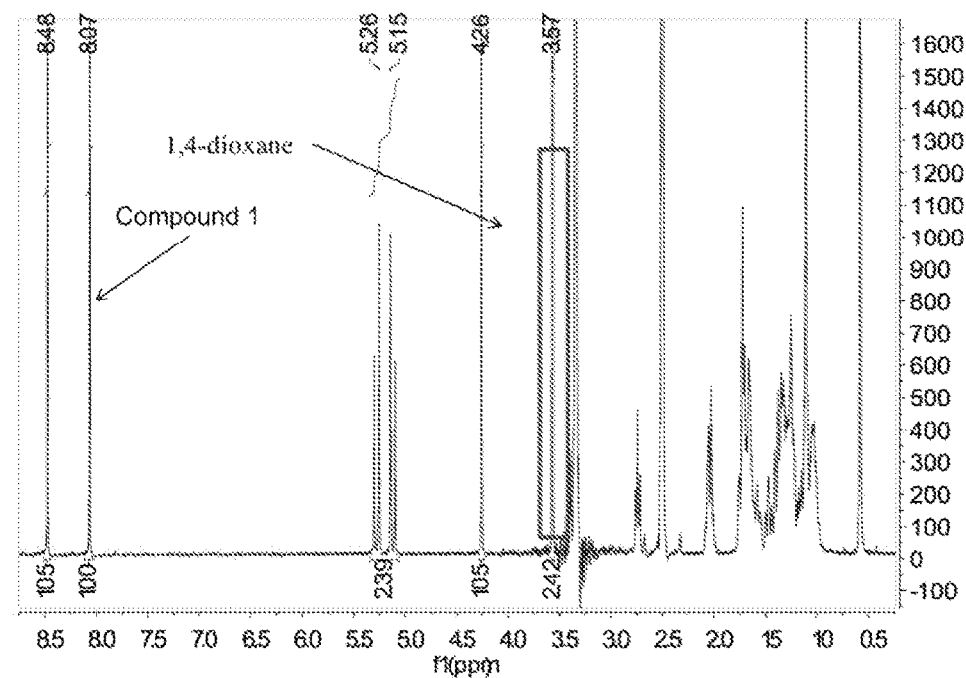
FIG. 13D depicts an exemplary 1H NMR spectrum of Form N dissolved in DMSO-$d_6$.

Form N: The TGA curve in FIG. 13C shows a 2-step weight loss of 2.5% up to 60° C., followed by 7.1% up to 200° C. The DSC curve exhibits 2 endothermic peaks at 75.4° C. and 210.4° C. (onset temperatures), attributed to the loss of solvent (based on $^1$H NMR) and the melting point of Form K, respectively. Based on the $^1$H NMR result in FIG. 13D, Form N is a 1,4-dioxane solvate with a molar ratio of 1:0.3 Compound 1:1,4-dioxane (6.1% 1,4-dioxane by weight), which is in agreement with the second step weight loss in the TGA analysis.

Figure 14B:
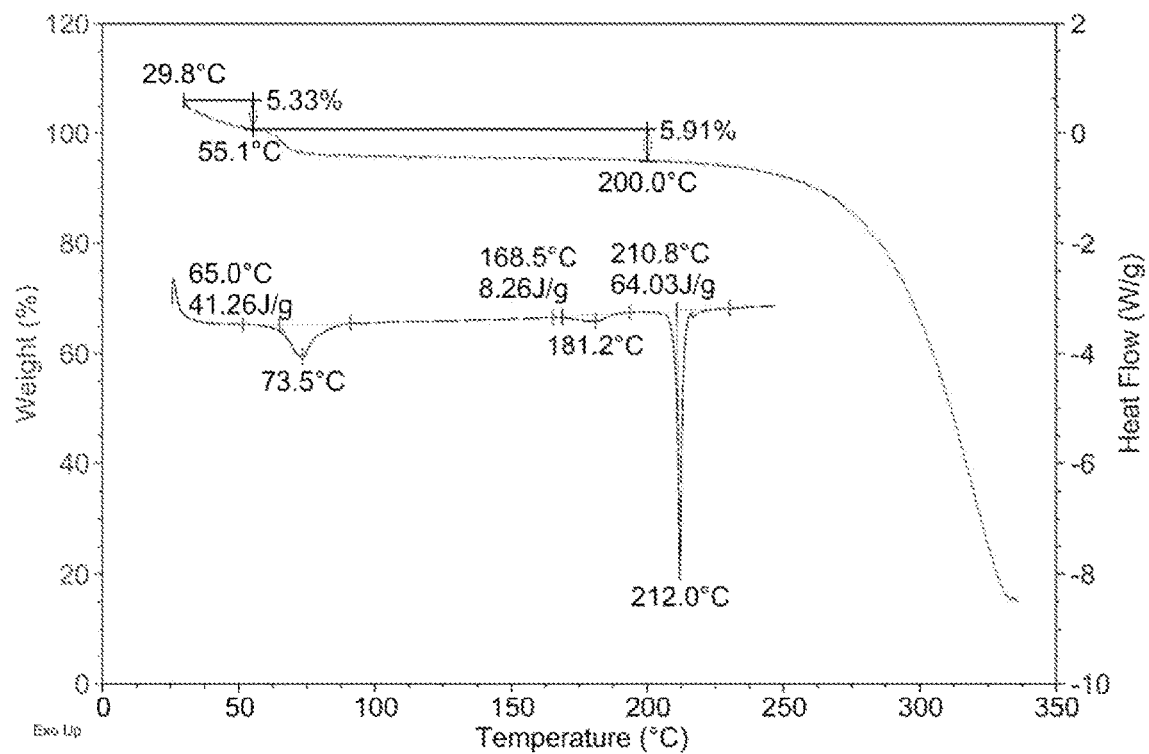
FIG. 14B depicts exemplary TGA (upper) and DSC (lower) curves of Form O.
Figure 14C:
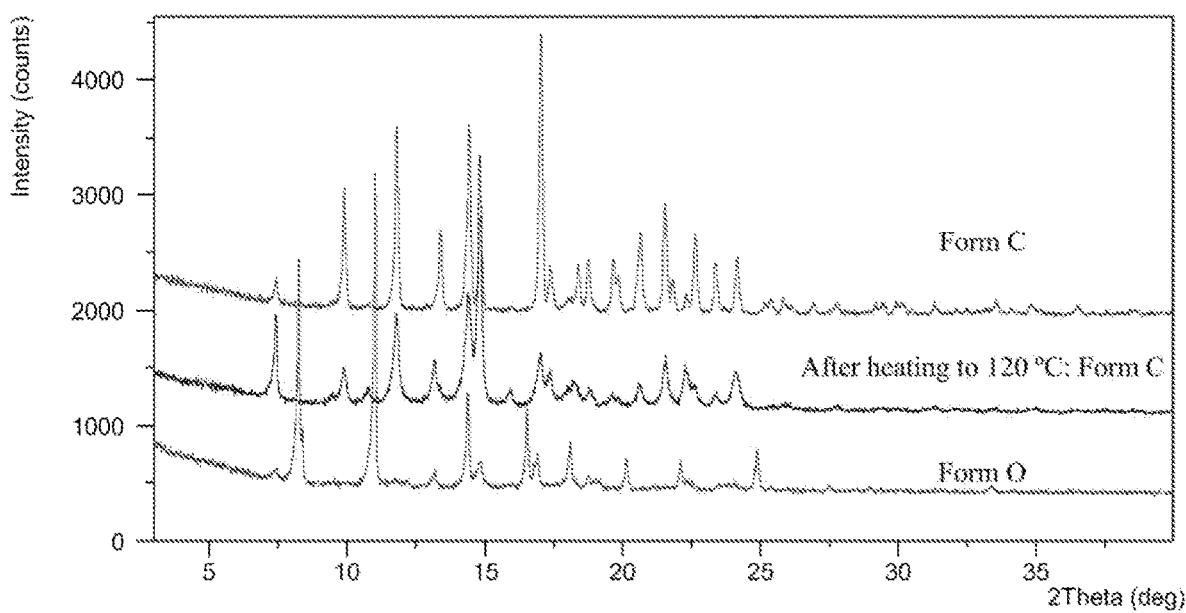
FIG. 14C depicts an overlay of exemplary XRPD patterns of Form O at selected temperatures along with an exemplary XRPD pattern of Form C.
Figure 14D:
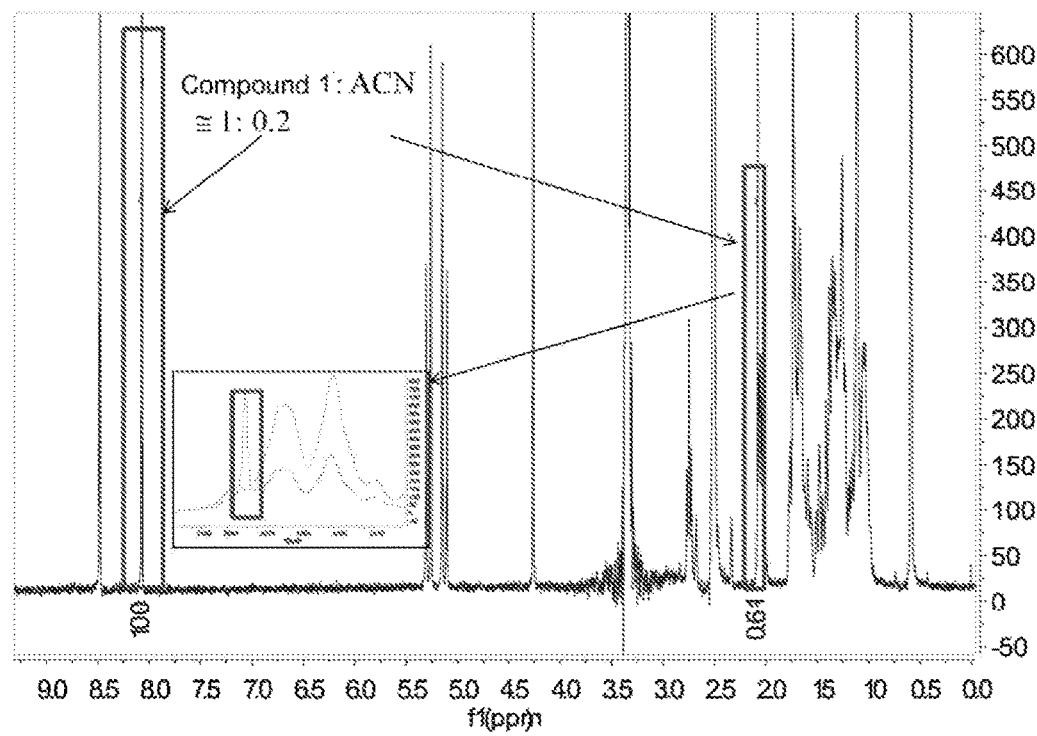
FIG. 14D depicts an exemplary 1H NMR spectrum of Form O dissolved in DMSO-$d_6$.

Form O: A 2-step weight loss of 5.3% up to 55.1° C., followed by 5.9% up to 200° C. is observed in the TGA curve presented in FIG. 14B. The DSC curve exhibits 3 endothermic peaks at 65.0° C., 168.5° C., and 210.8° C. (onset temperatures), corresponding to the loss of solvent to create Form C, transformation of Form C to Form K, and the melting point of Form K, respectively. In order to investigate the endotherms observed in the DSC analysis, Form O was heated to 120° C. resulting in a change to Form C, as shown in FIG. 14C. The $^1$H NMR spectrum revealed a molar ratio of 1:0.2 for Form 0: ACN (1.9% by weight) after heating to 50° C. in order to remove residual solvent, as illustrated in FIG. 14D.

Example 21. Hygroscopicity of Forms A, C, and K as Measured by DVS

Dynamic vapor sorption (DVS) was measured via an SMS (Surface Measurement Systems) DVS Intrinsic system. The relative humidity at 25° C. was calibrated against the deliquescence point of LiCl, Mg(NO$_3$)$_2$, and KCl. Instrument parameters for the DVS system used throughout this study are listed in Table 12.

TABLE 13

Parameters for DVS Test

| Parameters | DVS |
| --- | --- |
| Temperature | 25° C. |
| Sample size | 10~20 mg |
| Gas and flow rate | N$_2$, 200 mL/min |
| dm/dt | 0.002%/min |
| Min. dm/dtstabilityduration | 10 min |
| Max. equilibrium time | 180 min |
| RH range | 0% RH to 95% RH |
| RH step size (sorption) | 10% RH from 0% RH to 90% RH |
| | 5% RH from 90% RH to 95% RH |
| RH step size (desorption) | 10% RH from 90% RH to 0% RH |
| | 5% RH from 95% RH to 90% RH |

The hygroscopicity of Form A, Form C, and Form K were investigated at 25° C. using DVS. The XRPD patterns of each sample before and after DVS were compared in order to investigate any potential form change.

Figure 1E:
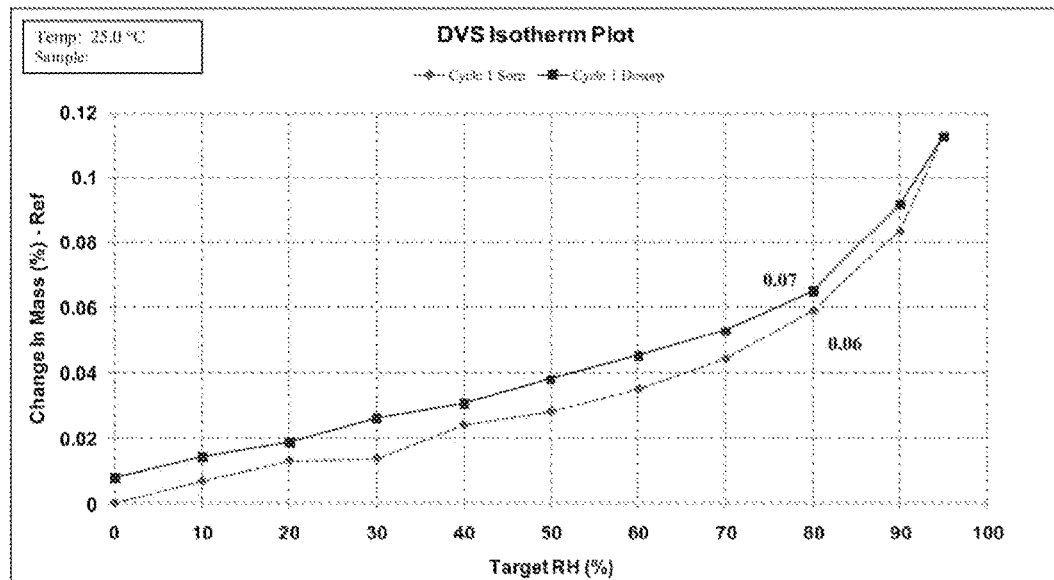
FIG. 1E depicts an exemplary DVS isotherm of Form A at 25° C.
Figure 1F:
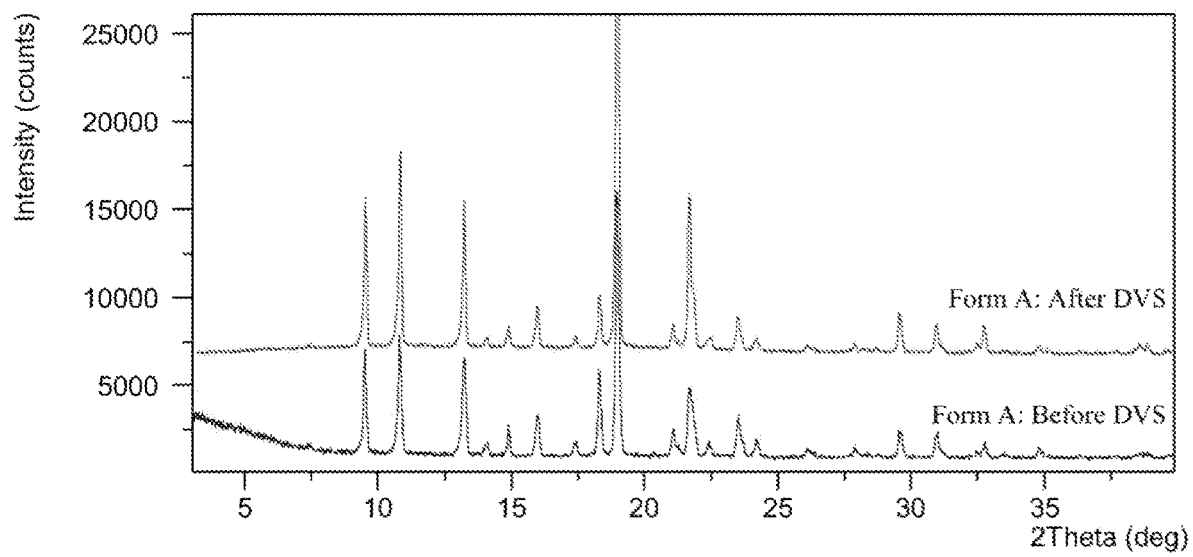
FIG. 1F depicts an exemplary XRPD patterns of Form A before and after an exemplary DVS measurement at 25° C.

The DVS isotherm plot of Form A shown in FIG. 1E exhibits 0.06% by weight water uptake at 80% RH and less than 0.12% by weight water uptake at 95% RH, revealing that Form A is non-hygroscopic. The XRPD pattern in FIG. 1F indicates there is no form change before and after DVS for Form A.

Figure 3F:
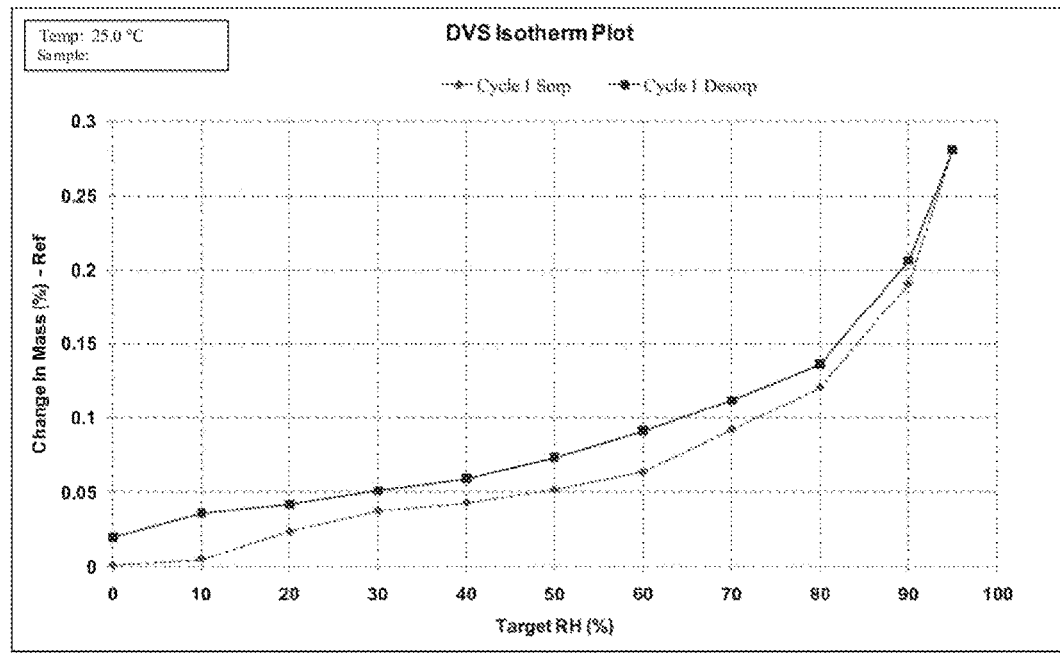
FIG. 3F depicts an exemplary DVS isotherm of Form C at 25° C.
Figure 3G:
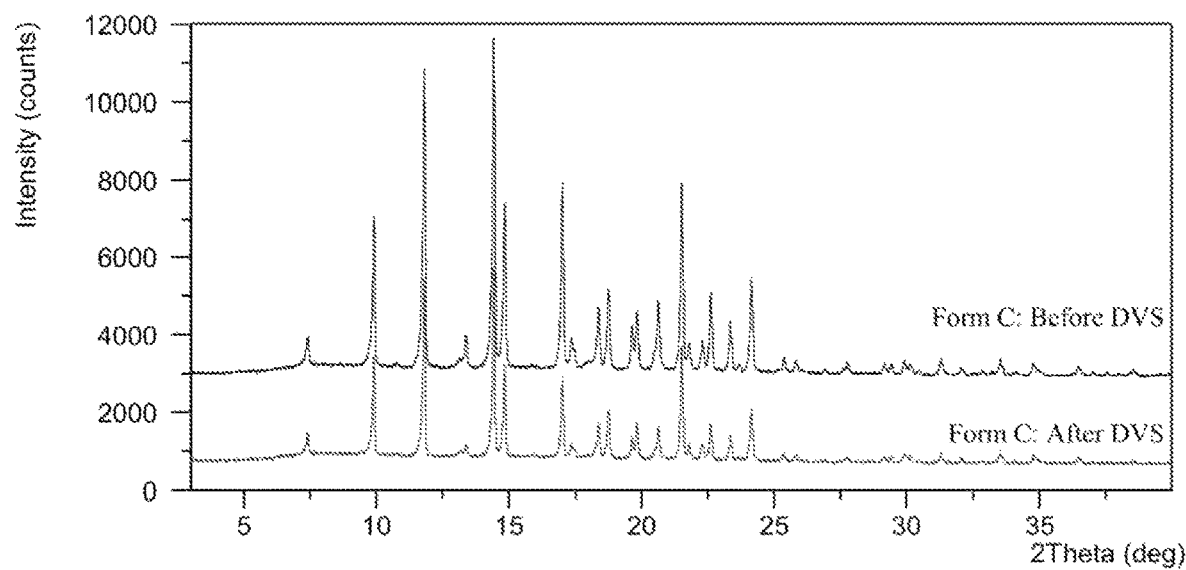
FIG. 3G depicts an overlay of exemplary XRPD patterns of Form C before and after a DVS measurement at 25° C.

Similarly, the DVS isotherm plot of Form C shown in FIG. 3F exhibits 0.12% by weight water uptake at 80% RH and less than 0.30% by weight water uptake at 95% RH, indicating that Form C is non-hygroscopic. The XRPD pattern in FIG. 3G shows there is no form change before and after DVS for Form C.

Figure 10C:
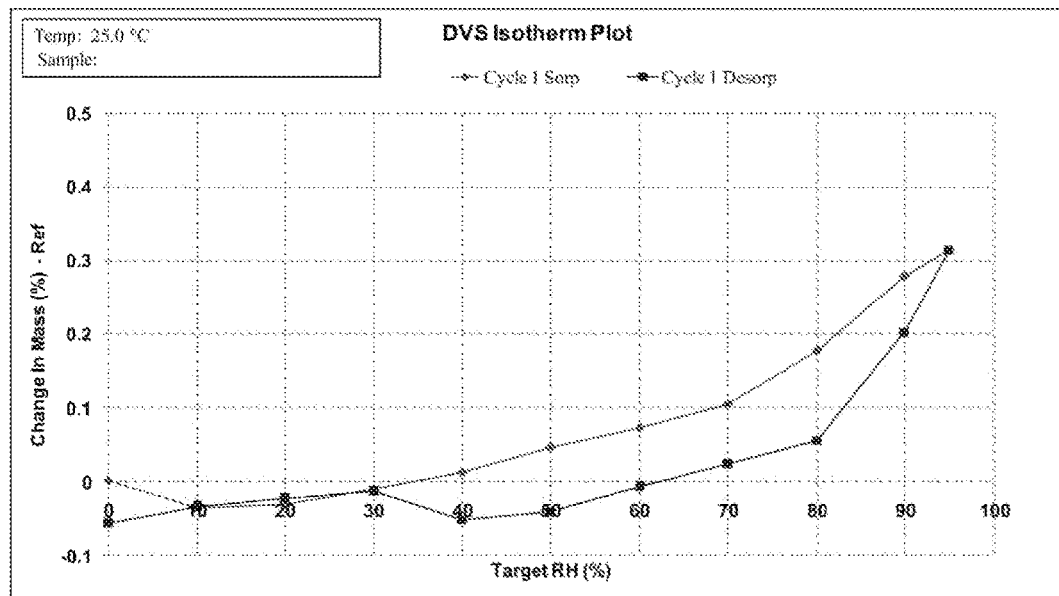
FIG. 10C depicts an exemplary DVS isotherm of Form K at 25° C.
Figure 10D:
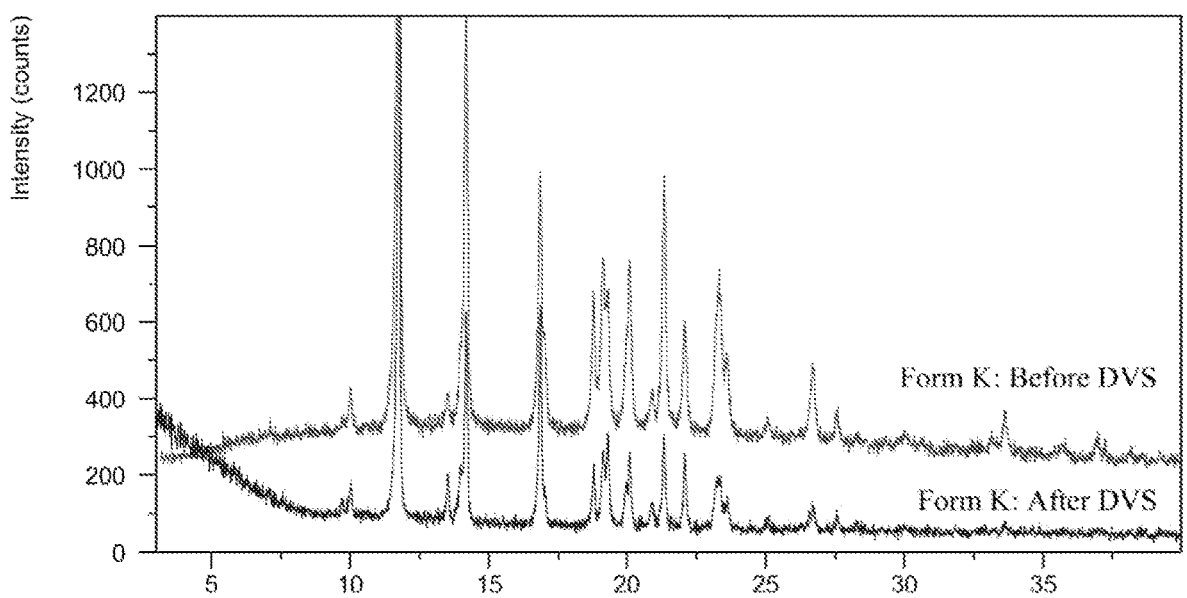
FIG. 10D depicts an overlay of exemplary XRPD patterns of Form K before and after an exemplary DVS measurement at 25° C.

The DVS isotherm plot of Form K shown in FIG. 10C exhibits 0.18% by weight water uptake at 80% RH and less than 0.35% by weight water uptake at 95% RH, revealing that Form K is non-hygroscopic. The XRPD pattern in FIG. 10D shows there is no form change before and after DVS for Form K.

Example 22. Interconversion of Forms A, C, and K Through Slurry Conversion

In one embodiment, the inter-conversion between Forms A, C and K can be studied in a series of slurry conversion experiments conducted in ethyl acetate, n-butanol, and methyl tert-butyl ether (MBTE) at both room temperature (RT) and 50° C. Compound 1 can display moderate solubility, and may yield solvated forms during these screening experiments. Results of the slurry conversion experiments are summarized in Table 14. The transition temperature between Forms A and C was estimated to be ~17° C., and the transition temperature between Forms K and C was above 100° C.

TABLE 14

Summary of Slurry Conversion Experiments

| Solvent | Condition | Initial Form | Final Form |
|---------|-----------|--------------|------------|
| Ethyl acetate | RT | Forms A and K (with Form C seeds) | Form C |
| | 50° C. | Forms A and K | Form C |
| n-Butanol | RT | Forms A, C and K | Form C |
| | 50° C. | Forms A, C and K | Form C |
| MBTE | RT | Forms A, C and K | Form C |
| | 50° C. | Forms A, C and K | Form C |

Example 23. Conversion of Form A to Form C with Form C Seed Crystals

Approximately 200 g/L-225 g/L solubilized Compound 1 (originally Form A) in ethyl acetate was heated to a temperature of 65° C. in the presence of 0.2%-1.0% of seed crystals of Form C for 1-3 hours. The batch can then be slowly cooled down to a temperature between 25° C.-30° C. for no less than 3 hours to obtain Form C. Seed crystals of Form C can be obtained using the procedure described in Example 4.

Figure 15:
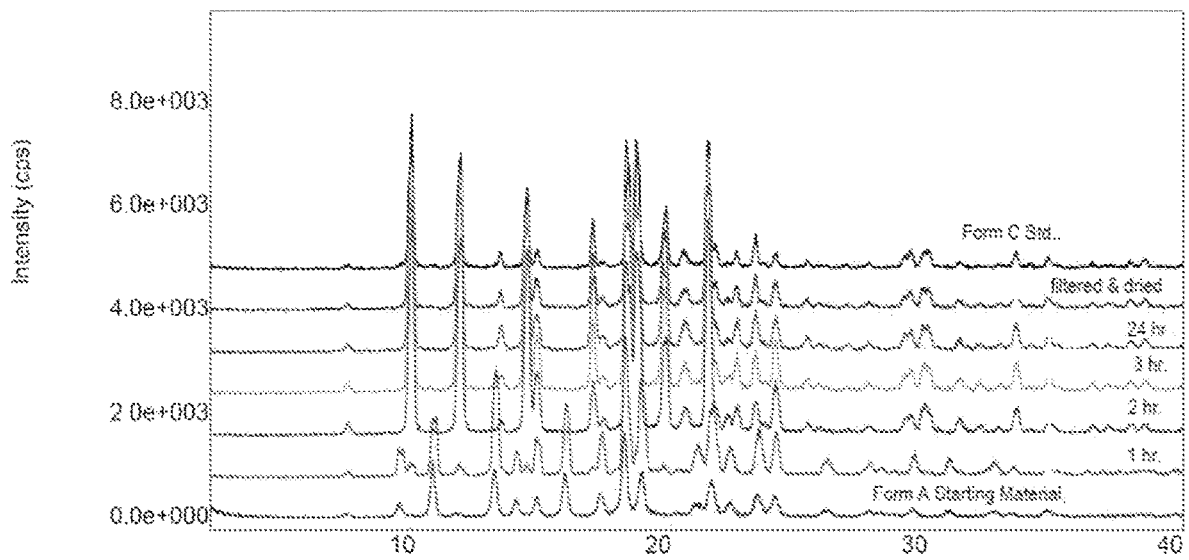
FIG. 15 depicts an overlay of exemplary XRPD patterns indicating the time-dependent conversion of Form A to Form C in ethyl acetate at an elevated temperature in the presence of seed crystals of Form C.

XRPD was performed using a Rigaku MiniFlex 600 (Cu Kα radiation at 40 kV tube voltage and 15 mA tube current) with a scanning range of 2° to 40° for 2θ, a step size of 0.01°, and a scanning speed of 1° or 2° per minute. XRPD was used to monitor the conversion from 225 g/L Form A to Form C in ethyl acetate at 65° C. using 1.0% of seed crystals of Form C with time, as indicated in FIG. 15.

Example 24. Preparation and Characterization of Form P

During solubility measurements, an XRPD pattern was detected in (a) slurries of Form A in EtOAc at 5° C. (after 1 h) and 20° C. (after 2 days), (b) slurries of Form C in EtOAc at 5° C. (after 1 h) and 20° C. (after 7 days). There was no direct match of this solid form's XRPD pattern to other crystal forms of Compound 1. The results indicate that this solid form of Compound 1 in EtOAc, termed Form P, is more stable than both Forms A and C in EtOAc at least at ≤20° C.

The wet cake of Form P (~5 min air) was dried in two ways: (a) under air at room temperature overnight, and (b) under vacuum at 40° C. for 3 hours. Both dried cakes were analyzed by XRPD, 1H-NMR, and TGA. XRPD data are presented in FIG. 16. NMR data are presented in FIG. 17A FIG. 17B. TGA data are presented in FIG. 18A FIG. 18B. The air dried cake gave an XRPD pattern conforming to Form P, about 1% weight loss by TGA up to about 50° C., and EtOAc peaks by $^1$H NMR. This indicates that Form P is an EtOAc solvate of Compound 1. The sample of Form P post-oven drying, on the other hand, gave an XRPD pattern conforming to Form A, no weight loss ≤100° C. by TGA, and no EtOAc peaks by $^1$H-NMR. Therefore, the data suggests that Form P is a solvate of Form A and converts to Form A upon drying.

Example 25. Solubility and Relative Stability of Forms A, C and P

Solubility profiles of Forms A, C and P across a range of temperature can give an indication of the relative stability of different forms within different temperature ranges. Sufficient equilibrium solubility data were collected experimentally covering 5-70° C. The results are presented in Table 12 and FIG. 19.

The data indicate that (1) Form C is more stable than Form A across the entire processing temperature range, (2) Form P becomes more stable than Form C≤20° C., (3) there is little interconversion between the three forms around 25~30° C. due to slow conversion kinetics, (4) Form P becomes unstable in EtOAc at ≥35° C. and converts to Form A; and (5) Form P converts into Form A upon drying in air or $N_2$.

Figure 20:
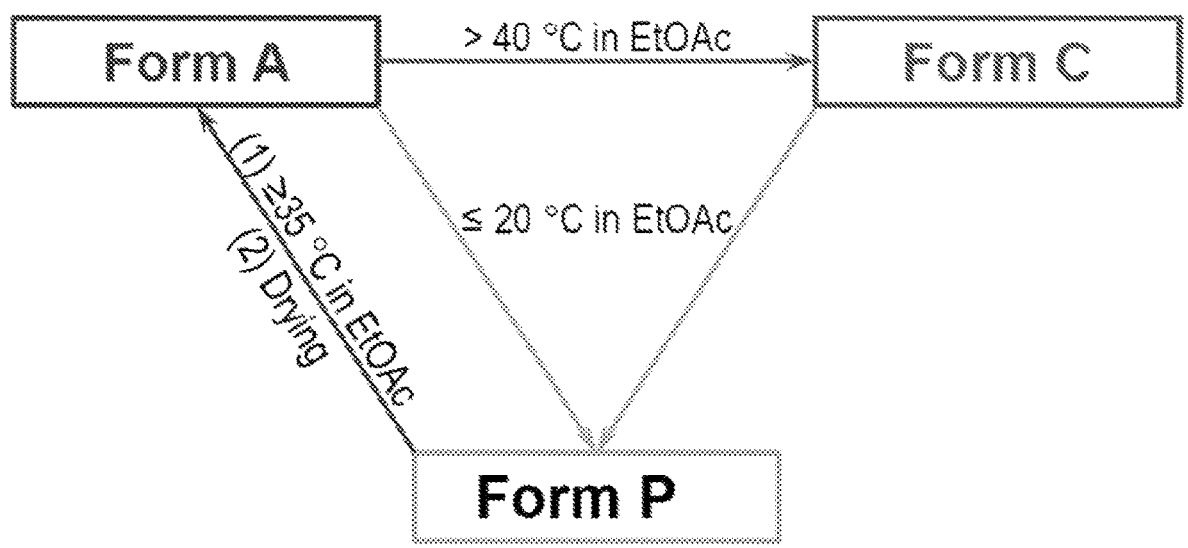
FIG. 20. depicts an exemplary phase relationship between Forms A, C, and P.

A phase relationship of Forms A, C and P in EtOAc is illustrated in FIG. 20. In EtOAc at low temperatures Forms A and C can convert to Form P. Form A can also be generated from Form C at too low of a temperature (e.g., aimed for a better isolation yield).

TABLE 12

Solubility data of Forms A, C, and P.

| Temperature (° C.) | Solubility (mg/mL) | | | Equilibration Time | Crystal Form Checked by XRPD |
|---|---|---|---|---|---|
| | Form A | Form C | Form P (Solvate) | | |
| 5 | NA | | 5.4 | 20 h | Form P |
| 10 | | | 6.6 | 3 day | Form P |
| 15 | | | 8.0 | 2 day | Form P |
| 20 | 12.4 | 11.8 | 11.4 | 2 day | No Form Change |
| 25 | — | — | 12.6 | 20 h | Form P |
| 30 | 15.5 | 14.9 | — | 4 h | No Form Change |
| | — | — | 13.5 | 20 h | Form P |
| 40 | 18.8 | 17.9 | — | 7 h | No Form Change |
| | | | | 24 h | Form P to Form A |
| 50 | 25 | 23.7 | — | 20 h | No Form Change |
| 60 | 31.7 | 29.8 | — | 4 h | No Form Change |

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A method for treating a CNS-related disorder, wherein the CNS-related disorder is a mood disorder, a psychotic disorder, an anxiety disorder, tremor, or tinnitus, in a subject in need thereof, comprising administering to the subject an effective amount of a crystalline solid Form C of Compound 1:

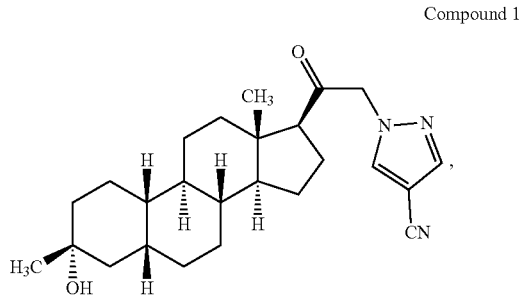

Compound 1 wherein the crystalline solid Form C of Compound 1 has an XRPD pattern comprising peaks between and including 9.7 to 10.1 degrees in 2θ, between and including 11.6 to 12.0 degrees in 2θ, between and including 13.2 to 13.6 degrees in 2θ, between and including 14.2 to 14.6 degrees in 2θ, between and including 14.6 to 15.0 degrees in 2θ, between and including 16.8 to 17.2 degrees in 2θ, between and including 20.5 to 20.9 degrees in 2θ, between and including 21.3 to 21.7 degrees in 2θ, between and including 21.4 to 21.8 degrees in 2θ, and between and including 22.4 to 22.8 degrees in 2θ.

2. The method of claim 1, wherein the peak between and including 9.7 to 10.1 is 9.9 degrees in 2θ, the peak between and including 11.6 to 12.0 is 11.8 degrees in 2θ, the peak between and including 13.2 to 13.6 is 13.4 degrees in 2θ, the peak between and including 14.2 to 14.6 is 14.4 degrees in 2θ, the peak between and including 14.6 to 15.0 degrees is 14.8 in 2θ, the peak between and including 16.8 to 17.2 is 17.0 degrees in 2θ, the peak between and including 20.5 to 20.9 is 20.7 degrees in 2θ, the peak between and including 21.3 to 21.7 is 21.5 degrees in 2θ, the peak between and including 21.4 to 21.8 is 21.6 degrees in 2θ, and the peak between and including 22.4 to 22.8 is 22.6 degrees in 2θ.

3. The method of claim 1, wherein the mood disorder is treatment-resistant depression.

4. The method of claim 1, wherein the mood disorder is a major depressive disorder (MDD).

5. The method of claim 1, wherein the mood disorder is postpartum depression (PPD) or perinatal depression.

6. The method of claim 1, wherein the anxiety disorder is a generalized anxiety disorder.

7. The method of claim 1, wherein the tremor is essential tremor.

8. The method of claim 1, wherein the psychotic disorder is bipolar disorder.

9. The method of claim 1, wherein the crystalline solid Form C of Compound 1 is administered orally, parenterally, intradermally, intrathecally, intramuscularly, subcutaneously, vaginally, as a buccal, sublingually, rectally, as a topical, as an inhalation, intranasally, or transdermally.

10. A method for treating a CNS-related disorder, wherein the CNS-related disorder is a mood disorder, a psychotic disorder, an anxiety disorder, tremor, or tinnitus, in a subject in need thereof, comprising administering to the subject an effective amount of a crystalline solid Form C of Compound 1:

Compound 1

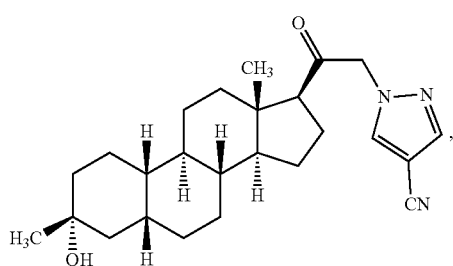

wherein the crystalline solid Form C of Compound 1 has an XRPD pattern comprising peaks between and including 9.7 to 10.1 degrees in 2θ, between and including 14.6 to 15.0 degrees in 2θ, between and including 16.8 to 17.2 degrees in 2θ, between and including 20.5 to 20.9 degrees in 2θ, and between and including 21.3 to 21.7 degrees in 2θ.

11. The method of claim 10, wherein the tremor is essential tremor.

12. The method of claim 10, wherein the psychotic disorder is bipolar disorder.

13. The method of claim 10, wherein the crystalline solid Form C of Compound 1 is administered orally, parenterally, intradermally, intrathecally, intramuscularly, subcutaneously, vaginally, as a buccal, sublingually, rectally, as a topical, as an inhalation, intranasally, or transdermally.

14. The method of claim 13, wherein the crystalline solid Form C of Compound 1 is administered orally.

15. A method for treating a CNS-related disorder, wherein the CNS-related disorder is a mood disorder, a psychotic disorder, an anxiety disorder, tremor, or tinnitus, in a subject in need thereof, comprising administering to the subject an effective amount of a crystalline solid Form C of Compound 1:

Compound 1

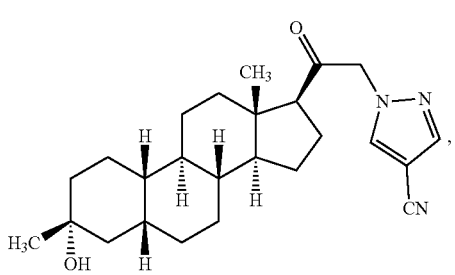

wherein the crystalline solid Form C of Compound 1 has an XRPD pattern comprising peaks at 9.9 degrees in 2θ, 14.8 degrees in 2θ, 17.0 degrees in 2θ, 20.7 degrees in 2θ, and 21.5 degrees in 2θ.

16. The method of claim 15, wherein the tremor is essential tremor.

17. The method of claim 15, wherein the psychotic disorder is bipolar disorder.

18. The method of claim 15, wherein the crystalline solid Form C of Compound 1 is administered orally, parenterally, intradermally, intrathecally, intramuscularly, subcutaneously, vaginally, as a buccal, sublingually, rectally, as a topical, as an inhalation, intranasally, or transdermally.

19. The method of claim 18, wherein the crystalline solid Form C of Compound 1 is administered orally.

* * * * *